(12) United States Patent
Welch et al.

(10) Patent No.: US 10,892,421 B2
(45) Date of Patent: *Jan. 12, 2021

(54) ORGANIC SMALL MOLECULE SEMICONDUCTING CHROMOPHORES FOR USE IN ORGANIC ELECTRONIC DEVICES

(71) Applicant: The Regents of the University of California, a body corporate, Oakland, CA (US)

(72) Inventors: Gregory C. Welch, Santa Barbara, CA (US); Corey V. Hoven, Santa Barbara, CA (US); Thuc-Quyen Nguyen, Santa Barbara, CA (US); Guillermo C. Bazan, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/892,283

(22) Filed: Feb. 8, 2018

(65) Prior Publication Data

US 2018/0301634 A1 Oct. 18, 2018

Related U.S. Application Data

(63) Continuation of application No. 13/988,756, filed as application No. PCT/IS2011/061963 on Nov. 22, 2011, now Pat. No. 9,893,294.

(60) Provisional application No. 61/416,251, filed on Nov. 22, 2010.

(51) Int. Cl.
*H01L 51/00* (2006.01)
*C07D 498/04* (2006.01)
*C07D 513/04* (2006.01)
*H01L 51/42* (2006.01)

(52) U.S. Cl.
CPC ........ *H01L 51/0061* (2013.01); *C07D 498/04* (2013.01); *C07D 513/04* (2013.01); *H01L 51/0068* (2013.01); *H01L 51/0071* (2013.01); *H01L 51/0094* (2013.01); *H01L 51/0037* (2013.01); *H01L 51/4253* (2013.01); *H01L 2251/308* (2013.01); *Y02E 10/549* (2013.01)

(58) Field of Classification Search
CPC ............. H01L 51/0061; H01L 51/0068; H01L 51/0071; H01L 51/0094; C07D 498/04; C07D 513/04
USPC ............................... 546/112, 14, 114; 257/40
See application file for complete search history.

(56) References Cited

U.S. PATENT DOCUMENTS

| | | | |
|---|---|---|---|
| 5,059,863 A | 10/1991 | Tashiro et al. | |
| 6,559,277 B2 | 5/2003 | Rietz et al. | |
| 7,482,490 B2 | 1/2009 | Nishiyama et al. | |
| 8,343,382 B2 | 1/2013 | Bazan et al. | |
| 9,293,708 B2 | 3/2016 | Bazan et al. | |
| 9,865,821 B2* | 1/2018 | Tamayo | C07F 7/0807 |
| 9,893,294 B2 | 2/2018 | Welch et al. | |
| 2004/0048102 A1 | 3/2004 | Igarashi | |
| 2004/0067387 A1 | 4/2004 | Kim et al. | |
| 2005/0026927 A1 | 2/2005 | Boettcher et al. | |
| 2005/0201887 A1 | 9/2005 | Bernhard et al. | |
| 2006/0052612 A1 | 3/2006 | Stossel et al. | |
| 2007/0037012 A1 | 2/2007 | Kim et al. | |
| 2007/0286997 A1 | 12/2007 | Terao et al. | |
| 2008/0027226 A1 | 1/2008 | Rogers et al. | |
| 2009/0267060 A1 | 10/2009 | Forrest et al. | |
| 2010/0252112 A1 | 10/2010 | Watson | |
| 2010/0326525 A1 | 12/2010 | Nguyen et al. | |
| 2011/0028656 A1 | 2/2011 | Bazan et al. | |
| 2011/0111350 A1 | 5/2011 | Lakshmi et al. | |
| 2011/0156018 A1 | 6/2011 | Moriwaki et al. | |
| 2011/0288253 A1 | 11/2011 | Reynolds et al. | |
| 2012/0205596 A1 | 8/2012 | Yoshimura et al. | |
| 2012/0322966 A1 | 12/2012 | Bazan et al. | |
| 2013/0032791 A1 | 2/2013 | Bazan et al. | |
| 2013/0247989 A1 | 9/2013 | Bazan et al. | |
| 2015/0034161 A1 | 2/2015 | Tamayo et al. | |
| 2016/0020413 A1 | 1/2016 | Tamayo et al. | |
| 2017/0133597 A1* | 5/2017 | Lee | H01L 51/0036 |
| 2017/0133611 A1* | 5/2017 | Wang | H01L 51/0558 |
| 2018/0282474 A1* | 10/2018 | Wang | C08G 61/126 |

FOREIGN PATENT DOCUMENTS

| | | |
|---|---|---|
| CN | 1203609 A | 12/1998 |
| CN | 1671675 A | 9/2005 |
| CN | 101139317 A | 3/2008 |
| CN | 101884123 A | 11/2010 |
| JP | 2001097949 A | 4/2001 |
| JP | 2003123973 A | 4/2003 |
| JP | 2005258388 A | 9/2005 |
| JP | 2008231051 A | 10/2008 |
| JP | 4501588 B2 | 7/2010 |
| WO | WO-98/042712 A1 | 10/1998 |
| WO | WO-2009/051684 A1 | 4/2009 |

(Continued)

OTHER PUBLICATIONS

Bibi; New J. Chem., 2016, 40, 3693-3704. (Year: 2016).*
Lu; Dyes and Pigments 2016, 127, 189-196. (Year: 2016).*
Yong; J. Mater. Chem., 2011, 21, 11159-11166. (Year: 2011).*
Lim; J. Mater. Chem. C, 2014, 2, 8412-8422. (Year: 2014).*
Wong; Journal of Organometallic Chemistry, 2009, 694, 2644-2647. (Year: 2009).*

(Continued)

*Primary Examiner* — Daniel R Carcanague
(74) *Attorney, Agent, or Firm* — Morrison & Foerster LLP

(57) ABSTRACT

Small organic molecule semi-conducting chromophores containing a pyridalthiadiazole, pyridaloxadiazole, or pyridaltriazole core structure are disclosed. Such compounds can be used in organic heterojunction devices, such as organic small molecule solar cells and transistors.

17 Claims, 27 Drawing Sheets

(56) References Cited

FOREIGN PATENT DOCUMENTS

| | | | |
|---|---|---|---|
| WO | WO-2010/026972 A1 | 3/2010 | |
| WO | WO-2010/046114 A2 | 4/2010 | |
| WO | WO-2010/090123 A1 | 8/2010 | |
| WO | WO-2010/114497 A1 | 10/2010 | |
| WO | WO-2011/156478 A2 | 12/2011 | |
| WO | WO-2012074853 A1 * | 6/2012 | ........... C07D 498/04 |
| WO | WO-2013/123047 A1 | 8/2013 | |
| WO | WO-2013/123508 A2 | 8/2013 | |
| WO | WO-2016/154624 A1 | 9/2016 | |
| ZA | 9802362 B | 3/1998 | |

OTHER PUBLICATIONS

Anant, P. et al. (2008). "A Simple Route Toward the Synthesis of Bisbenzothiadiazole Derivatives," *Organic Letters* 10(24):5533-5536.

Blouin, N. et al. (Jan. 16, 2008). "Toward a Rational Design of Poly (2, 7-Carbazole) Derivatives for Solar cells" J. Am. Chem. Soc. 130(2)732-742. http://pubs.acs.org/doi/pdf/10.1021 /ja0771989; published Sep. 19, 2007; accessed and printed May 19, 2015.

Bouffard, J. et al. (2008) "Fluorescent Conjugated Polymers That Incorporate Substituted 2, 1, 3-benzooxadiazole and 2, 1, 3-Benzothiadiazole Units," *Macromolecules* 41(15):559-5562.

O'Regan, B. et al. (Oct. 24, 1991). "A Low-Cost, High-Efficiency Solar Cell Based on Dye-sensitized Colloidal $TiO_2$ Films," *Nature* 353:737-740.

Chen, J.J. et al. (2010). "Quinacridone-Based Molecular Donors for Solution Processed Bulk-Heterojunction Organic Solar Cells," *Applied Materials and Interfaces* 2(9):2679-2686.

Driscoll, K. et al. (2010). "Enhanced Photoresponse in Solid-State Excitonic Solar Cells via Resonant Energy Transfer and Cascaded Charge Transfer from a Secondary Absorber," *Nano Letters* 10:4981-4988.

Gorohmaru, H. et al. (2002). "Preparation of 4,7-Dihetaryl-1,2,5-Oxadiazolo[3,4-c]-Pyridines as red Fluorescent Materials," *Heterocycles* 56:421-431.

Henson, Z. et al. (2012). "Pyridalthiadiazole-Based Narrow Band gap Chromophores," *J. Am. Chem. Soc.* 134:3766-3779.

Hou, J.H, et al. (2008). "Synthesis, characterization, and photovoltaic properties of a low band gap polymer based on silole-containing polythiophenes and 2,1,3-benzothiadiazole," *Journal of the American Chemical Society* 130:16144-16145.

Liang, D. et al. (2009). "First Principles Calculations of Optical and Electronical Properties for 2,7-carnazole derivatives as solar cells materials," *Journal of Molecular Structure: Theochem* 908:102-106.

Melucci, M. et al. (2010). "Thiophene-Benzothiadiazole Co-Oligomers: Synthesis, Optoelectronic Properties, Electrical Characterization, and Thin-Film Patterning," *Advanced Functional Materials* 20:445-452.

Koga, T. et al., (Mar. 5, 2002) "Fluorescence Spectroscopic Characterization of 4,7-bis(2-thienyl)-1,2,5-oxadiazolo[3,4-c]pyridine; Lead Structure of new Red-Emitting EL Material," *Chemical Physics Letters* 354:173-178.

Omer, K.M. et al. (2009; e-published on Jul. 6, 2009). "Green Electrogenerated Chemiluminescence of Highly Fluorescent Benzothiadiazole and Fluorene Derivatives," *J. Am. Chem. Soc.* 131(30):10733-10741.

Peet, J. et al. (Jul. 2007; e-published on May 27, 2007). "Efficiency Enhancement in low-bandgap Polymer Solar Cells by Processing with Alkane Dithols," *Nature Materials* 6:497-500.

Sonar, P. et al. (Apr. 1, 2010) "1,3,6,8-Tetrasubstituted Pyrenes: Solution-Processable Materials for Application in Organic Electronics," *Organic Letters* 12(15)3292-3295.

Sun, Y. et al. (Jan. 2012, e-pub Nov. 2011). "Solution-Processed Small-Molecule Solar Cells with 6.7% Efficiency," *Nature Materials* 11:44-48.

Welch, G.C. et al. (2009; e-published on Jul. 8, 2009). "Band Gap Control in Conjugated Oligomers via Lewis Acids," *J. Am. Chem. Soc.* 131(31):10802-10803.

Zhou, H. et al. (2010). "Enhanced Photovoltaic Performance of Low-Bandgap Polymers with Deep LUMO Levels," *Angew, Chem. Int. Ed.* 49:7992-7995.

International Search Report dated Jun. 7, 2012 for PCT Application No. PCT/US2011/061963, filed on Nov. 22, 2011, 4 pages.

* cited by examiner

Selected determination of HOMO-LUMO values

Experimental examples of optoelectronic devices using a compound of the invention Example of organic solar cell device using material 103:

Energy level diagram of all components of a standard bulk-heterojunction solar cell device Table 1: solar cell data using compound 103 (as-cast active layer from chloroform)

| 103:PCBM Ratio | 30:70 | 40:60 | 50:50 | 60:40 | 70:30 |
|---|---|---|---|---|---|
| $V_{oc}$: | 0.66 | 0.68 | 0.70 | 0.74 | 0.80 |
| $I_{sc}$: | -5.43 | -6.13 | -4.75 | -2.96 | -1.53 |
| FF: | 0.31 | 0.31 | 0.30 | 0.27 | 0.26 |
| PCE: | 1.12% | 1.29% | 0.99% | 0.59% | 0.32% |

Current-voltage plots of BHJ devices fabricated using the device architectures ITO/PEDOT:PSS/103:PC$_{71}$BM/Al. Active layer composition was varied from 30:70 103:PC$_{71}$BM to 70:30 103:PC$_{71}$BM. Active layers cast from 2% chloroform solutions at 1500 rpm. Active layer thickness = 75nm.

Figure 20

Table 2: solar cell data using compound 103 (annealed active layer cast from chloroform)

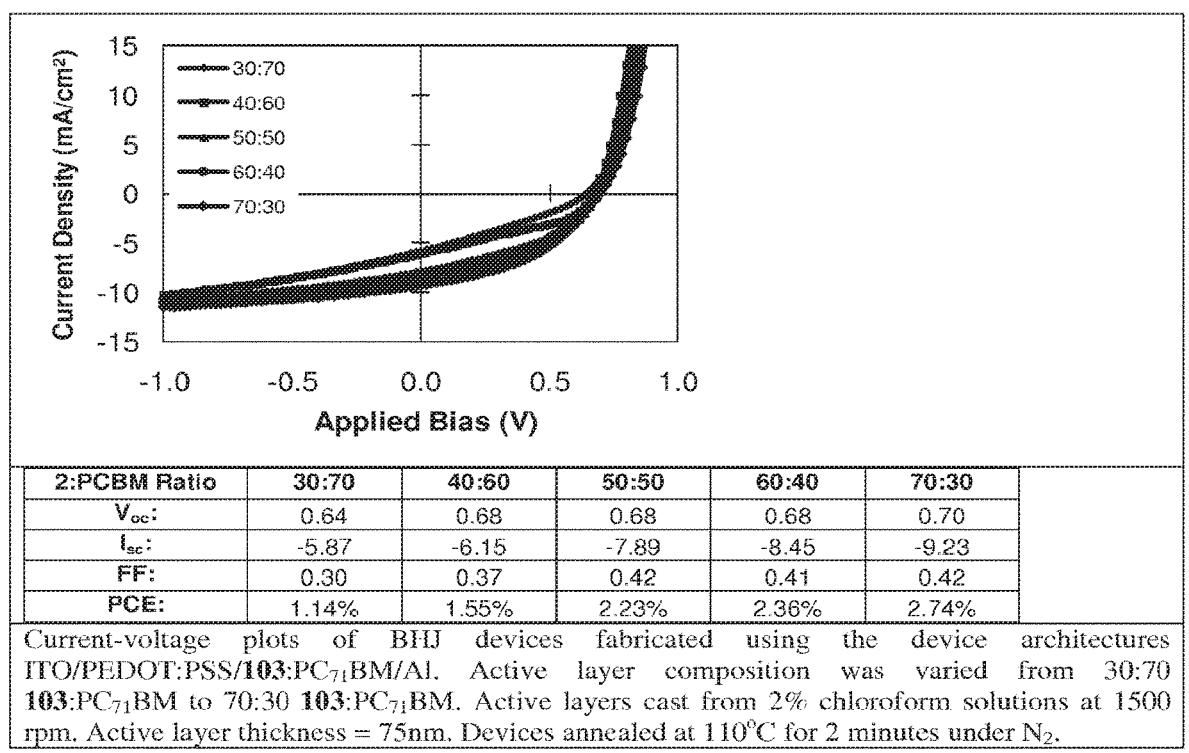

| 2:PCBM Ratio | 30:70 | 40:60 | 50:50 | 60:40 | 70:30 |
|---|---|---|---|---|---|
| $V_{oc}$: | 0.64 | 0.68 | 0.68 | 0.68 | 0.70 |
| $I_{sc}$: | -5.87 | -6.15 | -7.89 | -8.45 | -9.23 |
| FF: | 0.30 | 0.37 | 0.42 | 0.41 | 0.42 |
| PCE: | 1.14% | 1.55% | 2.23% | 2.36% | 2.74% |

Current-voltage plots of BHJ devices fabricated using the device architectures ITO/PEDOT:PSS/103:PC$_{71}$BM/Al. Active layer composition was varied from 30:70 103:PC$_{71}$BM to 70:30 103:PC$_{71}$BM. Active layers cast from 2% chloroform solutions at 1500 rpm. Active layer thickness = 75nm. Devices annealed at 110°C for 2 minutes under N$_2$.

Table 3: solar cell data using compound 103 (as-cast active layer from chloroform)

| 2:PCBM Ratio | 30:70 | 40:60 | 50:50 | 60:40 | 70:30 |
|---|---|---|---|---|---|
| $V_{oc}$: | 0.68 | 0.70 | 0.70 | 0.74 | 0.80 |
| $I_{sc}$: | -6.57 | -7.38 | -6.37 | -3.65 | -2.06 |
| FF: | 0.30 | 0.29 | 0.28 | 0.27 | 0.27 |
| PCE: | 1.34% | 1.49% | 1.27% | 0.74% | 0.45% |

Current-voltage plots of BHJ devices fabricated using the device architectures ITO/PEDOT:PSS/103:$PC_{71}BM$/Al. Active layer composition was varied from 30:70 103:$PC_{71}BM$ to 70:30 103:$PC_{71}BM$. Active layers cast from 2% chloroform solutions at 2500 rpm. Active layer thickness = 85nm.

Figure 22

Table 4: solar cell data using compound 103 (annealed active layer cast from chloroform)

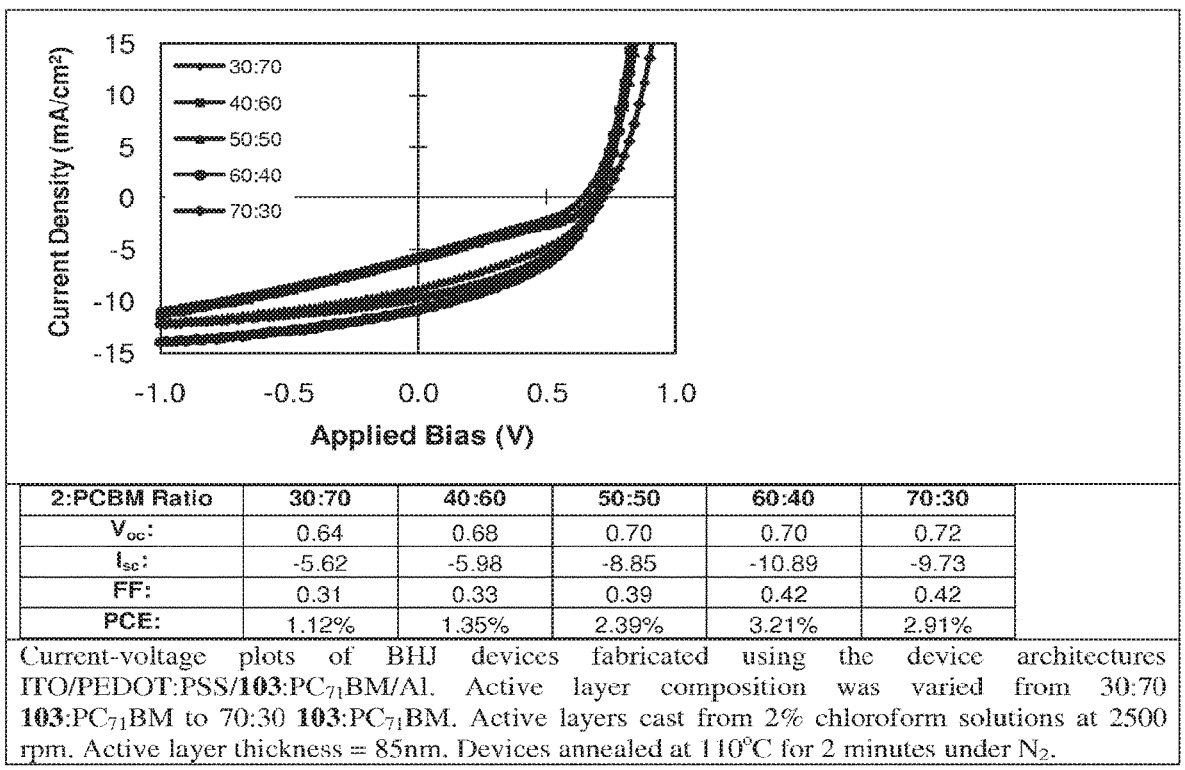

| 2:PCBM Ratio | 30:70 | 40:60 | 50:50 | 60:40 | 70:30 |
|---|---|---|---|---|---|
| $V_{oc}$: | 0.64 | 0.68 | 0.70 | 0.70 | 0.72 |
| $I_{sc}$: | -5.62 | -5.98 | -8.85 | -10.89 | -9.73 |
| FF: | 0.31 | 0.33 | 0.39 | 0.42 | 0.42 |
| PCE: | 1.12% | 1.35% | 2.39% | 3.21% | 2.91% |

Current-voltage plots of BHJ devices fabricated using the device architectures ITO/PEDOT:PSS/103:PC$_{71}$BM/Al. Active layer composition was varied from 30:70 103:PC$_{71}$BM to 70:30 103:PC$_{71}$BM. Active layers cast from 2% chloroform solutions at 2500 rpm. Active layer thickness = 85nm. Devices annealed at 110°C for 2 minutes under N$_2$.

Table 5: solar cell data using compound 103 (as-cast active layer from chloroform)

| 2:PCBM Ratio | 30:70 | 40:60 | 50:50 | 60:40 | 70:30 |
|---|---|---|---|---|---|
| $V_{oc}$: | 0.66 | 0.68 | 0.70 | 0.74 | 0.80 |
| $I_{sc}$: | -7.10 | -8.02 | -6.22 | -3.87 | -2.00 |
| FF: | 0.31 | 0.31 | 0.30 | 0.27 | 0.26 |
| PCE: | 1.47% | 1.69% | 1.30% | 0.78% | 0.41% |

Current-voltage plots of BHJ devices fabricated using the device architectures ITO/PEDOT:PSS/103:PC$_{71}$BM/Al. Active layer composition was varied from 30:70 103:PC$_{71}$BM to 70:30 103:PC$_{71}$BM. Active layers cast from 2% chloroform solutions at 3500 rpm. Active layer thickness = 105nm.

Figure 24

Table 4: solar cell data using compound 103 (annealed active layer cast from chloroform)

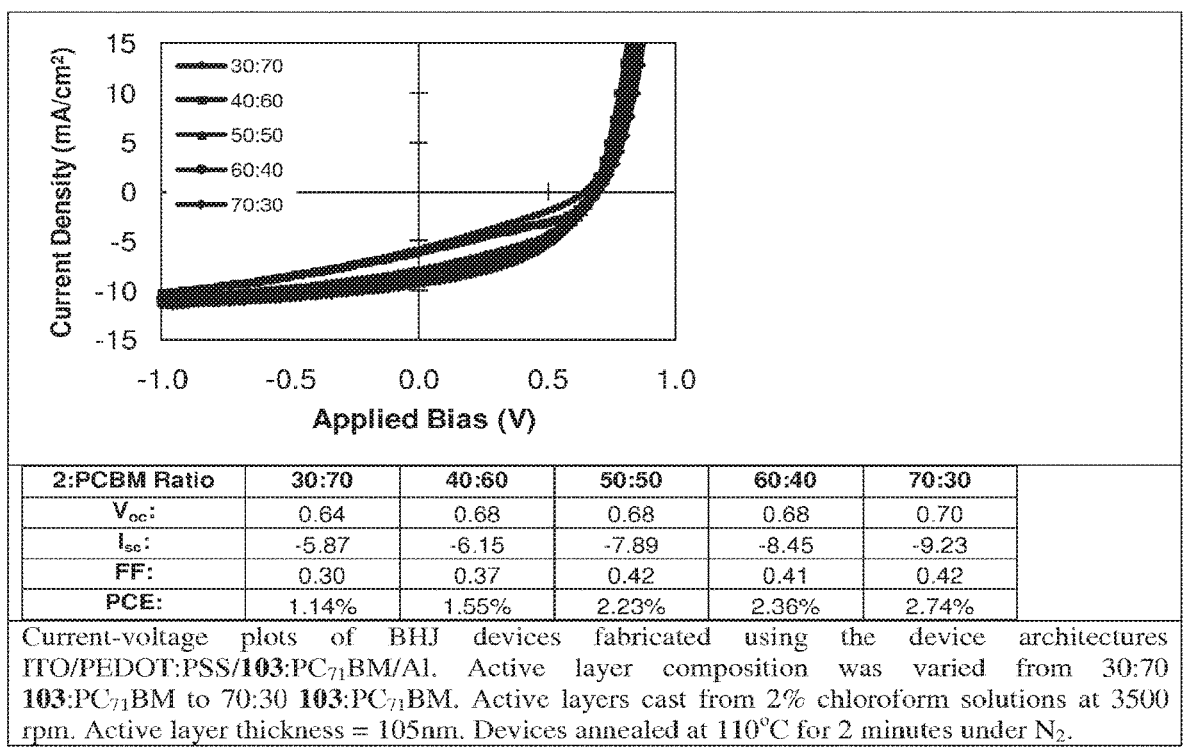

| 2:PCBM Ratio | 30:70 | 40:60 | 50:50 | 60:40 | 70:30 |
|---|---|---|---|---|---|
| $V_{oc}$: | 0.64 | 0.68 | 0.68 | 0.68 | 0.70 |
| $I_{sc}$: | -5.87 | -6.15 | -7.89 | -8.45 | -9.23 |
| FF: | 0.30 | 0.37 | 0.42 | 0.41 | 0.42 |
| PCE: | 1.14% | 1.55% | 2.23% | 2.36% | 2.74% |

Current-voltage plots of BHJ devices fabricated using the device architectures ITO/PEDOT:PSS/103:PC$_{71}$BM/Al. Active layer composition was varied from 30:70 103:PC$_{71}$BM to 70:30 103:PC$_{71}$BM. Active layers cast from 2% chloroform solutions at 3500 rpm. Active layer thickness = 105nm. Devices annealed at 110°C for 2 minutes under N$_2$.

Current density-voltage (J-V) curves spectra of 103:$PC_{71}BM$ (60:40 w/w) BHJ solar cell. Solar cell was annealed at 110°C for 2 minutes. Device architecture ITO/PEDOT:PSS/103:$PC_{71}BM$/Al. Active layer thickness = 85nm External Quantum Efficiency (EQE) spectra of 103:$PC_{71}BM$ (60:40 w/w) BHJ solar cell. Solar cell was annealed at 110°C for 2 minutes. Device architecture ITO/PEDOT:PSS/103:$PC_{71}BM$/Al. Active layer thickness = 85nm UV-vis-NIR absorption spectra of a 60:40 (w/w) blend of 103:$PC_{71}BM$ as-cast film from $CHCl_3$ (solid), and annealed film 110°C 2 minutes (large dashed).

ORGANIC SMALL MOLECULE SEMICONDUCTING CHROMOPHORES FOR USE IN ORGANIC ELECTRONIC DEVICES

CROSS-REFERENCE TO RELATED APPLICATIONS

This patent application is a continuation of U.S. application Ser. No. 13/988,756, which is a National Phase application under 35 USC § 371 of International Application No. PCT/US2011/061963 having an International Filing Date of Nov. 22, 2011, which claims priority benefit of U.S. Provisional Patent Application No. 61/416,251, filed Nov. 22, 2010. The entire contents of that application is those applications are hereby incorporated by reference herein.

STATEMENT REGARDING FEDERALLY SPONSORED RESEARCH OR DEVELOPMENT

This invention was made with United Stated government support under grant no. DE-DC0001009 awarded by the Center for Energy Efficient Materials of the Department of Energy and under grant no. N-00014-04-0411 awarded by the Office of Naval Research. The government has certain rights in the invention.

BACKGROUND OF THE INVENTION

Solution-processed organic photovoltaic devices (OPV) have emerged as a promising energy technology due to their ease of processing, low-cost, and ability to be fabricated, onto light-weight flexible substrates. Polymer based OPV's have by far been the most studied, and power conversion efficiencies (PCE's) above 6% have recently been reported for polymer:full creme, bulk heterojunction (BHJ) devices. On the other hand, solution processed small molecule BHJ devices have received far less attention. Such molecular hetero junctions (MHJ) have several advantages over their polymer counterparts, in that small molecules have well defined structures, are easily functionatized, are monodisperse, are readily purified, and do not suffer from batch-to-batch variations. Reports of efficient solution processed MHJ devices have recently emerged that have utilized merocyanine dyes, squaraine dyes, isoindigo, and diketopyrrolopyrrole based chromophores as the light harvesting donor component with a fullerene acceptor. PCE's have reached upwards of 4% for such devices. While these results are encouraging, there still exits a need for the development of novel discrete light harvesting materials. Key parameters for effective small molecule donors include having broad and efficient optical absorption that extends into the near-IR region to maximize photon absorption, deep HOMO levels from −5 to −5.5 eV to maximize open circuit voltages, relatively planar structures for high charge carrier mobility, high solution viscosity and solubilizing side chains for solution to film processing. Additionally, it is important that novel structures have facile and highly tunable syntheses to enable rapid and cheap generation of molecular libraries.

The present invention seeks to address the need for improved light harvesting molecules for molecular heterojunction devices by providing novel and advantageous materials for use in such devices.

SUMMARY OF THE INVENTION

In one embodiment, the present invention is directed to organic non-polymeric semiconducting chromophores containing the pyridalthiadiazole (PT, [1,2,5]thiadiazolo[3,4-c]pyridine), pyridaloxadiazole (PO, [1,2,5]oxadiazolo[3,4-c]pyridine), or pyridaltriazole (P3N, 2-H-[1,2,3]triazolo[4,5-c]pyridine) (or a 2-substituted P3N derivative) organic structure for use in heterojunction devices, such as organic small molecule solar cells and transistors. In one embodiment, the present invention is directed to non-polymeric electron-donating and electron-accepting chromophores having a pyridalthiadiazole (PT, [1,2,5]thiadiazolo[3,4-c]pyridine), pyridaloxadiazole (PO, [1,2,5]oxadiazolo[3,4-c]pyridine), or pyridaltriazole (P3N, 2-H-[1,2,3]triazolo[4,5-c]pyridine) (or a 2-substituted P3N derivative) core structure. In another embodiment, the present invention is directed to optoelectronic devices comprising an active layer composition of a mixture of a non-polymeric light-harvesting electron-donating chromophore based on a PT, PO, or P3N core structure with an electron-accepting material, such as a fullerene, methanofullerene, rylene diimides or related π-conjugated organic electron acceptors. Organic or inorganic electron acceptors can be used. In another embodiment, the present invention is directed to optoelectronic devices comprising an active layer composition of a mixture of a non-polymeric light-harvesting electron-accepting chromophore, based on a PT, PO, or P3N core structure with an electron-donating material. Organic or inorganic electron donors can be used. The present invention is also directed to methods of fabricating the devices by solution processing. In one embodiment, all active layers of the described optoelectronic devices are formed from solutions comprising of non-polymeric discrete organic materials.

In one embodiment, the invention embraces compounds of Formula I:

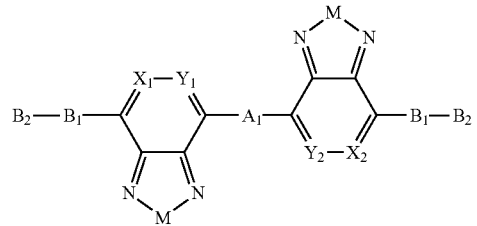

Formula I and, in additional embodiments, compounds of Formula Ia, Formula Ib, and Formula Ic:

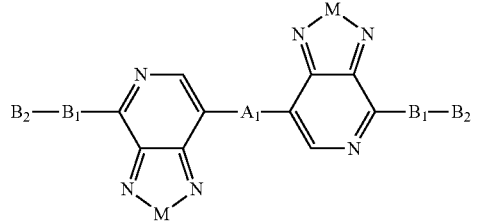

Ia

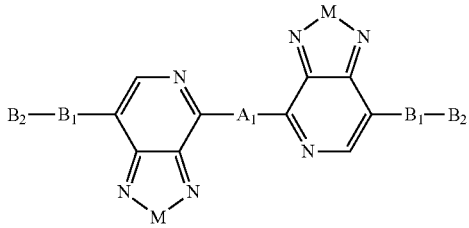

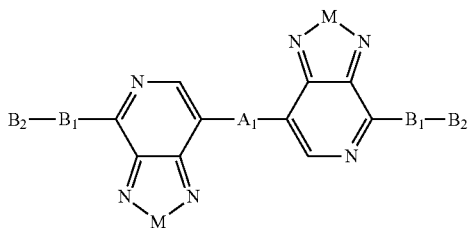

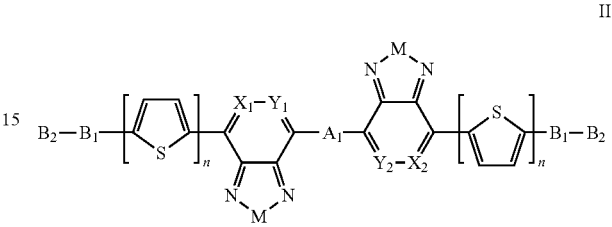

where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$ and $Y_2$ are selected from N and CH, where when $X_2$ is N, $Y_2$ is CH, and when $X_2$ is CH, $Y_2$ is N;

M is selected from sulfur (S), oxygen (O), or N—$R_1$, where $R_1$ is H, $C_1$-$C_{30}$ alkyl or $C_6$-$C_{30}$ aryl;

$A_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, di thienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $B_1$ is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{30}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole.

Each $B_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In another embodiment, the invention embraces compounds of Formula II:

where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$ and $Y_2$ are selected from N and CH, where when $X_2$ is N, $Y_2$ is CH, and when $X_2$ is CH, $Y_2$ is N;

M is selected from sulfur (S), oxygen (O), or N—$R_1$, where $R_1$ is H, $C_1$-$C_{30}$ alkyl or $C_6$-$C_{30}$ aryl;

n is an integer between 0 and 5, inclusive;

$A_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $B_1$ is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and each $B_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In one embodiment, n is an integer between 0 and 5, inclusive. In another embodiment, n is 0. In another embodiment, n is 1. In another embodiment, n is 2. In another embodiment, n is 3. In another embodiment, n is 4. In another embodiment, n is 5.

In some embodiments of Formula II, $X_1$ and $X_2$ are each N and $Y_1$ and $Y_2$ are each CH. In some embodiments of Formula II, $X_1$ and $X_2$ are each CH and $Y_1$ and $Y_2$ are each N.

In some embodiments of Formula II, $X_1$ and $X_2$ are each N, $Y_1$ and $Y_2$ are each CH and each M is S. In some embodiments of Formula II, $X_1$ and $X_2$ are each CH, $Y_1$ and $Y_2$ are each N, and each M is S.

In some embodiments of Formula II, $X_1$ and $X_2$ are each N, $Y_1$ and $Y_2$ are each CH and each M is O. In some embodiments of Formula II, $X_1$ and $X_2$ are each CH, $Y_1$ and $Y_2$ are each N, and each M is O.

In preferred embodiments, $B_2$ is selected from the group consisting of a nonentity, H, F, a $C_1$-$C_{16}$ alkyl group, thiophene, benzothiophene, benzofuran, and benzothiazole.

In further embodiments, $B_2$ is phenyl, substituted at the p-position with diphenylamine (i.e., the $B_2$ moiety is triphenylamine)

In another embodiment, the invention embraces compounds of Formula II of Formula IIa, Formula IIb, or Formula IIc:

IIa

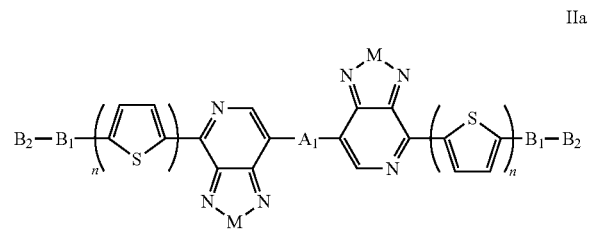

IIb

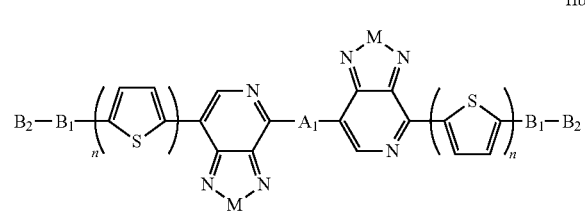

IIc

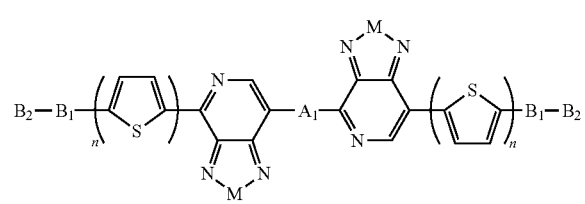

M is selected from sulfur (S), oxygen (O), or N—$R_1$, where $R_1$ is H, $C_1$-$C_{30}$ alkyl or $C_6$-$C_{30}$ aryl;

n is an integer between and 5, inclusive;

$A_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'-RR'-cyclopeta[2,1-b:3,4-b']-dithiophene, where R and R'=$C_1$-$C_{30}$ alkyl or $C_6$-$C_{30}$ aryl;

each $B_1$ is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and each $B_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In one embodiment, n is an integer between 0 and 5, inclusive. In another embodiment, n is 0. In another embodiment, n is 1. In another embodiment, n is 2. In another embodiment, n is 3. In another embodiment, n is 4. In another embodiment, n is 5.

In some embodiments of Formula IIa, each M is S.

In some embodiments of Formula IIa, each M is O.

In some embodiments of Formula IIb, each M is S.

In some embodiments of Formula IIb, each M is O.

In some embodiments of Formula IIc, each M is S.

In some embodiments of Formula IIc, each M is O.

In some embodiments, the compounds of Formula II are selected from compounds of Formula IId:

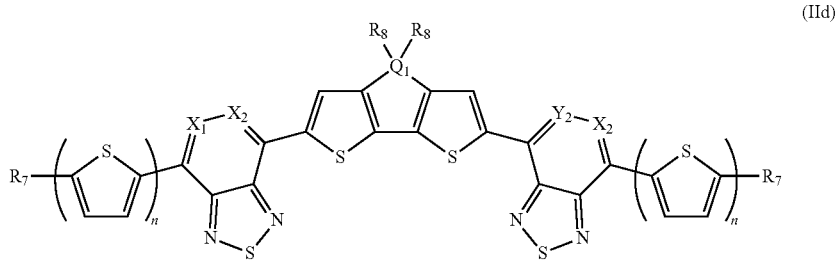

(IId)

where $Q_1$ is C or Si;
where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$ and $Y_2$ are selected from N and CH, where when $X_2$ is N, $Y_2$ is CH, and when $X_2$ is CH, $Y_2$ is N;
n is 0, 1, 2, or 3;
$R_7$ is selected from H, $C_1$-$C_{16}$ alkyl, —O—$C_1$-$C_{16}$ alkyl, benzofuran-2-yl, benzothiophene-2-yl, and benzothiazole-2-yl; and
$R_8$ is selected from H, $C_1$-$C_{16}$ alkyl or —O—$C_1$-$C_{16}$ alkyl.

In one embodiment of Formula IId, $Q_1$ is C.
In one embodiment of Formula IId, $Q_1$ is Si.
In one embodiment of Formula IId, $X_1$ and $X_2$ are N and $Y_1$ and $Y_2$ are CH.
In one embodiment of Formula IId, $X_1$ and $X_2$ are CH and $Y_1$ and $Y_2$ are N.
In one embodiment of Formula IId, n is 2.
In one embodiment of Formula IId, $R_7$ is selected from H or $C_1$-$C_{16}$ alkyl.
In one embodiment of Formula IId, $R_7$ is selected from benzofuran-2-yl.
In one embodiment of Formula IId, $R_7$ is selected from benzothiophene-2-yl.
In one embodiment of Formula IId, $R_7$ is selected from benzothiazole-2-yl.
In one embodiment of Formula IId, $R_8$ is selected from H or $C_1$-$C_{16}$ alkyl.
In one embodiment of Formula IId, $R_8$ is selected from $C_1$-$C_{16}$ alkyl.
In one embodiment of Formula IId, $Q_1$ is C, $X_1$ and $X_2$ are N, and $Y_1$ and $Y_2$ are CH.
In one embodiment of Formula IId, $Q_1$ is C, $X_1$ and $X_2$ are CH, and $Y_1$ and $Y_2$ are N.
In one embodiment of Formula IId, $Q_1$ is Si, $X_1$ and $X_2$ are N, and $Y_1$ and $Y_2$ are CH.
In one embodiment of Formula IId, $Q_1$ is Si, $X_1$ and $X_2$ are CH, and $Y_1$ and $Y_2$ are N.
In one embodiment of Formula IId, $Q_1$ is C, $X_1$ and $X_2$ are $Y_1$ d $Y_2$ are CH, and n is 1.
In one embodiment of Formula IId, $Q_1$ is C, $X_1$ and $X_2$ are CH, $Y_1$ and $Y_2$ are N, and n is 1.
In one embodiment of Formula IId, $Q_1$ is Si, $X_1$ and $X_2$ are N, $Y_1$ and $Y_2$ are CH, and n is 1.
In one embodiment of Formula IId, $Q_1$ is Si, $X_1$ and $X_2$ are CH, $Y_1$ and $Y_2$ are N, and n is 1.
In one embodiment of Formula IId, $Q_1$ is C, $X_1$ and $X_2$ are N, $Y_1$ and $Y_2$ are CH, n is 1, and $R_7$ is n-hexyl.
In one embodiment of Formula IId, $Q_1$ is C, $X_1$ and $X_2$ are CH, $Y_1$ and $Y_2$ are N, n is 1, and $R_7$ is n-hexyl.
In one embodiment of Formula IId, $Q_1$ is Si, $X_1$ and $X_2$ are N, $Y_1$ and $Y_2$ are CH, n is 1, and $R_7$ is n-hexyl.
In one embodiment of Formula IId, $Q_1$ is Si, $X_1$ and $X_2$ are CH, $Y_1$ and $Y_2$ are N, n is 1, and $R_7$ is n-hexyl.
In one embodiment of Formula IId, $Q_1$ is C, $X_1$ and $X_2$ are N, $Y_1$ and $Y_2$ are CH, n is 1, and $R_8$ is 2-ethyl-hexyl.
In one embodiment of Formula IId, $Q_1$ is C, $X_1$ and $X_2$ are CH, $Y_1$ and $Y_2$ are N, n is 1, and $R_8$ is 2-ethyl-hexyl.
In one embodiment of Formula IId, $Q_1$ is Si, $X_1$ and $X_2$ are N, $Y_1$ and $Y_2$ are CH, n is 1, and $R_8$ is 2-ethyl-hexyl.
In one embodiment of Formula IId, $Q_1$ is Si, $X_1$ and $X_2$ are CH, $Y_1$ and $Y_2$ are N, n is 1, and $R_8$ is 2-ethyl-hexyl.
In one embodiment of Formula IId, $Q_1$ is C, $X_1$ and $X_2$ are N, $Y_1$ and $Y_2$ are CH, and n is 2.
In one embodiment of Formula IId, $Q_1$ is C, $X_1$ and $X_2$ are CH, $Y_1$ and $Y_2$ are N, and n is 2.
In one embodiment of Formula IId, $Q_1$ is Si, $X_1$ and $X_2$ are N, $Y_1$ and $Y_2$ are CH, and n is 2.
In one embodiment of Formula IId, $Q_1$ is Si, $X_1$ and $X_2$ are CH, $Y_1$ and $Y_2$ are N, and n is 2.
In one embodiment of Formula IId, $Q_1$ is C, $X_1$ and $X_2$ are N, $Y_1$ and $Y_2$ are CH, n is 2, and $R_7$ is n-hexyl.
In one embodiment of Formula IId, $Q_1$ is C, $X_1$ and $X_2$ are CH, $Y_1$ and $Y_2$ are N, n is 2, and $R_7$ is n-hexyl.
In one embodiment of Formula IId, $Q_1$ is Si, $X_1$ and $X_2$ are N, $Y_1$ and $Y_2$ are CH, n is 2, and $R_7$ is n-hexyl.
In one embodiment of Formula IId, $Q_1$ is Si, $X_1$ and $X_2$ are CH, $Y_1$ and $Y_2$ are N, n is 2, and $R_7$ is n-hexyl.
In one embodiment of Formula IId, $Q_1$ is C, $X_1$ and $X_2$ are N, $Y_1$ and $Y_2$ are CH, n is 2, and $R_8$ is 2-ethyl-hexyl.
In one embodiment of Formula IId, $Q_1$ is C, $X_1$ and $X_2$ are CH, $Y_1$ and $Y_2$ are N, n is 2, and $R_8$ is 2-ethyl-hexyl.
In one embodiment of Formula IId, $Q_1$ is Si, $X_1$ and $X_2$ are N, $Y_1$ and $Y_2$ are CH, n is 2, and $R_8$ is 2-ethyl-hexyl.
In one embodiment of Formula IId, $Q_1$ is Si, $X_1$ and $X_2$ are CH, $Y_1$ and $Y_2$ are N, n is 2, and $R_8$ is 2-ethyl-hexyl.
In one embodiment of Formula IId, is $Q_1$ is C, $X_1$ and $X_2$ are N, $Y_1$ and $Y_2$ are CH, and n is 3.
In one embodiment of Formula IId, $Q_1$ is C, $X_1$ and $X_2$ are CH, $Y_1$ and $Y_2$ are N, and n is 3.
In one embodiment of Formula IId, $Q_1$ is Si, $X_1$ and $X_2$ are N, $Y_1$ and $Y_2$ are CH, and n is 3.
In one embodiment of Formula IId, $Q_1$ is Si, $X_1$ and $X_2$ are CH, $Y_1$ and $Y_2$ are N, and n is 3.
In one embodiment of Formula IId, $Q_1$ is C. $X_1$ and $X_2$ are N, $Y_1$ and $Y_2$ are CH, n is 3, and $R_7$ is n-hexyl.
In one embodiment of Formula IId, $Q_1$ is C, $X_1$ and $X_2$ are CH, $Y_1$ and $Y_2$ are N, n is 3, and $R_7$ is n-hexyl.
In one embodiment of Formula IId, $Q_1$ is Si, $X_1$ and $X_2$ are N, $Y_1$ and $Y_2$ are CH, n is 3, and $R_7$ is n-hexyl.
In one embodiment of Formula IId, $Q_1$ is Si, $X_1$ and $X_2$ are CH, $Y_1$ and $Y_2$ are N, n is 3, and $R_7$ is n-hexyl.
In one embodiment of Formula IId, $Q_1$ is C, $X_1$ and $X_2$ are N, $Y_1$ and $Y_2$ are CH, n is 3, and $R_8$ is 2-ethyl-hexyl.

In one embodiment of Formula IId, $Q_1$ is C, $X_1$ and $X_2$ are CH, $Y_1$ and $Y_2$ are N, n is 3, and $R_8$ is 2-ethyl-hexyl.

In one embodiment of Formula IId, $Q_1$ is Si, $X_1$ and $X_2$ are N, $Y_1$ and $Y_2$ are CH, n is 3, and $R_8$ is 2-ethyl-hexyl.

In one embodiment of Formula IId, $Q_1$ is Si, $X_1$ and $X_2$ are CH, $Y_1$ and $Y_2$ are N, n is 3, and $R_8$ is 2-ethyl-hexyl.

In one embodiment of Formula IId, $Q_1$ is C, $X_1$ and $X_2$ are N, $Y_1$ and $Y_2$ are CH, n is 3, and $R_8$ is n-hexyl.

In one embodiment of Formula IId, $Q_1$ is C, $X_1$ and $X_2$ are CH, $Y_1$ and $Y_2$ are N, n is 3, and $R_8$ is n-hexyl.

In one embodiment of Formula IId, $Q_1$ is Si, $X_1$ and $X_2$ are N, $Y_1$ and $Y_2$ are CH, n is 3, and $R_8$ is n-hexyl.

In one embodiment of Formula IId, $Q_1$ is Si, $X_1$ and $X_2$ are CH, $Y_1$ and $Y_2$ are N, n is 3, and $R_8$ is n-hexyl.

In one embodiment of Formula IId, the compound is of the formula:

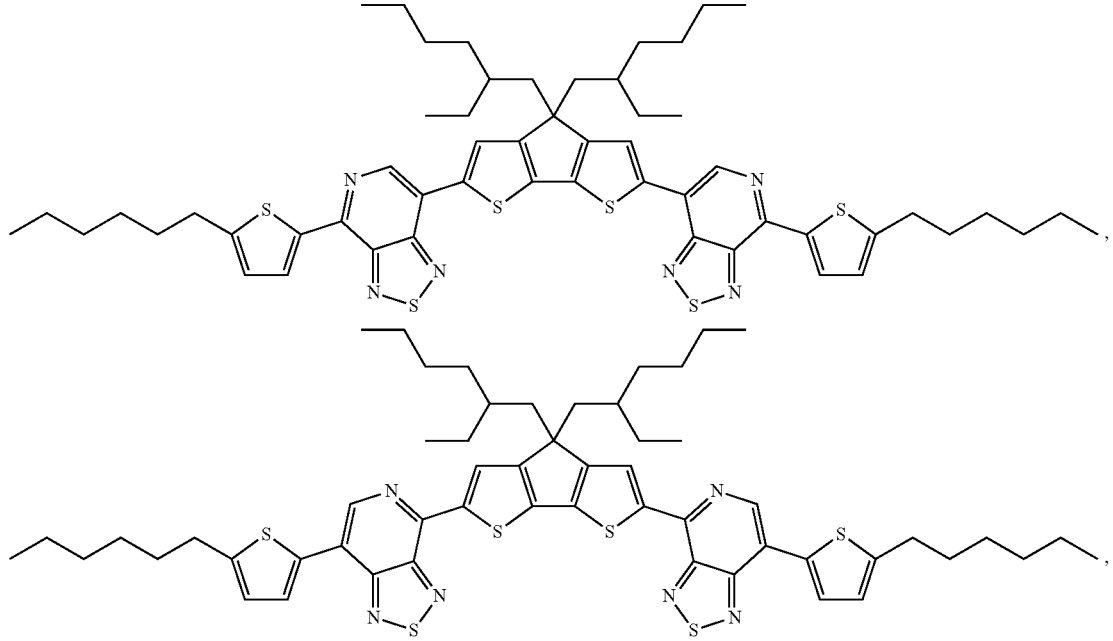

,

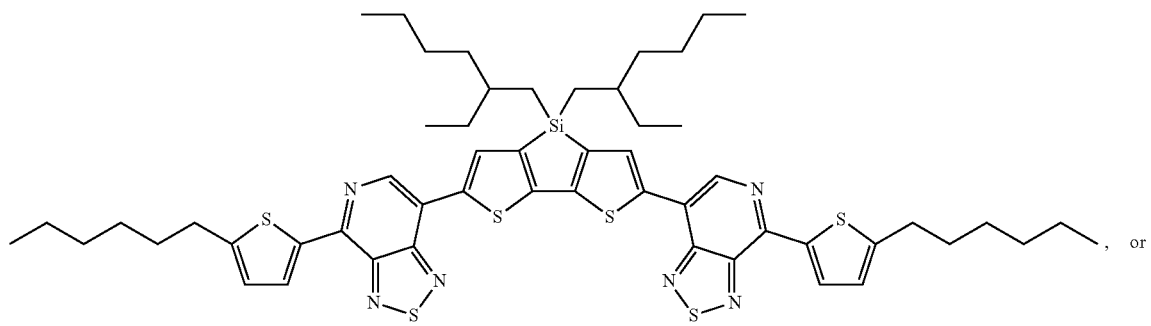

, or

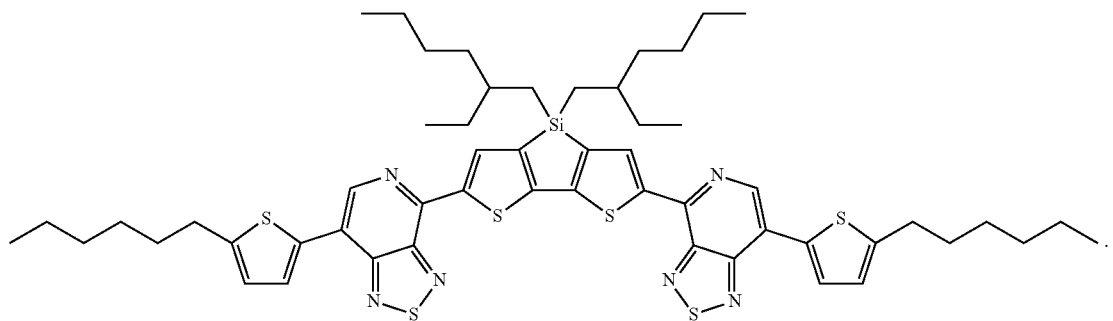

.

In one embodiment of Formula IId, the compound is of the formula:
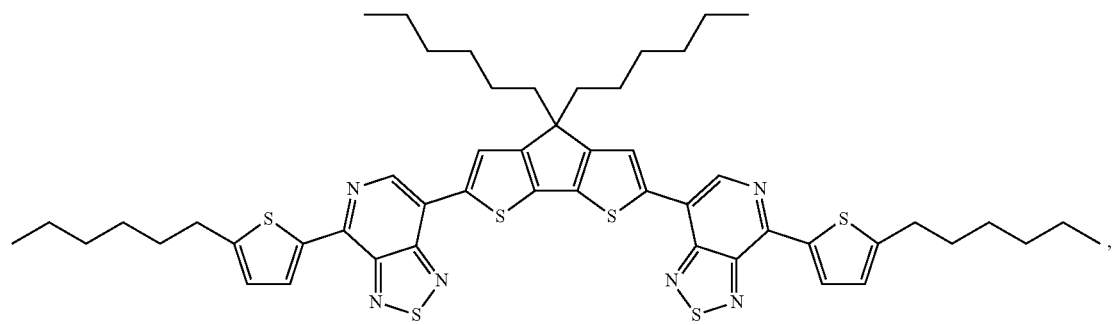
,
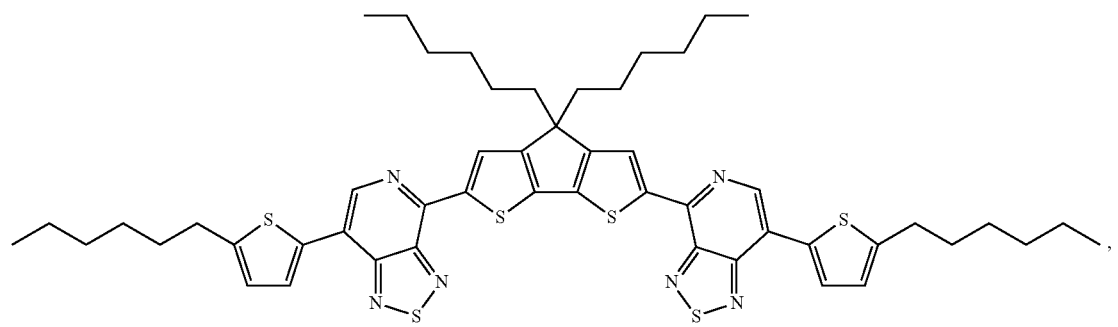
,
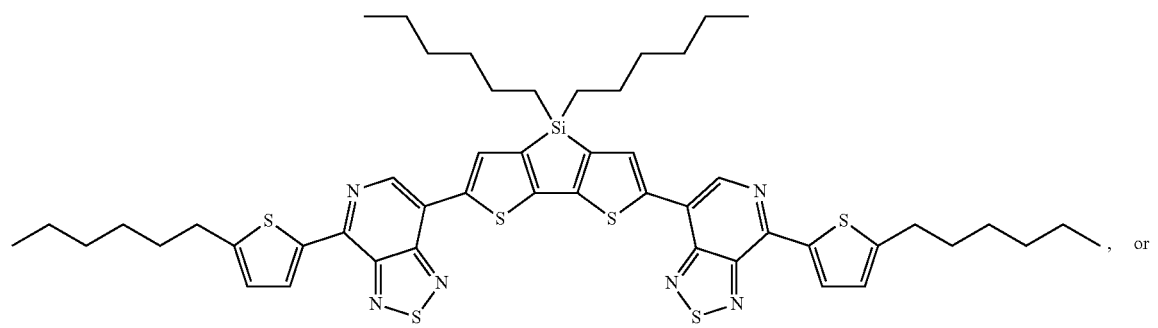
, or
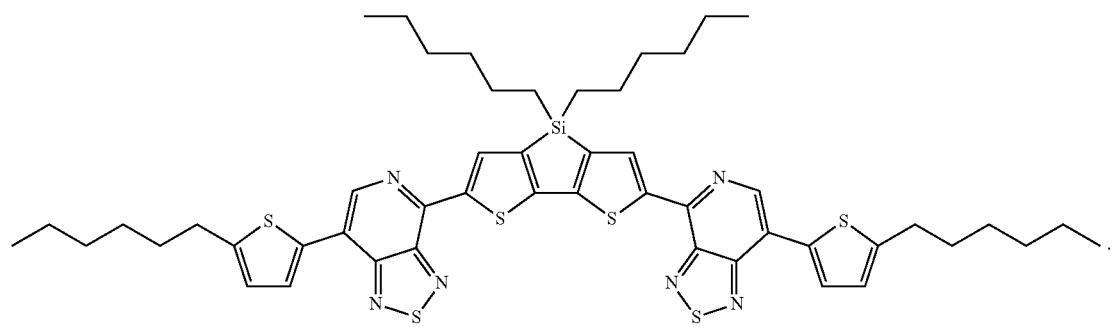
.

In one embodiment of Formula IId, the compound is of the formula:
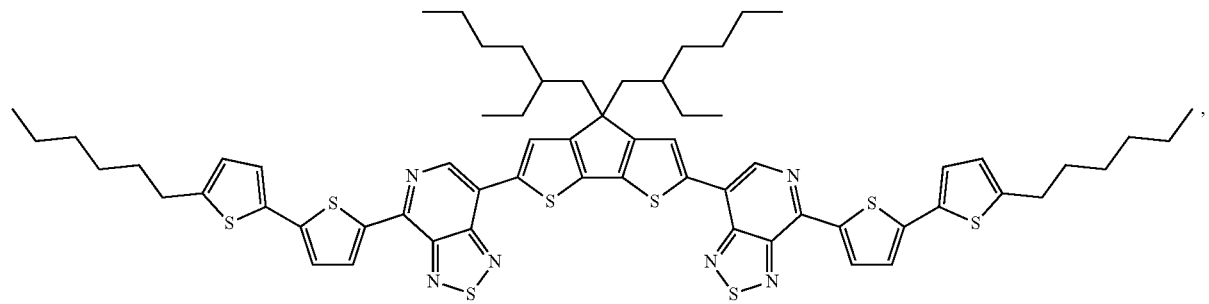
(G9)
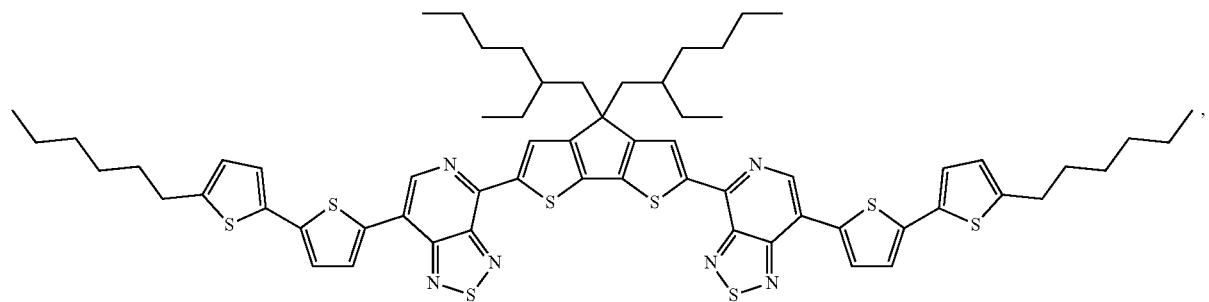
(G24)
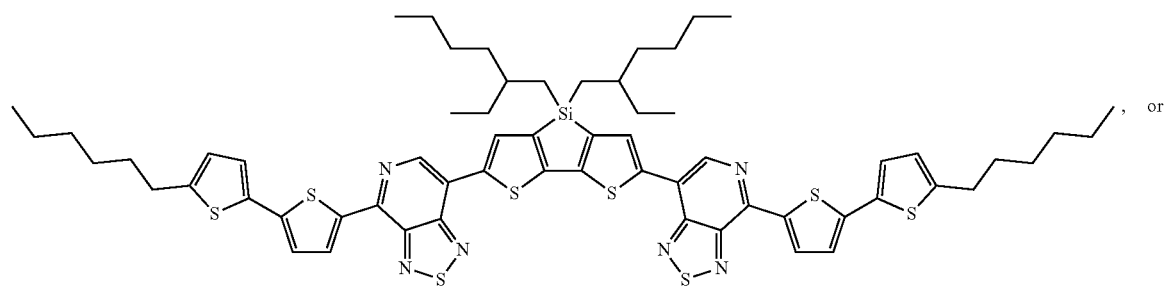
, or
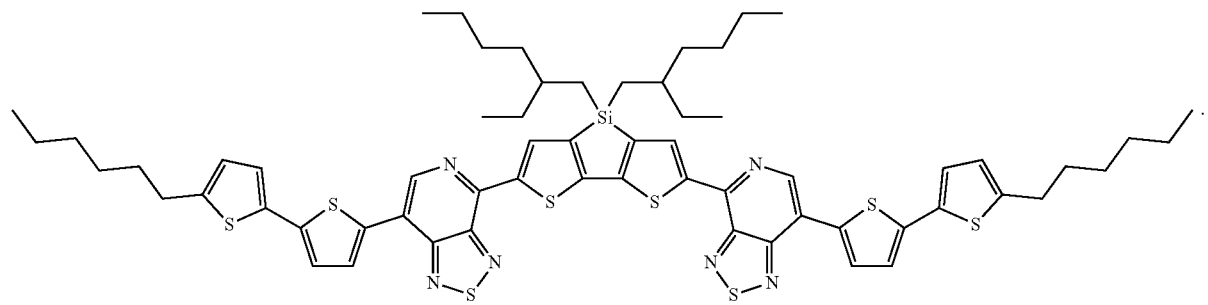
(G116)

In one embodiment of Formula IId, the compound is of the formula:
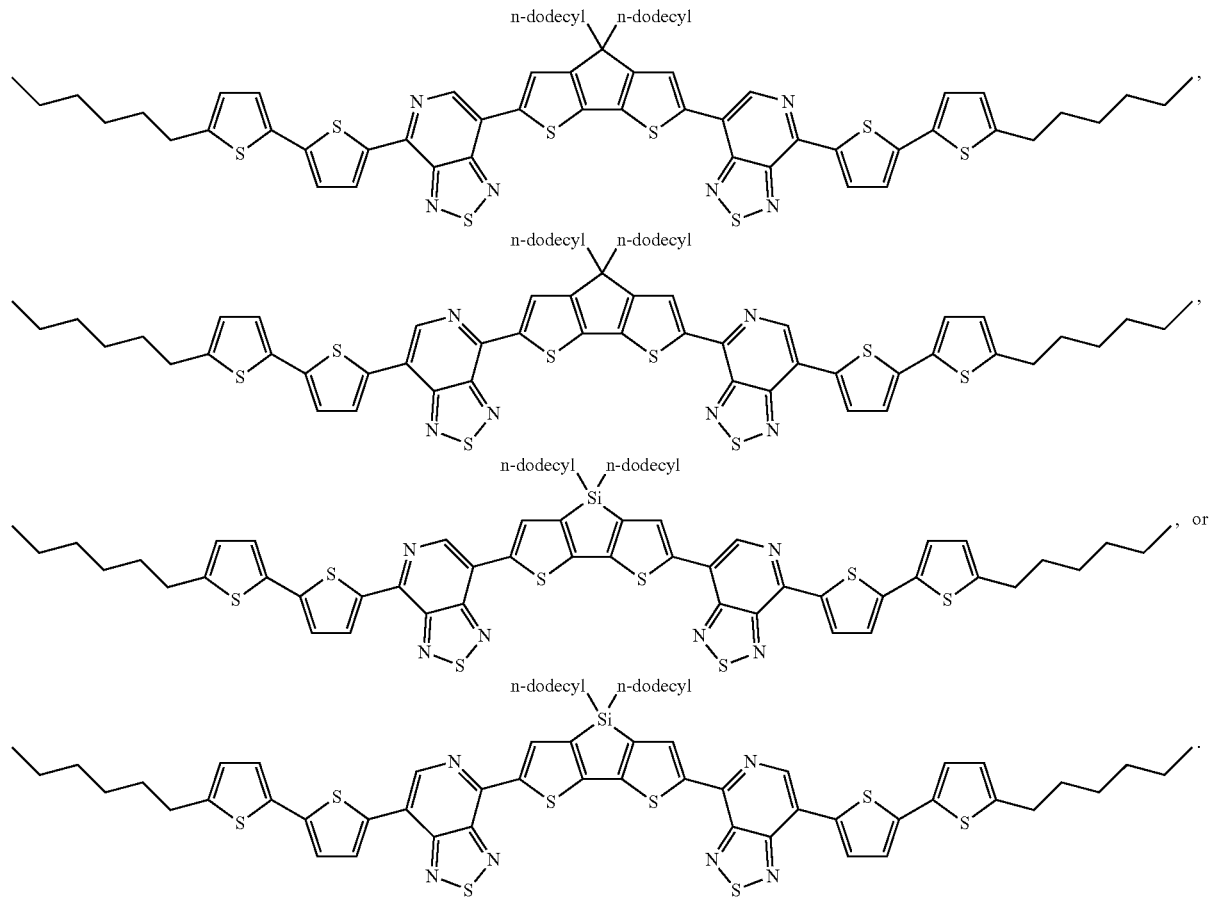
In one embodiment of Formula IId, the compound is of the formula:
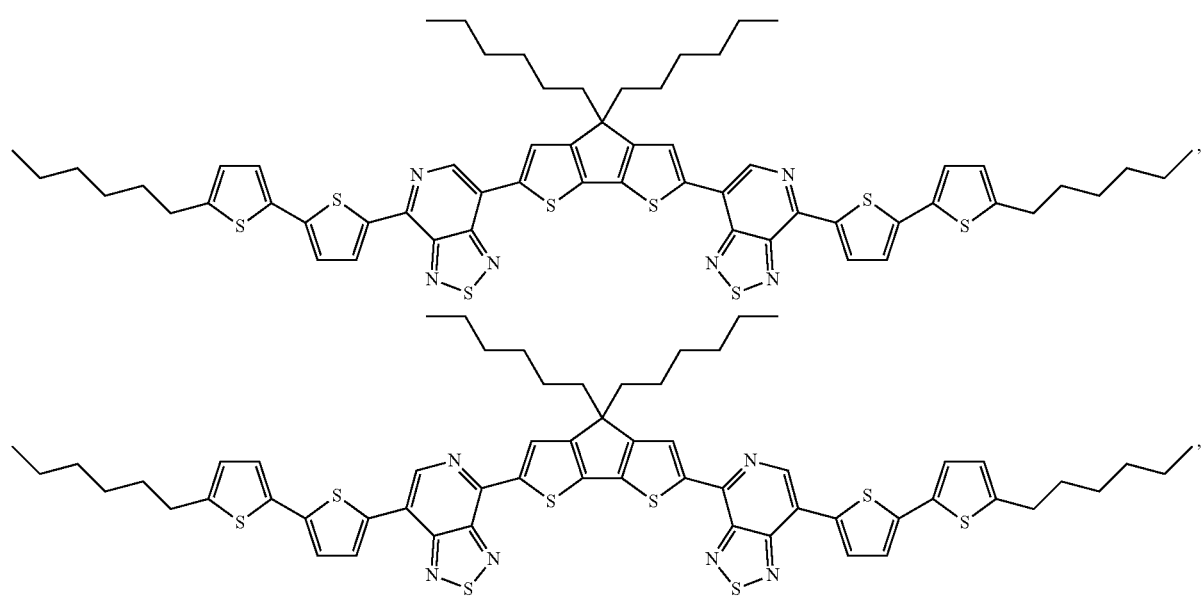

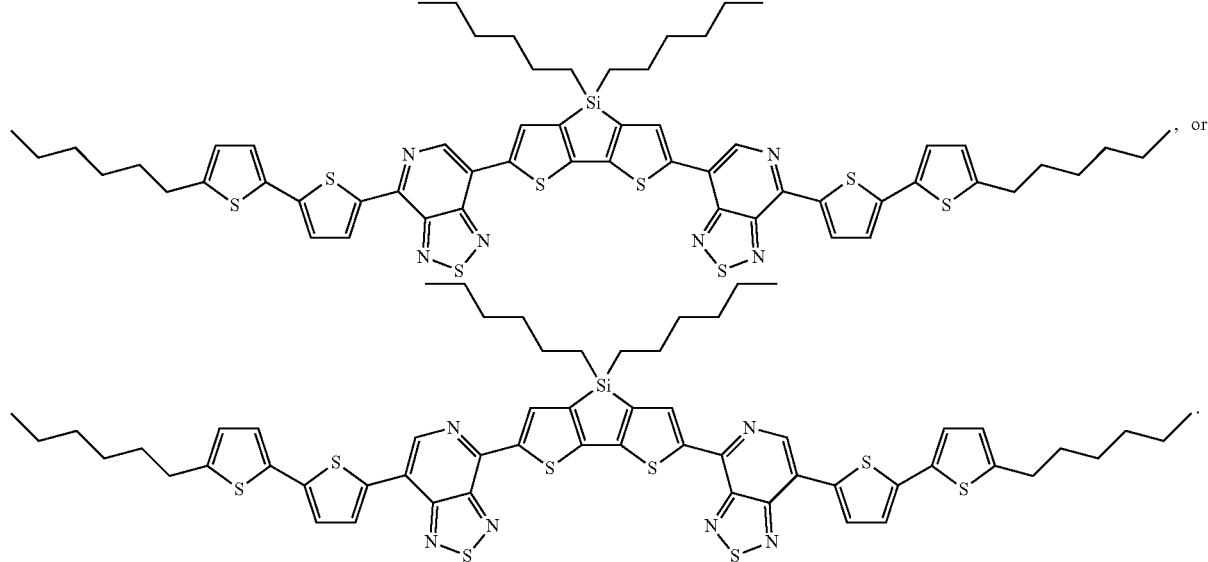
In one embodiment of Formula IId, the compound is of the formula:
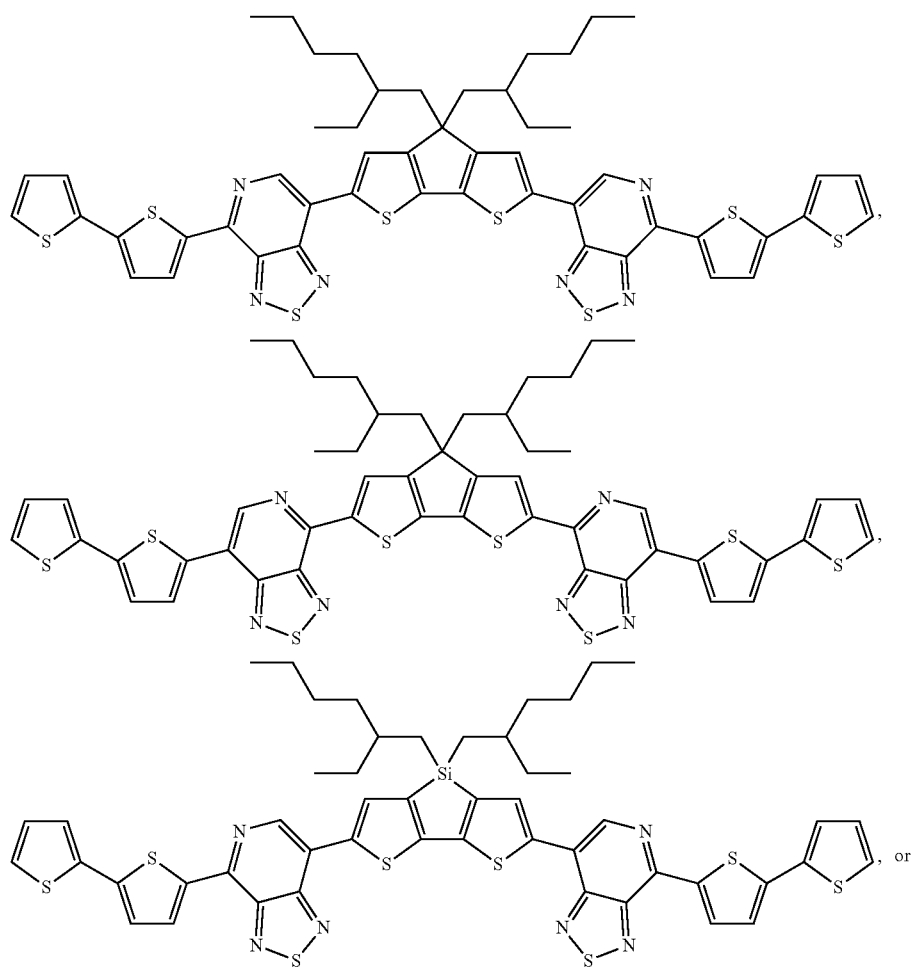

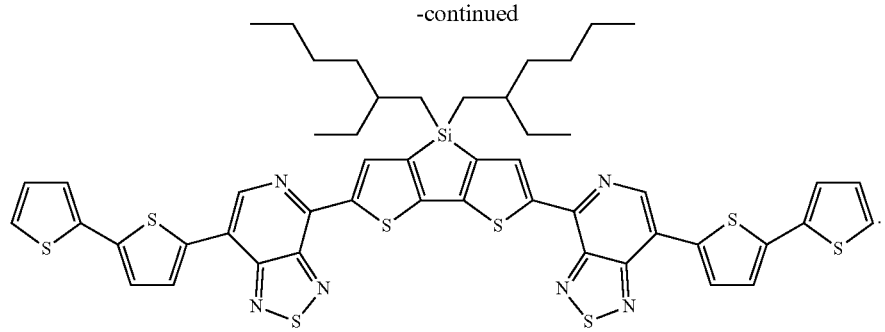
In one embodiment of Formula IId, the compound is of the formula:
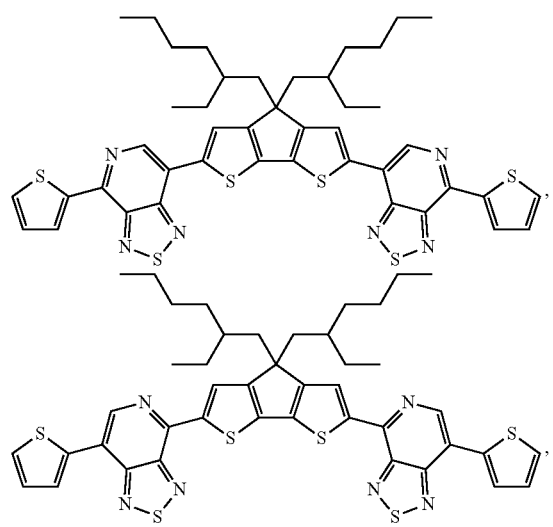
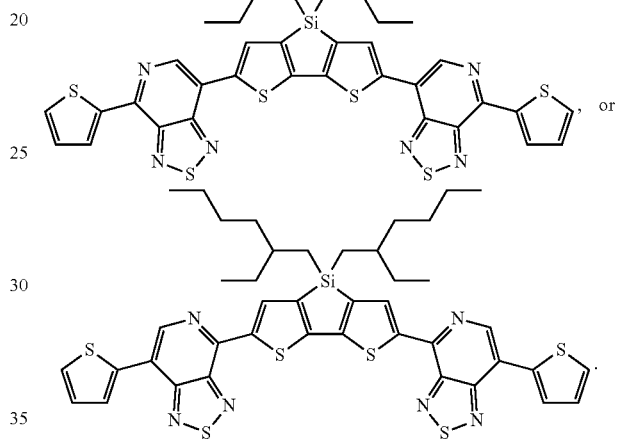
In one embodiment of Formula IId, the compound is of the formula:
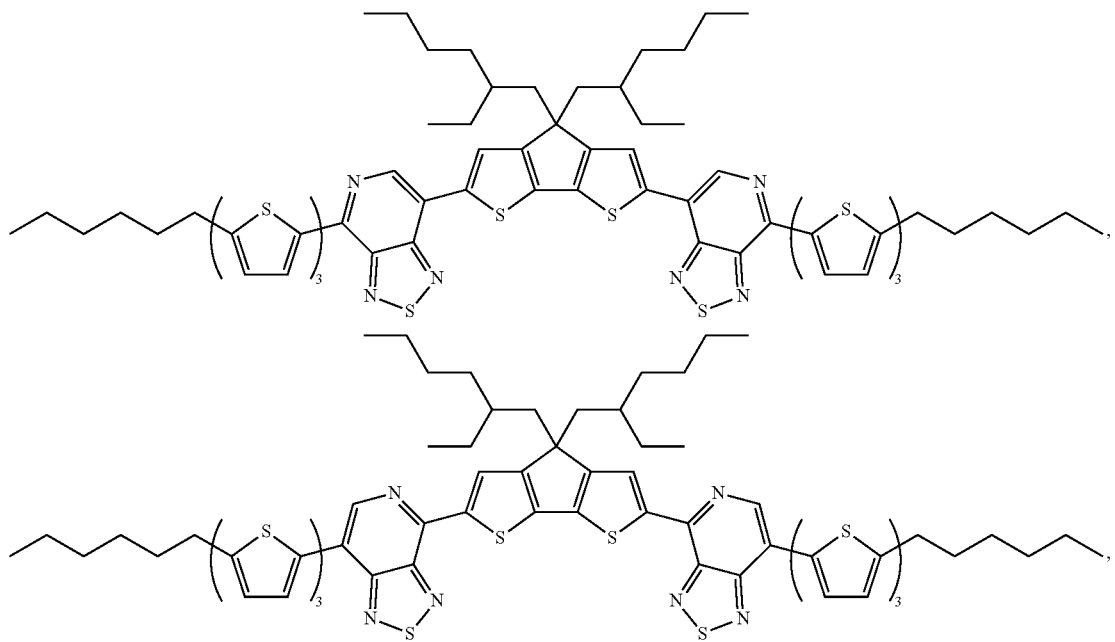

-continued
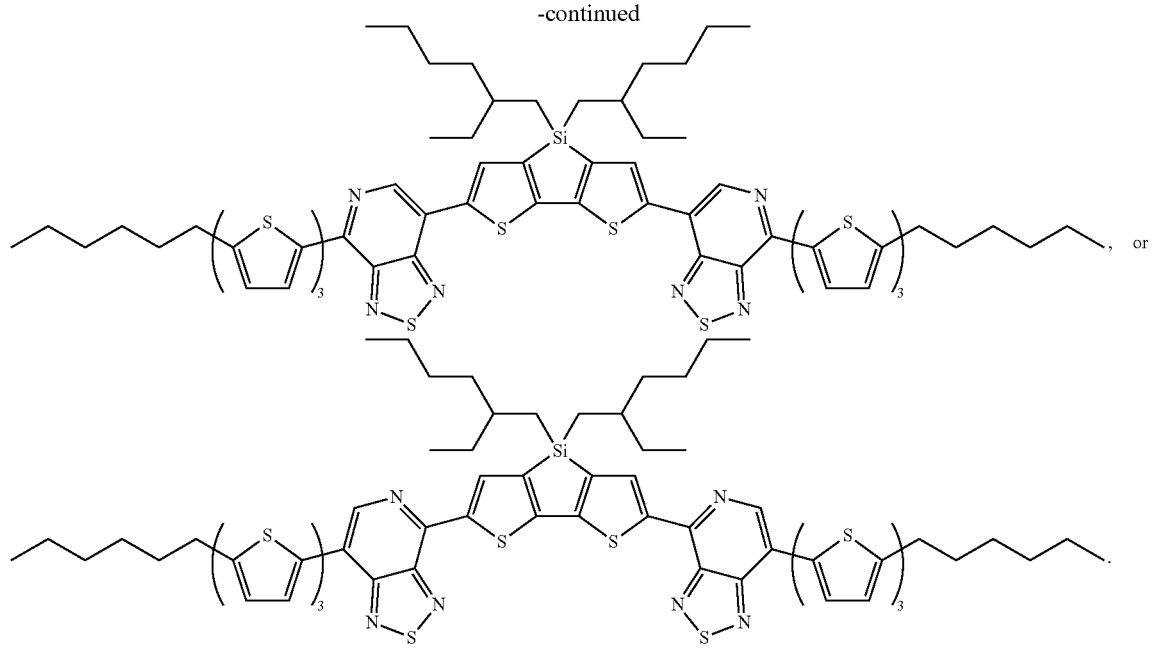
In one embodiment of Formula IId, the compound is of the formula:
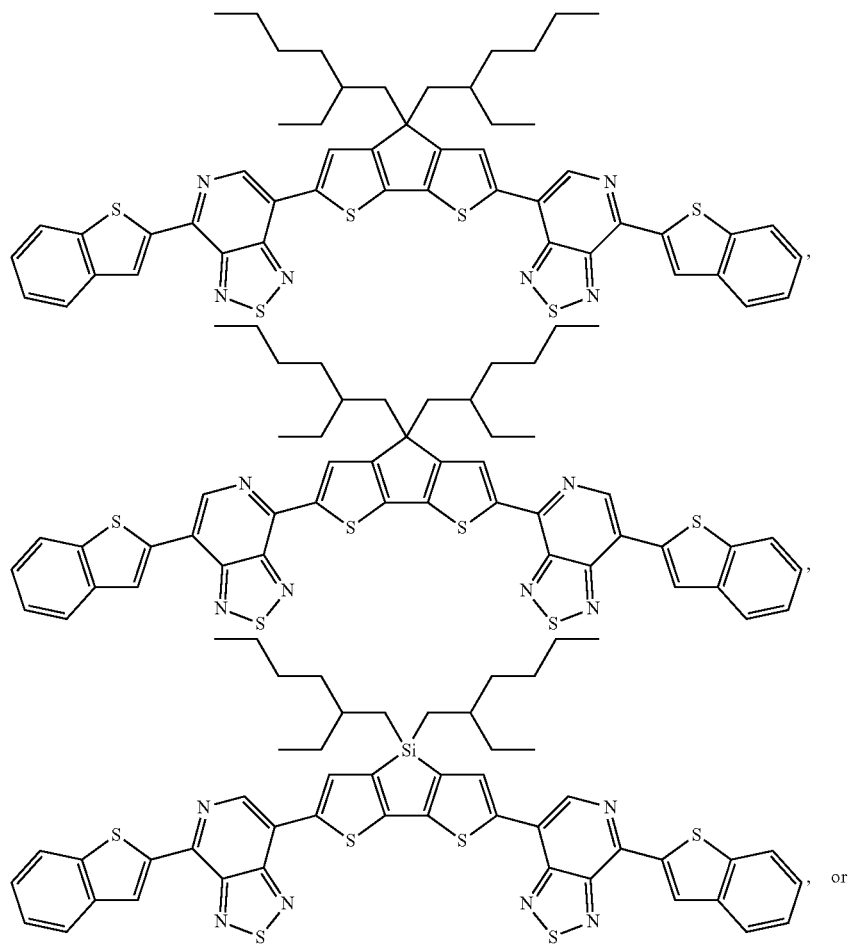

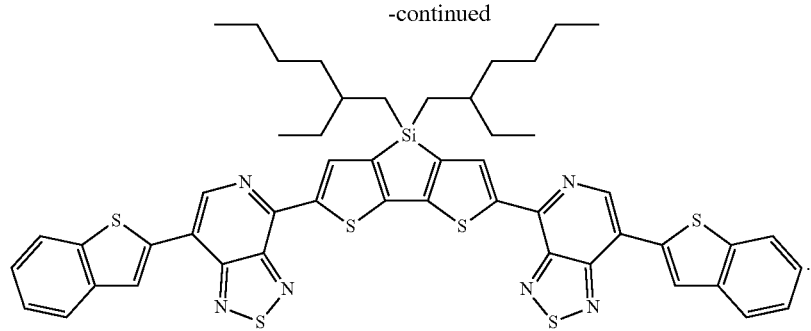
In one embodiment of Formula IId, the compound is of the formula:
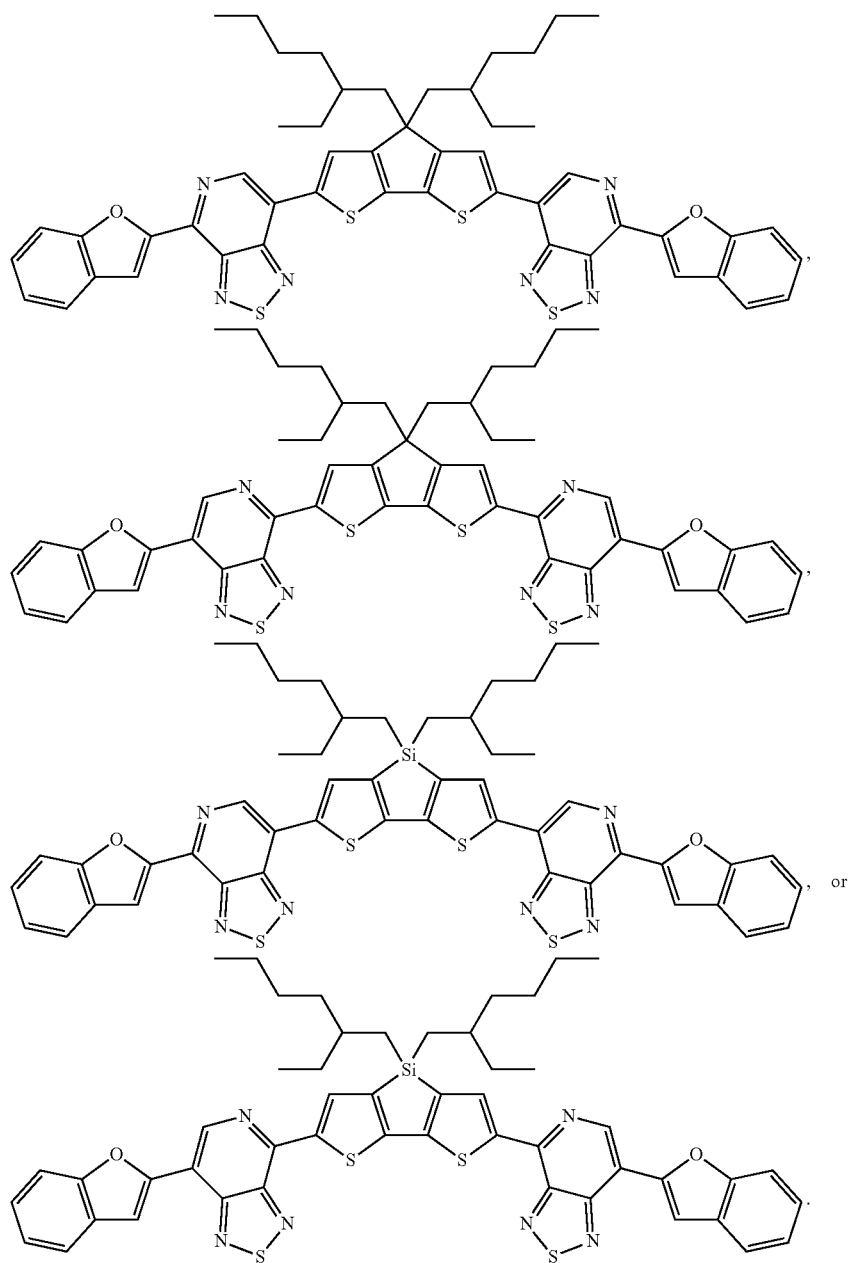

In one embodiment of Formula IId, the compound is of the formula:
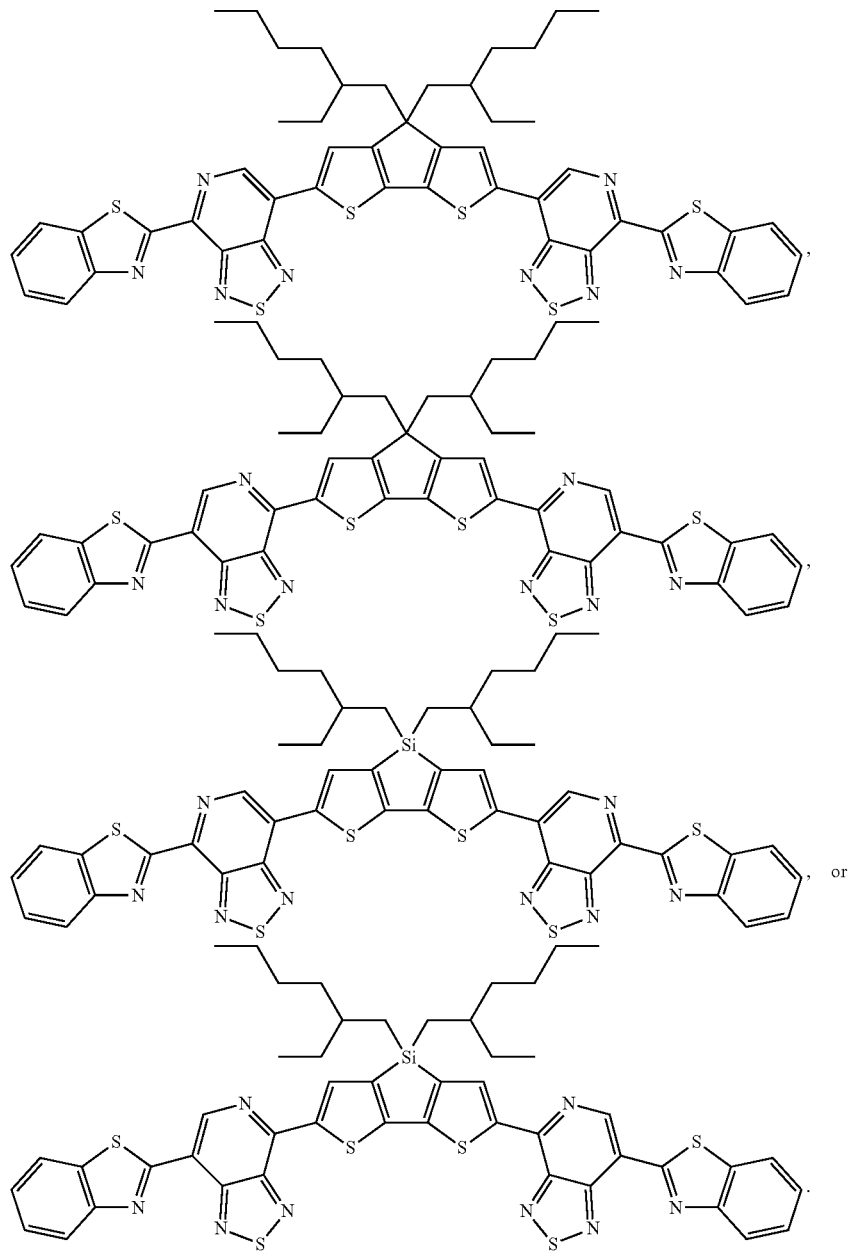
In some embodiments of Formula II the compounds are of Formula IIe:
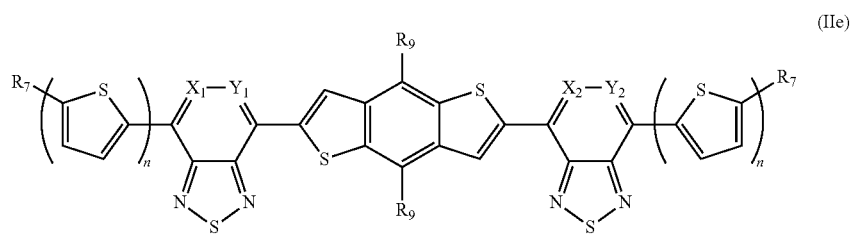
(IIe)

where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$ and $Y_2$, are selected from N and CH, where when $X_2$ is N, $Y_2$ is CH, and when $X_2$ is CH, $Y_2$ is N;

n is 0, 1, 2, or 3;

$R_7$ is selected from H, $C_1$-$C_{16}$ alkyl, —O—$C_1$-$C_{16}$ alkyl, benzofuran-2-yl, benzothiophene-2-yl, benzothiazole-2-yl, 4H-cyclopenta[2,1-b;3,4-b']dithiophene-2-yl, 4,4-bis($C_1$-$C_{16}$ alkyl)-4H-cyclopenta[2,1-b;3,4-b']dithiophene-2-yl, and 4,4-bis(2-ethylhexyl)-4H-cyclopenta[2,1-b:3,4-b']dithiophene-2-yl; and $R_9$ is selected from H, $C_1$-$C_{16}$ alkyl or —O—$C_1$-$C_{16}$ alkyl.

In one embodiment of Formula IIe, n is 0.
In one embodiment of Formula IIe, n is 1.
In one embodiment of Formula IIe, n is 2.
In one embodiment of Formula IIe, n is 3.
In one embodiment of Formula IIe, $X_1$ and $X_2$ are N and $Y_1$ and $Y_2$ are CH.
In one embodiment of Formula IIe, $X_1$ and $X_2$ are CH and $Y_1$ and $Y_2$ are N.
In one embodiment of Formula IIe, $R_9$ is —O—$C_1$-$C_{16}$ alkyl.
In one embodiment of Formula IIe, $R_9$ is —O—$CH_2CH(C_2H_5)(C_4H_9)$.
In one embodiment of Formula IIe, $R_7$ is 4,4-bis(2-ethylhexyl)-4H-cyclopenta[2,1-b;3,4-b']dithiophene-2-yl.
In one embodiment of Formula IIe, $R_9$ is —O—$CH_2CH(C_2H_5)(C_4H_9)$ and $R_7$ is 4,4-bis(2-ethylhexyl)-4H-cyclopenta[2,1-b;3,4-b']dithiophene-2-yl.
In one embodiment of Formula IIe, $R_9$ is —O—$C_1$-$C_{16}$ alkyl and n is 0.
In one embodiment of Formula IIe, $R_9$ is —O—$CH_2CH(C_2H_5)(C_4H_9)$ and n is 0.
In one embodiment of Formula IIe, $R_7$ is 4,4-bis(2-ethylhexyl)-4H-cyclopenta[2,1-b;3,4-b']dithiophene-2-yl and n is 0.
In one embodiment of Formula IIe, $R_9$ is —O—$CH_2CH(C_2H_5)(C_4H_9)$, $R_7$ is 4,4-bis(2-ethylhexyl)-4H-cyclopenta[2,1-b;3,4-b']dithiophene-2-yl and n is 0.
In one embodiment of Formula IIe, $R_9$ is —O—$CH_2CH(C_2H_5)(C_4H_9)$, $R_7$ is 4,4-bis(2-ethylhexyl)-4H-cyclopenta[2,1-b;3,4-b']dithiophene-2-yl, $X_1$ and $X_2$ are N, and $Y_1$ and $Y_2$ are CH.
In one embodiment of Formula IIe, $R_9$ is —O—$CH_2CH(C_2H_5)(C_4H_9)$, $R_7$ is 4,4-bis(2-ethylhexyl)-4H-cyclopenta[2,1-b;3,4-b']dithiophene-2-yl, $X_1$ and $X_2$ are CH, and $Y_1$ and $Y_2$ are N.
In one embodiment of Formula IIe, $R_9$ is —O—$CH_2CH(C_2H_5)(C_4H_9)$, $R_7$ is 4,4-bis(2-ethylhexyl)-4H-cyclopenta[2,1-b;3,4-b']dithiophene-2-yl, $X_1$ and $X_2$ are N, $Y_1$ and $Y_2$ are CH, and n is 0.
In one embodiment of Formula IIe, $R_9$ is —O—$CH_2CH(C_2H_5)(C_4H_9)$, $R_7$ is 4,4-bis(2-ethylhexyl)-4H-cyclopenta[2,1-b;3,4-b']dithiophene-2-yl, $X_1$ and $X_2$ are CH, $Y_1$ and $Y_2$ are N, and n is 0.
In one embodiment of Formula IIe, $R_7$ is n-hexyl.
In one embodiment of Formula IIe, $R_9$ is —O—$C_1$-$C_{16}$ alkyl and n is 1.
In one embodiment of Formula IIe, $R_9$ is —O—$CH_2CH(C_2H_5)(C_4H_9)$ and n is 1.
In one embodiment of Formula IIe, $R_9$ is —O—$CH_2CH(C_2H_5)(C_4H_9)$ and $R_7$ is n-hexyl.
In one embodiment of Formula IIe, $R_7$ is n-hexyl and n is 1.
In one embodiment of Formula IIe, $R_9$ is —O—$CH_2CH(C_2H_5)(C_4H_9)$, $R_7$ is n-hexyl and n is 1.
In one embodiment of Formula IIe, $R_9$ is —O—$CH_2CH(C_2H_5)(C_4H_9)$, $R_7$ is n-hexyl, $X_1$ and $X_2$ are N, and $Y_1$ and $Y_2$ are CH.
In one embodiment of Formula IIe, $R_9$ is —O—$CH_2CH(C_2H_5)(C_4H_9)$, $R_7$ is n-hexyl, $X_1$ and $X_2$ are CH, and $Y_1$ and $Y_2$ are N.
In one embodiment of Formula IIe, $R_9$ is —O—$CH_2CH(C_2H_5)(C_4H_9)$, $R_7$ is n-hexyl, $X_1$ and $X_2$ are N, $Y_1$ and $Y_2$ are CH, and n is 1.
In one embodiment of Formula IIe, $R_9$ is —O—$CH_2CH(C_2H_5)(C_4H_9)$, $R_7$ is n-hexyl, $X_1$ and $X_2$ are CH, $Y_1$ and $Y_2$ are N, and n is 1.

In some embodiments, the compounds of Formula II embrace compounds of Formula IIf:

(IIf)

where $R_9$ is H, $C_1$-$C_{16}$ alkyl or —O—$C_1$-$C_{16}$ alkyl.

In one embodiment of Formula IIf, $R_9$ is —O—$CH_2CH(C_2H_5)(C_4H_9)$.

In one embodiment of Formula IIf, $R_9$ is —O—$(CH_2)_5CH_3$.

In another embodiment, the invention embraces compounds of Formula III:

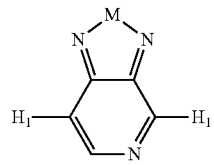

III where M is selected from sulfur (S), oxygen (O), or N—$R_1$, where $R_1$ is H, $C_1$-$C_{30}$ alkyl or $C_6$-$C_{30}$ aryl;

where $H_1$ is selected from $A_1$, —$B_1$—$B_2$, -$A_1$-$B_1$—$B_2$, or

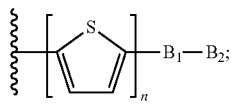

n is an integer between 0 and 5, inclusive;

$A_1$ (when present) is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, toluene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene-2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $B_1$ (when present) is independently selected from substituted or unsubstituted aryl or heteroaryl groups such as $C_6$-$C_{30}$ substituted or unsubstituted, aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole benzoxazole, benzoxadiazole, benzothiazole, benzimidazole, benzofuran, isobenzofuran, thiadiazole, perfluorylbenzene, and carbazole; and each $B_2$ (when present) is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In one embodiment, n is an integer between 0 and 5, inclusive. In another embodiment, n is 0. In another embodiment, n is 1. In another embodiment, n is 2. In another embodiment, n is 3. In another embodiment, n is 4. In another embodiment, n is 5.

In another embodiment, the invention embraces compounds of Formula III of Formula IIIa, Formula IIIb, Formula IIIc, and Formula IIId:

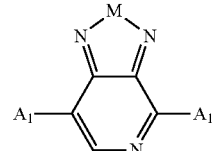

IIIa

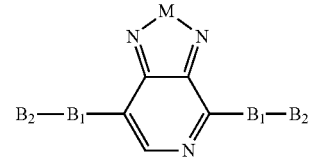

IIIb

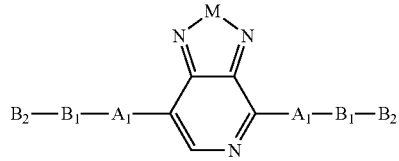

IIIc

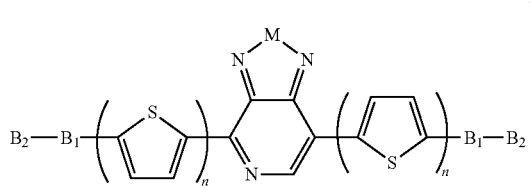

IIId where M is selected from sulfur (S), oxygen (O), or N—$R_1$, where $R_1$ is H, $C_1$-$C_{30}$ alkyl or $C_6$-$C_{30}$ aryl;

n is an integer between 0 and 5, inclusive;

$A_1$ (when present) is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$) substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, dithienopyrrole, dithienophosphole and carbazole 9,9-RR'-9H-fluorene, 9-R-9H-carbazole, 3,3'-RR'silylene 2,2'-bithiophene, 3,3'RR'-cyclopenta[2,1-b:3,4-b']-dithiophene, where R and R'=$C_1$-$C_{30}$ alkyl or $C_6$-$C_{30}$ aryl;

each $B_1$ (when present) is independently selected from substituted or unsubstituted aryl or heteroaryl groups such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of such groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and each $B_2$ (when present) is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups.

In one embodiment, n is an integer between 0 and 5, inclusive. In another embodiment, n is 0. In another embodiment, n is 1. In another embodiment, n is 2. In another embodiment, n is 3. In another embodiment, n is 4. In another embodiment, n is 5.

In another embodiment, the invention embraces compounds of Formula IV-V:

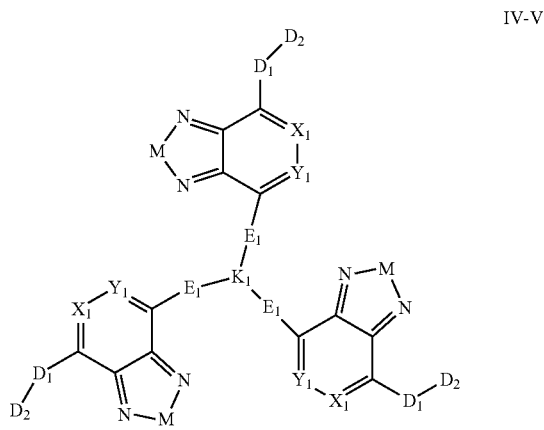

IV-V where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$ and $Y_2$ are selected from N and CH, where when $X_2$ is N, $Y_2$ is CH, and when $X_2$ is CH, $Y_2$ is N; and where, independently of $X_1$, $Y_1$, $X_2$, and $Y_2$, $X_3$ and $Y_3$ are selected from N and CH, where when $X_3$ is N, $Y_3$ is CH, and when $X_3$ is CH, $Y_3$ is N;

M is selected from sulfur (S), oxygen (O), or N—$R_1$, where $R_1$ is H, $C_1$-$C_{30}$ alkyl or $C_6$-$C_{30}$ aryl;

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $E_1$ is independently either absent, or selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula IV-V, each M is S. In one embodiment of Formula IV-V, each $D_1$ is the same moiety. In one embodiment of Formula IV-V, each $D_2$ is the same moiety. In one embodiment of Formula IV-V, each $D_1$ is the same moiety, and each $D_2$ is the same moiety (independently of $D_1$). In one embodiment of Formula IV-V, each M is S, each $D_1$ is the same moiety, and each $D_2$ is the same moiety (independently of $D_1$).

In some embodiments of Formula IV-V, $X_1$, $X_2$, and $X_3$ are each N and $Y_1$, $Y_2$, and $Y_3$, are each CH. In some embodiments of Formula IV-V, $X_1$, $X_2$, and $X_3$ are each CH and $Y_1$, $Y_2$, and $Y_3$ are each N.

In some embodiments of Formula IV-V, $X_1$, $X_2$, and $X_3$ are each N and $Y_1$, $Y_2$, and $Y_3$, are each CH, and each M is S. In some embodiments of Formula IV-V, $X_1$, $X_2$, and $X_3$ are each CH and $Y_1$, $Y_2$, and $Y_3$ are each N, and each M is S.

In some embodiments of Formula IV-V, $X_1$, $X_2$, and $X_3$ are each N and $Y_1$, $Y_2$, and $Y_3$, are each CH, and each M is O. In some embodiments of Formula IV-V, $X_1$, $X_2$, and $X_3$ are each CH and $Y_1$, $Y_2$, and $Y_3$ are each N, and each M is O.

In another embodiment, the invention embraces compounds of Formula IV-V of Formula IV:

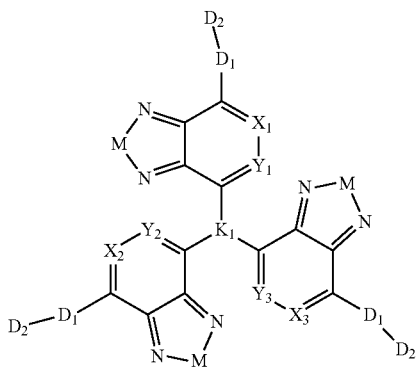

IV where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$ and $Y_2$ are selected from N and CH, where when $X_2$ is N, $Y_2$ is CH, and when $X_2$ is CH, $Y_2$ is N; and where, independently of $X_1$, $Y_1$, $X_2$, and $Y_2$, $X_3$ and $Y_3$ are selected from N and CH, where when $X_3$ is N, $Y_3$ is CH, and when $X_3$ is CH, $Y_3$ is N;

M is selected from sulfur (S), oxygen (O), or N—$R_1$, where $R_1$ is H, $C_1$-$C_{30}$ alkyl or $C_6$-$C_{30}$ aryl;

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole; and each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula IV, each M is S. In one embodiment of Formula IV, each $D_1$ is the same moiety. In one embodiment of Formula IV, each $D_2$ is the same moiety. In one embodiment of Formula IV, each $D_1$ is the same moiety, and each $D_2$ is the same moiety (independently of $D_1$). In one embodiment of Formula IV, each M is S, each $D_1$ is the same moiety, and each $D_2$ is the same moiety (independently of $D_1$).

In some embodiments of Formula IV, $X_1$, $X_2$, and $X_3$ are each N and $Y_1$, $Y_2$, and $Y_3$, are each CH. In some embodiments of Formula IV, $X_1$, $X_2$, and $X_3$ are each CH and $Y_1$, $Y_2$, and $Y_3$ are each N.

In some embodiments of Formula IV, $X_1$, $X_2$, and $X_3$ are each N and $Y_1$, $Y_2$, and $Y_3$, are each CH, and each M is S. In some embodiments of Formula IV, $X_1$, $X_2$, and $X_3$ are each CH and $Y_1$, $Y_2$, and $Y_3$ are each N, and each M is S.

In some embodiments of Formula IV, $X_1$, $X_2$, and $X_3$ are each N and $Y_1$, $Y_2$, and $Y_3$ are each CH, and each M is O. In some embodiments of Formula IV, $X_1$, $X_2$, and $X_3$ are each CH and $Y_1$, $Y_2$, and $Y_3$ are each N, and each M is O.

In another embodiment, the invention embraces compounds of Formula IV of Formula IVa or Formula IVb:

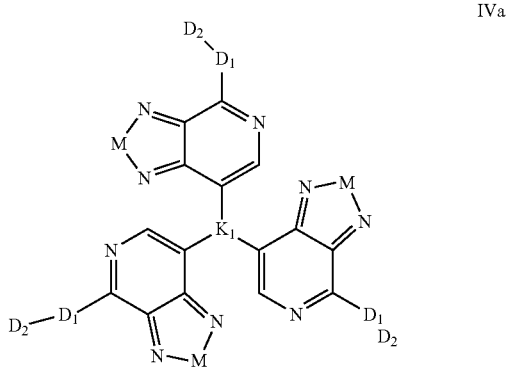

IVa

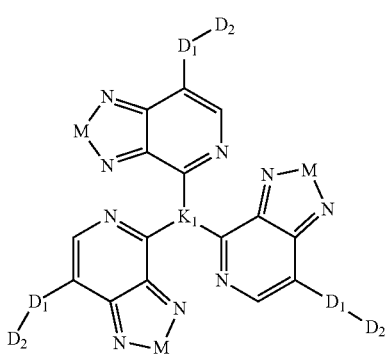

where M is selected from sulfur (S), oxygen (O), or N—R$_1$, where R$_1$ is H, C$_1$-C$_{30}$ alkyl or C$_6$-C$_{30}$ aryl;

K$_1$ is independently selected from substituted or unsubstituted aryl or heteroaryl groups, such as C$_6$-C$_{30}$ substituted or unsubstituted aryl or heteroaryl groups, C$_6$-C$_{20}$ substituted or unsubstituted aryl or heteroaryl groups, and C$_6$-C$_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each D$_1$ is independently selected from substituted or unsubstituted aryl or heteroaryl groups, such as C$_6$-C$_{30}$ substituted or unsubstituted aryl or heteroaryl groups, C$_6$-C$_{20}$ substituted or unsubstituted aryl or heteroaryl groups, and C$_6$-C$_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole; and each D$_2$ is independently selected from a nonentity, H, F, a C$_1$-C$_{16}$ alkyl group, or a substituted or unsubstituted aryl or heteroaryl group, such as C$_6$-C$_{30}$ substituted or unsubstituted aryl or heteroaryl groups, C$_6$-C$_{20}$ substituted or unsubstituted aryl or heteroaryl groups, and C$_6$-C$_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula IVa, each M is S. In one embodiment of Formula IVa, each D$_1$ is the same moiety. In one embodiment of Formula IVa, each D$_2$ is the same moiety. In one embodiment of Formula IVa, each D$_1$ is the same moiety, and each D$_2$ is the same moiety (independently of D$_1$). In one embodiment of Formula IVa, each M is S, each D$_1$ is the same moiety, and each D$_2$ is the same moiety (independently of D$_1$).

In one embodiment of Formula IVa, each M is O. In one embodiment of Formula IVa, each D$_1$ is the same moiety. In one embodiment of Formula IVa, each D$_2$ is the same moiety. In one embodiment of Formula IVa, each D$_1$ is the same moiety, and each D2 is the same moiety (independently of D$_1$). In one embodiment of Formula IVa, each M is O, each D$_1$ is the same moiety, and each D$_2$ is the same moiety (independently of D$_1$).

In one embodiment of Formula IVb, each M is S. In one embodiment of Formula IVb, each D$_1$ is the same moiety. In one embodiment of Formula IVb, each D$_2$ is the same moiety. In one embodiment of Formula IVb, each D$_1$ is the same moiety, and each D$_2$ is the same moiety (independently of D$_1$). In one embodiment of Formula IVb, each M is S, each D$_1$ is the same moiety, and each D$_2$ is the same moiety (independently of D$_1$).

In one embodiment of Formula IVb, each M is O. In one embodiment of Formula IVb, each D$_1$ is the same moiety. In one embodiment of Formula IVb, each D$_2$ is the same moiety. In one embodiment of Formula IVb, each D$_1$ is the same moiety, and each D$_2$ is the same moiety (independently of D$_1$). In one embodiment of Formula IVb, each M is O, each D$_1$ is the same moiety, and each D$_2$ is the same moiety (independently of D$_1$).

In another embodiment, the invention embraces compounds of Formula IV-V of Formula V:

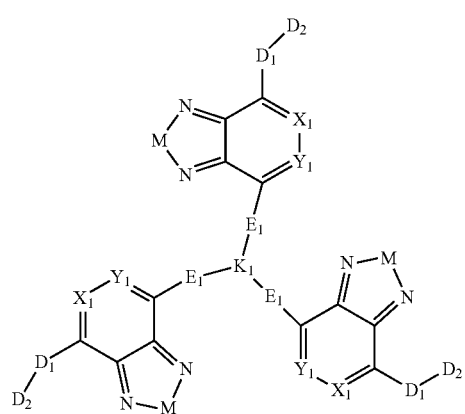

where X$_1$ and Y$_1$ are selected from N and CH, where when X$_1$ is N, Y$_1$ is CH, and when X$_1$ is CH, Y$_1$ is N; and where, independently of X$_1$ and Y$_1$, X$_2$ and Y$_2$ are selected from N and CH, where when X$_2$ is N, Y$_2$ is CH, and when X$_2$ is CH, Y$_2$ is N; and where, independently of X$_1$, Y$_1$, X$_2$, and Y$_2$, X$_3$ and Y$_3$ are selected from N and CH, where when X$_3$ is N, Y$_3$ is CH, and when X$_3$ is CH, Y$_3$ is N;

where M is selected from sulfur (S), oxygen (O), or N—$R_1$, where $R_1$ is H, $C_1$-$C_{30}$ alkyl or $C_6$-$C_{30}$ aryl;

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ and $E_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{29}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula V, each M is S. In one embodiment of Formula V, each $D_1$ is the same moiety. In one embodiment of Formula V, each $D_2$ is the same moiety. In one embodiment of Formula V, each $D_1$ is the same moiety, and each $D_2$ is the same moiety (independently of $D_1$). In one embodiment of Formula V, each M is S, each $D_1$ is the same moiety, and each $D_2$ is the same moiety (independently of $D_1$).

In some embodiments of Formula V, $X_1$, $X_2$, and $X_3$ are each N and $Y_1$, $Y_2$, and $Y_3$, are each CH. In some embodiments of Formula V, $X_1$, $X_2$, and $X_3$ are each CH and $Y_1$, $Y_2$, and $Y_3$ are each N.

In some embodiments of Formula V, $X_1$, $X_2$, and $X_3$ are each N and $Y_1$, $Y_2$, and $Y_3$, are each CH, and each M is S. In some embodiments of Formula V, $X_1$, $X_2$, and $X_3$ are each CH and $Y_1$, $Y_2$, and $Y_3$ are each N, and each M is S.

In some embodiments of Formula V, $X_1$, $X_2$, and $X_3$ are each N and $Y_1$, $Y_2$, and $Y_3$, are each CH, and each M is O. In some embodiments of Formula V, $X_1$, $X_2$, and $X_3$ are each CH and $Y_1$, $Y_2$, and $Y_3$ are each N, and each M is O.

In another embodiment, the invention embraces compounds of Formula Va or Formula Vb:

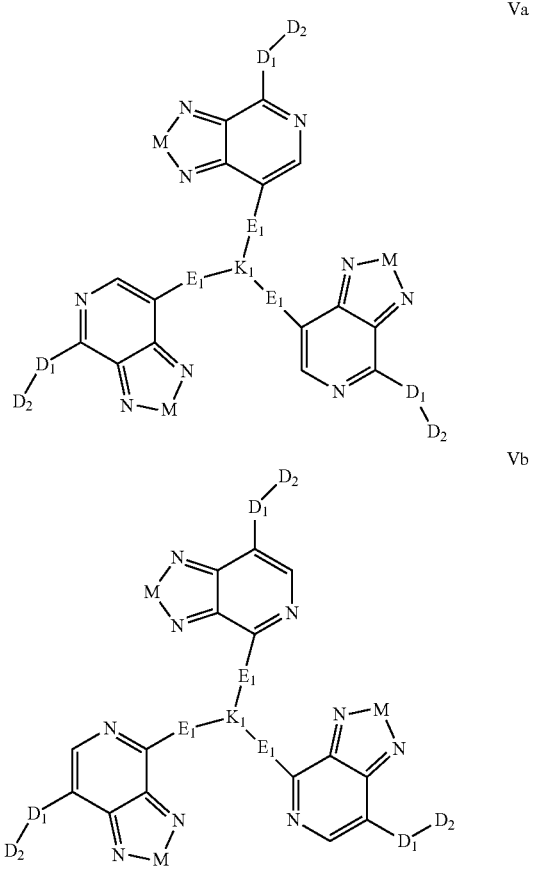

where M is selected from sulfur (S), oxygen (O), or N—$R_1$, where $R_1$ is H, $C_1$-$C_{30}$ alkyl or $C_6$-$C_{30}$ aryl;

$K_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_1$ and $E_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole;

each $D_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl and heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, dithienopyrrole, dithienophosphole, and carbazole.

In one embodiment of Formula Va, each M is S. In one embodiment of Formula Va, each $E_1$ is the same moiety. In one embodiment of Formula Va, each $D_1$ is the same moiety. In one embodiment of Formula Va, each $D_2$ is the same moiety. In one embodiment of Formula Va, each $E_1$ is the same moiety, each $D_1$ is the same moiety, and each $D_2$ is the same moiety (where $E_1$, $D_1$, and $D_2$ are chosen independently of each other). In one embodiment of Formula Va, each M is S, and each $E_1$ is the same moiety, each $D_1$ is the same moiety, and each $D_2$ is the same moiety (where $E_1$, $D_1$, and $D_2$ are chosen independently of each other).

In one embodiment of Formula Va, each M is O. In one embodiment of Formula Va, each $E_1$ is the same moiety. In one embodiment of Formula Va, each $D_1$ is the same moiety. In one embodiment of Formula Va, each $D_2$ is the same moiety. In one embodiment of Formula. Va, each $E_1$ is the same moiety, each $D_1$ is the same moiety, and each $D_2$ is the same moiety (where $E_1$, $D_1$, and $D_2$ are chosen independently of each other). In one embodiment of Formula Va, each M is O, and each $E_1$ is the same moiety, each $D_1$ is the same moiety, and each D2 is the same moiety (where $E_1$, $D_1$, and $D_2$ are chosen independently of each other).

In one embodiment of Formula Vb, each M is S. In one embodiment of Formula Vb, each $E_1$ is the same moiety. In one embodiment of Formula Vb, each $D_1$ is the same moiety. In one embodiment of Formula Vb, each $D_2$ is the same moiety. In one embodiment of Formula Vb, each $E_1$ is the same moiety, each $D_1$ is the same moiety, and each $D_2$ is the same moiety (where $E_1$, $D_1$, and $D_2$ are chosen independently of each other). In one embodiment of Formula Vb, each M is S, and each $E_1$ is the same moiety, each $D_1$ is the same moiety, and each $D_2$ is the same moiety (where $E_1$, $D_1$, and $D_2$ are chosen independently of each other).

In one embodiment of Formula Vb, each M is O. In one embodiment of Formula Vb, each $E_1$ is the same moiety. In one embodiment of Formula Vb, each $D_1$ is the same moiety. In one embodiment of Formula Vb, each $D_2$ is the same moiety. In one embodiment of Formula Vb, each $E_1$ is the same moiety, each $D_1$ is the same moiety, and each $D_2$ is the same moiety (where $E_1$, $D_1$, and $D_2$ are chosen independently of each other). In one embodiment of Formula Vb, each M is O, and each $E_1$ is the same moiety, each $D_1$ is the same moiety, and each $D_2$ is the same moiety (where $E_1$, $D_1$, and $D_2$ are chosen independently of each other).

In another embodiment, the invention embraces compounds of Formula VI-VII:

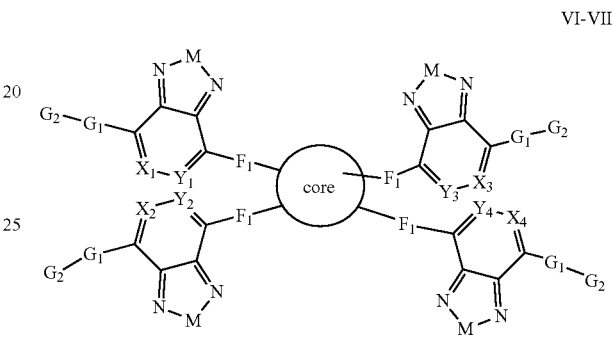

VI-VII where the moiety

is selected from

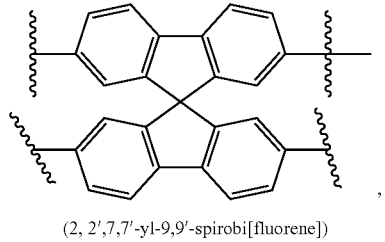

(2, 2′,7,7′-yl-9,9′-spirobi[fluorene])

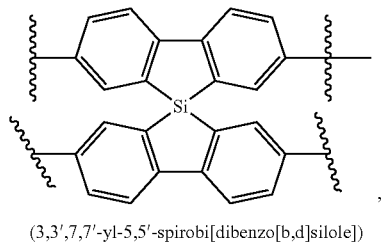

(3,3′,7,7′-yl-5,5′-spirobi[dibenzo[b,d]silole])

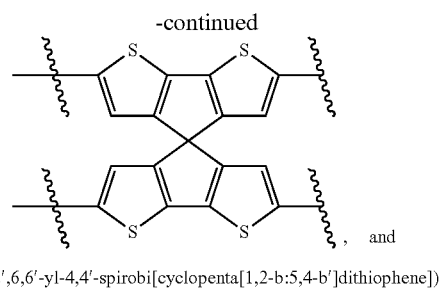

(2,2',6,6'-yl-4,4'-spirobi[cyclopenta[1,2-b:5,4-b']dithiophene]) , and

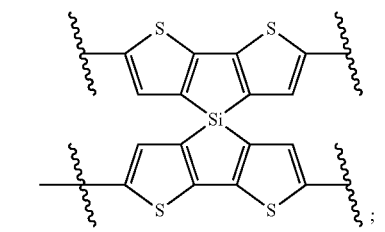

(2,2',6,6'-yl-4,4'-spirobi[silolo[3,2-b:4,5-b']dithiophene]) ;

where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$, and $Y_2$ are selected from N and CH, where when $X_2$ is N, $Y_2$ is CH, and when $X_2$ is CH, $Y_2$ is N; and where, independently of $X_1$, $Y_1$, $X_2$, and $Y_2$, $X_3$ and $Y_3$ are selected from N and CH, where when $X_3$ is N, $Y_3$ is CH, and when $X_3$ is CH, $Y_3$ is N; and where, independently of $X_1$, $Y_1$, $X_2$, $Y_2$, $X_3$, and $Y_3$, $X_4$ and $Y_4$ are selected from N and CH, where when $X_4$ is N, $Y_4$ is CH, and when $X_4$ is CH, $Y_4$ is N;

where M is selected from sulfur (S), oxygen (O), or N—$R_1$, where $R_1$ is H, $C_1$-$C_{30}$ alkyl or $C_6$-$C_{30}$ aryl;

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, toluene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene 2,2'-bithiophene, 3,3'RR'-cyclopenta[2,1-b:3,4-b']dithiophene, where R and R'=$C_1$-$C_{30}$ alkyl or $C_6$-$C_{30}$ aryl;

each $G_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, pyrimidine, pyrazine, imidazole, benzoxazole, benzoxadiazole, benzothiazole, benzimidazole, benzofuran, isobenzofuran, thiadiazole, perfluorylbenzene, and carbazole; and each $G_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VI-VII, each M is S. In other embodiments of Formula VI-VII, each M is O.

In some embodiments of Formula VI-VII, $X_1$, $X_2$, $X_3$, and $X_4$ are each N and $Y_1$, $Y_2$, $Y_3$, and $Y_4$ are each CH. In some embodiments of Formula VI-VII, $X_1$, $X_2$, $X_3$, and $X_4$ are each CH and $Y_1$, $Y_2$, $Y_3$, and $Y_4$ are each N.

In some embodiments of Formula VI-VII, $X_1$, $X_2$, $X_3$, and $X_4$ are each N and $Y_1$, $Y_2$, $Y_3$, and $Y_4$ are each CH, and each M is S. In some embodiments of Formula. VI-VII, $X_1$, $X_2$, $X_3$, and $X_4$ are each CH and $Y_1$, $Y_2$, $Y_3$, and $Y_4$ are each N, and each M is S.

In some embodiments of Formula VI-VII, $X_1$, $X_2$, $X_3$, and $X_4$ are each N and $Y_1$, $Y_2$, $Y_3$, and $Y_4$ are each CH, and each M is O. In some embodiments of Formula VI-VII, $X_1$, $X_2$, $X_3$, and $X_4$ are each CH and $Y_1$, $Y_2$, $Y_3$, and $Y_4$ are each N, and each M is O.

In some embodiments of Formula VI-VII, each $F_1$ is the same moiety. In some embodiments of Formula VI-VII, each $G_1$ is the same moiety. In some embodiments of Formula VI-VII, each $G_2$ is the same moiety. In some embodiments of Formula VI-VII, each $F_1$ is the same moiety, each $G_1$ is the same moiety, and each $G_2$ is the same moiety (where $F_1$, $G_1$, and $G_2$ are chosen independently of each other). In some embodiments of Formula VI-VII, each $F_1$ is the same moiety, each $G_1$ is the same moiety, and each $G_2$ is the same moiety (where $F_1$, $G_1$, and $G_2$ are chosen independently of each other); and M is S. In some embodiments of Formula VI-VII, each $F_1$ is the same moiety, each $G_1$ is the same moiety, and each $G_2$ is the same moiety (where $F_1$, $G_1$, and $G_2$ are chosen independently of each other); and M is O.

In another embodiment, the invention embraces compounds of Formula VI:

VI

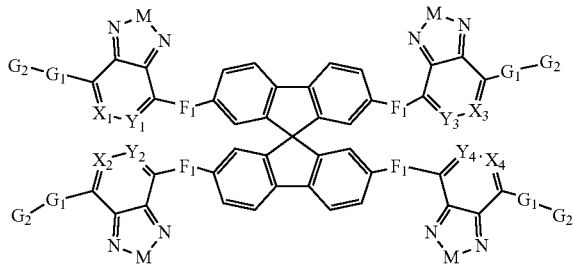

where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$ and $Y_2$ are selected from N and CH, where when $X_2$ is N, $Y_2$ is CH, and when $X_2$ is CH, $Y_2$ is N; and where, independently of $X_1$, $Y_1$, $X_2$, and $Y_2$, $X_3$ and $Y_3$ are selected from N and CH, where when $X_3$ is N, $Y_3$ is CH, and when $X_3$ is CH, $Y_3$ is N; and where, independently of $X_1$, $Y_1$, $X_2$, $Y_2$, $X_3$, and $Y_3$, $X_4$ and $Y_4$ are selected from N and CH, where when is N, $Y_4$ is CH, and when $X_4$ is CH, $Y_4$ is N;

where M is selected from sulfur (S), oxygen (O), or N—$R_1$, where $R_1$ is H, $C_1$-$C_{30}$ alkyl or $C_6$-$C_{30}$ aryl;

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b;3,4-b']-dithiophene, where R and R'=$C_1$-$C_{30}$ alkyl or $C_6$-$C_{30}$ aryl;

each $G_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole; and each $G_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran isobenzofuran, thiadiazole, perfluorylbenzene, and carbazole.

In some embodiments of Formula VI, each M is S. In other embodiments of Formula VI, each M is O.

In some embodiments of Formula VI, $X_1$, $X_2$, $X_3$, and $X_4$ are each N and $Y_1$, $Y_2$, $Y_3$, and $Y_4$ are each CH. In some embodiments of Formula VI, $X_1$, $X_2$, $X_3$, and $X_4$ are each CH and $Y_1$, $Y_2$, $Y_3$, and $Y_4$ are each N.

In some embodiments of Formula VI, $X_1$, $X_2$, $X_3$, and $X_4$ are each N and $Y_1$, $Y_2$, $Y_3$, and $Y_4$ are each CH, and each M is S. In some embodiments of Formula VI, $X_1$, $X_2$, $X_3$, and $X_4$ are each CH and $Y_1$, $Y_2$, $Y_3$, and $Y_4$ are each N, and each M is S.

In some embodiments of Formula VI, $X_1$, $X_2$, $X_3$, and $X_4$ are each N and $Y_1$, $Y_2$, $Y_3$, and $Y_4$ are each CH, and each M is O. In some embodiments of Formula VI, $X_1$, $X_2$, $X_3$, and $X_4$ are each CH and $Y_1$, $Y_2$, $Y_3$, and $Y_4$ are each N, and each M is O.

In some embodiments of Formula VI, each $F_1$ is the same. In some embodiments of Formula VI, each $G_1$ is the same. In some embodiments of Formula VI, each $G_2$ is the same. In some embodiments of Formula VI, each $F_1$ is the same, each $G_1$ is the same, and each $G_2$ is the same (where $F_1$, $B_1$, and $G_2$ are chosen independently of each other). In some embodiments of Formula VI, each $F_1$ is the same, each $G_1$ is the same, and each $G_2$ is the same (where $F_1$, $G_1$, and $G_2$ are chosen independently of each other); and M is S. In some embodiments of Formula VI, each $F_1$ is the same, each $G_1$ is the same, and each $G_2$ is the same (where $F_1$, $G_1$, and $G_2$ are chosen independently of each other); and M is O.

In another embodiment, the invention embraces compounds of Formula VI, such as compounds of Formula VIa or Formula VIb:

VIa

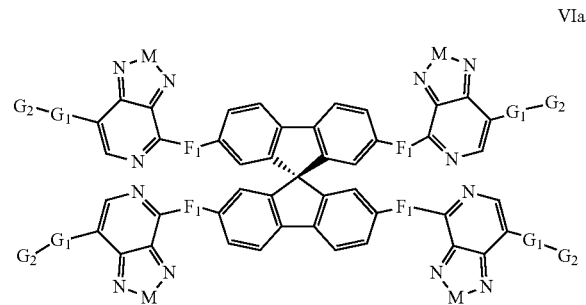

-continued

VIb

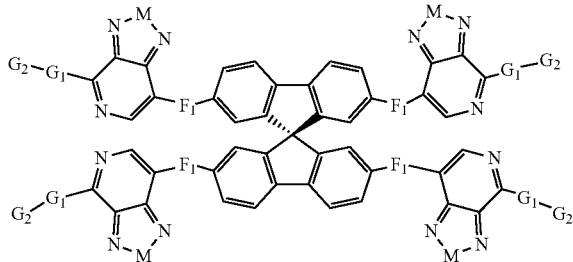

where M is selected from sulfur (S), oxygen (O), or N—$R_1$, where $R_1$ is H, $C_1$-$C_{30}$ alkyl or $C_6$-$C_{30}$ aryl;

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene 2,2'-bithiophene, 3,3'RR'-cyclopenta[2,1-b;3,4-b']-dithiophene, where R and R'=$C_1$-$C_{30}$ alkyl or $C_6$-$C_{30}$ aryl;

each $G_1$ is independently selected from substituted or unsubstituted aryl or heteroaryl groups, such as $C_6$-$C_{30}$ substituted or unsubstituted aryl or heteroaryl groups, ($C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole; and each $G_2$ is independently selected from a nonentity, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VIa, each M is S. In other embodiments of Formula VIa, each M is O. In some embodiments of Formula VIa, each $F_1$ is the same. In some embodiments of Formula VIa, each $G_1$ is the same. In some embodiments of Formula VIa, each $G_2$ is the same. In some embodiments of Formula VIa, each $F_1$ is the same, each $G_1$ is the same, and each $G_2$ is the same (where $F_1$, $G_1$, and $G_2$ are chosen independently of each other). In some embodiments of Formula VIa, each $F_1$ is the same, each $G_1$ is the same, and each $G_2$ is the same (where $F_1$, $G_1$, and $G_2$ are chosen independently of each other); and M is S. In some embodiments of Formula VIa, each $F_1$ is the same, each $G_1$ is the same (where $F_1$, $G_1$, and $G_2$ are chosen independently of each other), and each $G_2$ is the same; and M is O.

In some embodiments of Formula VIb, each M is S. In other embodiments of Formula VIb, each M is O. In some embodiments of Formula VIb, each $F_1$ is the same. In some embodiments of Formula VIb, each $G_1$ is the same. In some embodiments of Formula VIb, each $G_2$ is the same. In some embodiments of Formula VIb, each $F_1$ is the same, each $G_1$ is the same, and each $G_2$ is the same (where $F_1$, $G_1$, and $G_2$ are chosen independently of each other). In some embodiments of Formula VIb, each $F_1$ is the same, each $G_1$ is the same, and each $G_2$ is the same (where $F_1$, $G_1$, and $G_2$ are chosen independently of each other); and M is S. In some embodiments of Formula VIb, each $F_1$ is the same, each $G_1$ is the same (where $F_1$, $G_1$, and $G_2$ are chosen independently of each other), and each G2 is the same; and M is O.

In another embodiment, the invention embraces compounds of Formula VII:

VII

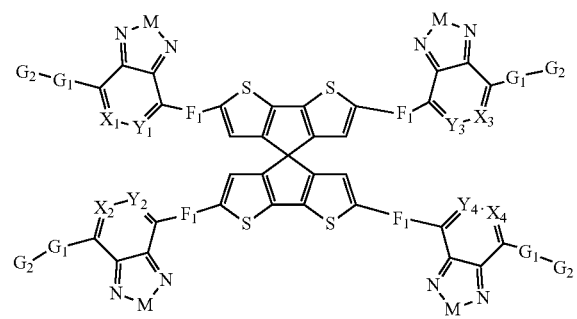

where $X_1$ and $Y_1$ are selected from N and CH, where when $X_1$ is N, $Y_1$ is CH, and when $X_1$ is CH, $Y_1$ is N; and where, independently of $X_1$ and $Y_1$, $X_2$ and $Y_2$ are selected from N and CH, where when $X_2$ is N, $Y_2$ is CH, and when $X_2$ is CH, $Y_2$ is N; and where, independently of $X_1$, $Y_1$, $X_2$ and $Y_2$, $X_3$ and $Y_3$ are selected from N and CH, where when $X_3$ is N, $Y_3$ is CH, and when $X_3$ is CH, $Y_3$ is N; and where, independently of $X_1$, $Y_1$, $X_2$, $Y_2$, $X_3$, and $Y_3$, $X_4$ and $Y_4$ are selected from N and CH, where when $X_4$ is N, $Y_4$ is CH, and when $X_4$ is CH, $Y_4$ is N;

where M is selected from sulfur (S), oxygen (O), or N—$R_1$, where $R_1$ is H, $C_1$-$C_{30}$ alkyl or $C_6$-$C_{30}$ aryl;

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene-2,2'-bithiophene, 3,3'RR'-cyclopenta[2,1-b:3,4-b']dithiophene, where R and R'=$C_1$-$C_{30}$ alkyl or $C_6$-$C_{30}$ aryl;

each $G_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole; and each $G_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups, Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VII, each M is S. In other embodiments of Formula VII, each M is O.

In some embodiments of Formula VII, $X_1$, $X_2$, $X_3$, and $X_4$ are each N and $Y_1$, $Y_2$, $Y_3$, and $Y_4$ are each CH. In some embodiments of Formula VII, $X_1$, $X_2$, $X_3$, and $X_4$ are each CH and $Y_1$, $Y_2$, $Y_3$, and $Y_4$ are each N.

In some embodiments of Formula VII, $X_1$, $X_2$, $X_3$, and $X_4$ are each N and $Y_1$, $Y_2$, $Y_3$, and $Y_4$ are each CH, and each M is S. In some embodiments of Formula VII, $X_1$, $X_2$, $X_3$, and $X_4$ are each CH and $Y_1$, $Y_2$, $Y_3$, and $Y_4$ are each N, and each M is S.

In some embodiments of Formula VII, $X_1$, $X_2$, $X_3$, and $X_4$ are each N and $Y_1$, $Y_2$, $Y_3$, and $Y_4$ are each CH, and each M is O. In some embodiments of Formula VII, $X_1$, $X_2$, $X_3$, and $X_4$ are each CH and $Y_1$, $Y_2$, $Y_3$, and $Y_4$ are each N, and each M is O.

In some embodiments of Formula VII, each $F_1$ is the same. In some embodiments of Formula VII, each $G_1$ is the same. In some embodiments of Formula VII, each $G_2$ is the same. In some embodiments of Formula VII, each $F_1$ is the same, each $G_1$ is the same, and each $G_2$ is the same (where $F_1$, $G_1$, and $G_2$ are chosen independently of each other). In some embodiments of Formula VII, each $F_1$ is the same, each $G_1$ is the same, and each $G_2$ is the same (where $F_1$, $G_1$, and $G_2$ are chosen independently of each other); and M is S. In some embodiments of Formula VII, each $F_1$ is the same, each $G_1$ is the same, and each $G_2$ is the same (where $F_1$, $G_1$, and $G_2$ are chosen independently of each other); and M is O.

In another embodiment, the invention embraces compounds of Formula VII, such as compounds of Formula VIIa or Formula VIIb:

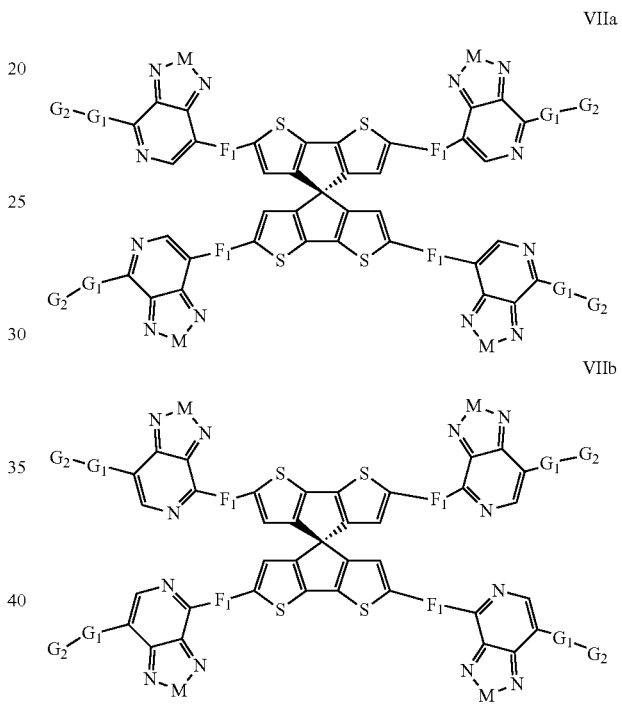

where M is selected from sulfur (S), oxygen (O), or N—$R_1$, where $R_1$ is H, $C_1$-$C_{30}$ alkyl or $C_6$-$C_{30}$ aryl;

each $F_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, dithienopyrrole, dithienophosphole, and carbazole 9,9-RR'-9H-fluorene, 9-R-9H-carbazole, 3,3'-RR'silylene 2,2'-bithiophene, 3,3'RR'-cyclopenta[2,1-b:3,4-b']dithiophene, where R and R'=$C_1$-$C_{30}$ alkyl or $C_6$-$C_{30}$ aryl.

Each $G_1$ is independently selected from substituted or unsubstituted aryl or heteroaryl groups, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

Each $G_2$ is independently selected from a nonentity, H, F, a $C_1$-$C_{16}$ alkyl group, or a substituted or unsubstituted aryl or heteroaryl group, such as $C_6$-$C_{30}$ substituted or unsubstituted aryl or heteroaryl groups, $C_6$-$C_{20}$ substituted or unsubstituted aryl or heteroaryl groups, and $C_6$-$C_{10}$ substituted or unsubstituted aryl or heteroaryl groups. Examples of aryl or heteroaryl groups include, but are not limited to, thiophene, pyrrole, furan, phenyl, phosphole, benzodithiophene, spirofluorene, spirothiophene, bithiophene, terthiophene, thienothiophene, dithienothiophene, benzothiophene, isobenzothiophene, benzodithiophene, cyclopentadithiophene, silacyclopentadiene, silacyclopentadienebithiophene, indole, benzene, naphthalene, anthracene, perylene, indene, fluorene, pyrene, azulene, pyridine, oxazole, thiazole, thiazine, thiazolyl, pyrimidine, pyrazine, imidazole, benzoxazole, benzoxadiazole, benzothiazole, benzimidazole, benzofuran, isobenzofuran, thiadiazole, perfluorylbenzene, and carbazole.

In some embodiments of Formula VIIa, each M is S. In other embodiments of Formula VIIa, each M is O. In some embodiments of Formula VIIa, each $F_1$ is the same. In some embodiments of Formula VIIa, each $G_1$ is the same. In some embodiments of Formula VIIa, each $G_2$ is the same. In some embodiments of Formula VIIa, each $F_1$ is the same, each $G_1$ is the same, and each $G_2$ is the same (where $G_1$ and $G_2$ are chosen independently of each other). In some embodiments of Formula VIIa, each $F_1$ is the same, each $G_1$ is the same, and each $G_2$ is the same (where $F_1$, $G_1$, and $G_2$ are chosen independently of each other); and M is S. In some embodiments of Formula VIIa, each $F_1$ is the same, each $G_1$ is the same (where $F_1$, $G_1$, and $G_2$ are chosen independently of each other), and each $G_2$ is the same; and M is O.

In some embodiments of Formula VIIb, each M is S. In other embodiments of Formula VIIb, each M is O. In some embodiments of Formula VIIb, each $F_1$ is the same. In some embodiments of Formula VIIb, each $G_1$ is the same. In some embodiments of Formula VIIb, each $G_2$ is the same. In some embodiments of Formula VIIb, each $F_1$ is the same, each $G_1$ is the same, and each $G_2$ is the same (where $F_1$, $G_1$, and $G_2$ are chosen independently of each other). In some embodiments of Formula VIIb, each $F_1$ is the same, each $G_1$ is the same, and each $G_2$ is the same (where $F_1$, $G_1$, and $G_2$ are chosen independently of each other); and M is S. In some embodiments of Formula VIIb, each $F_1$ is the same, each $G_1$ is the same, and each $G_2$ is the same (where $F_1$, $G_1$, and $G_2$ are chosen independently of each other); and M is O.

In additional embodiments, the invention embraces compounds of Formula 1-2-3-4-5:

where $P_1$ is selected from

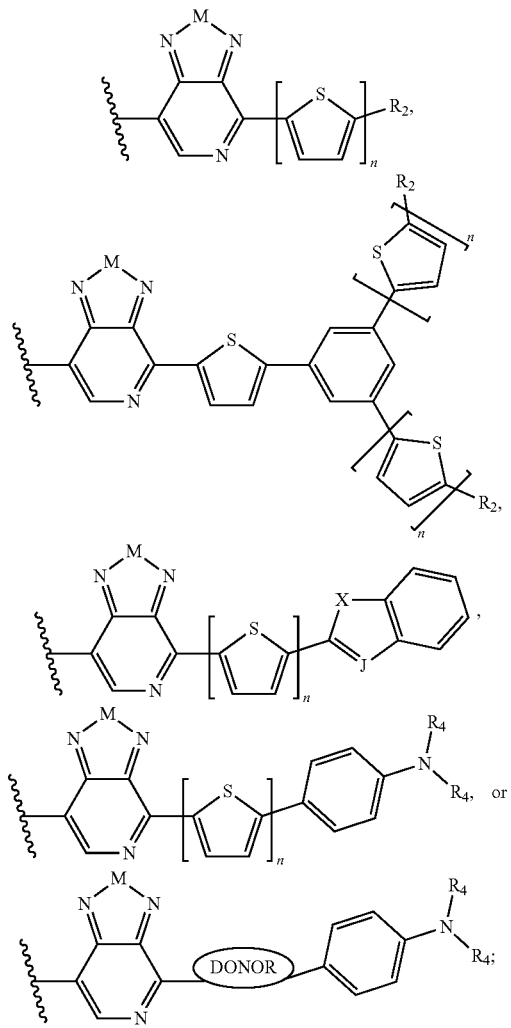

where M is selected from sulfur (S), oxygen (O), or N—$R_1$, where $R_1$ is H, $C_1$-$C_{30}$ alkyl or $C_6$-$C_{30}$ aryl;

n is an integer from 0 to 5 inclusive;

$R_2$ is selected from H, $C_1$-$C_{16}$ alkyl, —O—$C_1$-$C_{16}$ alkyl, $C_2$-$C_{16}$ alkenyl, and $C_2$-$C_{16}$ alkynyl;

J is selected from CH and N;

X is S, O, or NH when X is CH; and X is S when J is N;

$R_4$ is selected from aryl or aryl substituted with alkyl, such as $C_6$-$C_{30}$ aryl optionally substituted with one or more $C_1$-$C_{16}$ alkyl groups, $C_6$-$C_{20}$ aryl optionally substituted with one or more $C_1$-$C_{16}$ alkyl groups, and $C_6$-$C_{10}$ aryl groups optionally substituted with one or more $C_1$-$C_{16}$ alkyl groups, and where DONOR is as defined below.

In one embodiment, n is 0. In another embodiment, n is 1. In another embodiment, n is 2. In another embodiment, n is 3. In another embodiment, n is 4. In another embodiment, n is 5;

In additional embodiments, the invention embraces compounds of Formula 1, Formula 2, Formula 3, Formula 4, or Formula 5:

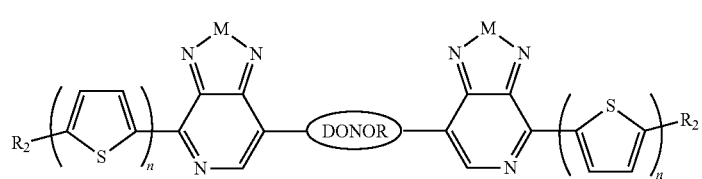

1

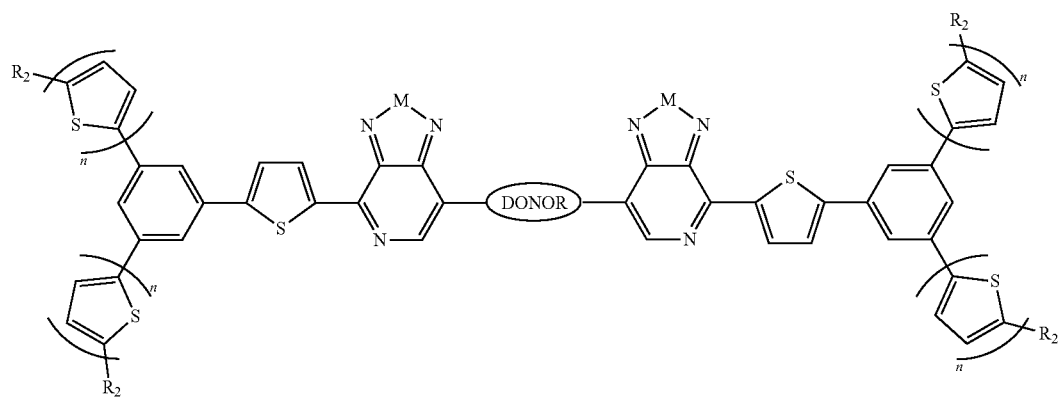

2

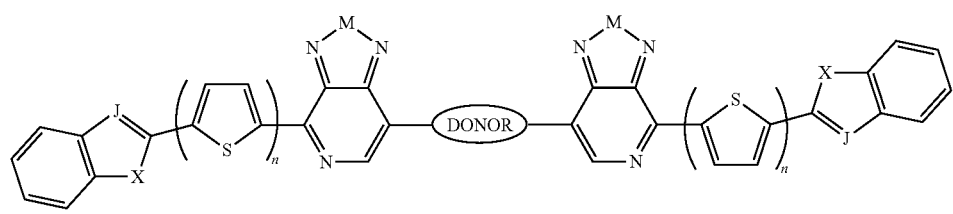

3

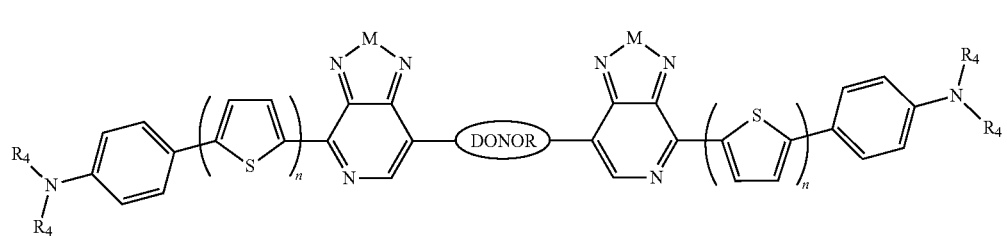

4

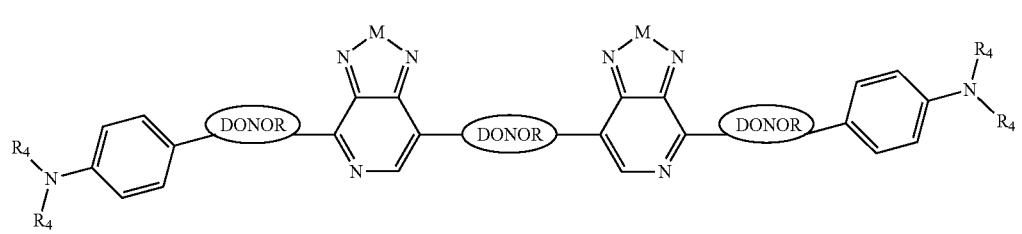

5

In the structures for Formula 1, Formula 2, Formula 3, Formula 4, and Formula 5 above:

M is selected from sulfur (S), oxygen (O), or N—$R_1$, where $R_1$ is H, $C_1$-$C_{30}$ alkyl or $C_6$-$C_{30}$ aryl;

n is an integer from 0 to 5 inclusive;

$R_2$ is selected from H, $C_1$-$C_{16}$ alkyl, —O—$C_1$-$C_{16}$ alkyl, $C_2$-$C_{16}$ alkenyl, and $C_2$-$C_{16}$ alkynyl;

J is selected from CH and N;

X is S, O, or NH when X is CH; and X is S when J is N;

$R_4$ is selected from aryl or aryl substituted with alkyl, such as $C_6$-$C_{30}$ aryl optionally substituted with one or more $C_1$-$C_{16}$ alkyl groups, $C_6$-$C_{20}$ aryl optionally substituted with one or more $C_1$-$C_{16}$ alkyl groups, and $C_6$-$C_{10}$ aryl groups optionally substituted with one or more $C_1$-$C_{16}$ alkyl groups, and where DONOR is as defined below.

In one embodiment, n is 0. In another embodiment, n is 1. In another embodiment, n is 2. In another embodiment, n is 3. In another embodiment, n is 4. In another embodiment, n is 5

In additional embodiments, the invention embraces compounds of Formula 6-7-8:

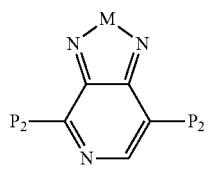

where $P_2$ is selected from:

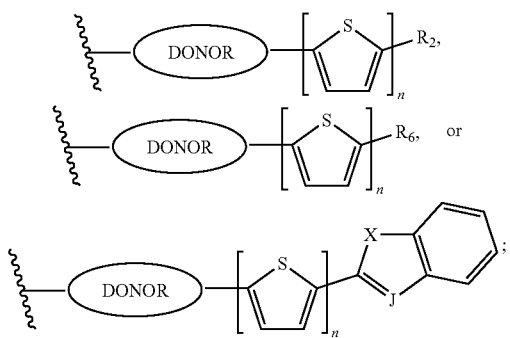

where M is selected from sulfur (S), oxygen (O), or N—$R_1$, where $R_1$ is H, $C_1$-$C_{30}$ alkyl or $C_6$-$C_{30}$ aryl;

n is an integer from 0 to 5 inclusive;

$R_2$ is selected from H, $C_1$-$C_{16}$ alkyl, —O—$C_1$-$C_{16}$ alkyl, $C_2$-$C_{16}$ alkenyl, and $C_2$-$C_{16}$ alkynyl;

J is selected from CH and N;

X is S, O, or NH when X is CH; and X is S when J is N;

$R_6$ is selected from aryl, perfluoroaryl, or aryl substituted with alkyl, such as $C_6$-$C_{30}$ aryl optionally perfluorinated or optionally substituted with one or more $C_1$-$C_{16}$ alkyl groups, $C_6$-$C_{20}$ aryl optionally perfluorinated or optionally substituted with one or more $C_1$-$C_{16}$ alkyl groups, and $C_6$-$C_{10}$ aryl groups optionally perfluorinated or optionally substituted with one or more $C_1$-$C_{16}$ alkyl groups; and where DONOR is as defined below.

In one embodiment, n is 0. In another embodiment, n is 1. In another embodiment, n is 2. In another embodiment, n is 3. In another embodiment, n is 4. In another embodiment, n is 5.

In additional embodiments, the invention embraces compounds of Formula 6, Formula 7, or Formula 8:

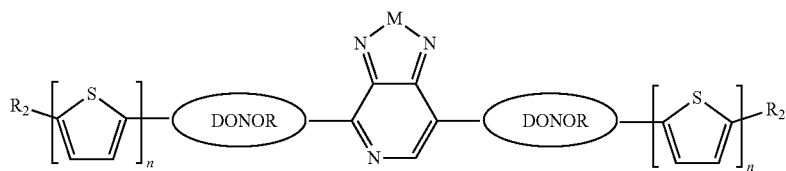

6

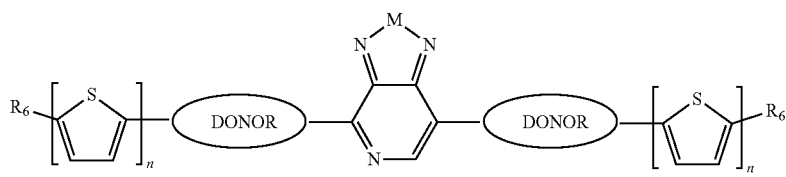

7

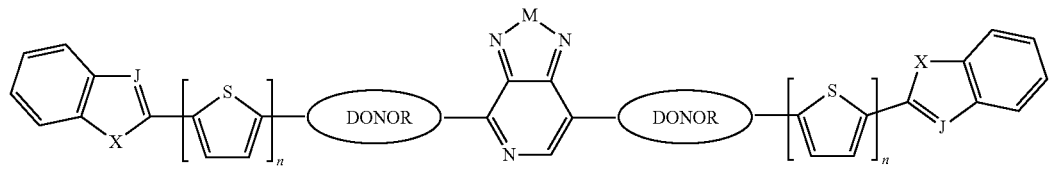

8

In the structures for Formula 6. Formula 7, and Formula 8 above:

M is selected from sulfur (S), oxygen (O), or N—$R_1$, where $R_1$ is H. $C_1$-$C_{30}$ alkyl or $C_6$-$C_{30}$ aryl;

n is an integer from 0 to 5 inclusive;

$R_2$ is selected from H, $C_1$-$C_{16}$ alkyl, —O—$C_1$-$C_{16}$ alkyl, $C_2$-$C_{16}$ alkenyl, and $C_2$-$C_{16}$ alkynyl;

J is selected from CH and N;

X is S, O, or NH when X is CH; and X is S when J is N;

$R_6$ is selected from aryl, perfluoroaryl, or aryl substituted with alkyl, such as $C_6$-$C_{30}$ aryl optionally perfluorinated or optionally substituted with one or more $C_1$-$C_{16}$ alkyl groups. $C_6$-$C_{20}$ aryl optionally perfluorinated or optionally substituted with one or more $C_1$-$C_{16}$ alkyl groups, and $C_6$-$C_{10}$ aryl groups optionally perfluorinated or optionally substituted with one or more $C_1$-$C_{16}$ alkyl groups; and where DONOR is as defined below.

In one embodiment, n is 0. In another embodiment, n is 1. In another embodiment, n is 2. In another embodiment, n is 3. In another embodiment, n is 4. In another embodiment, n is 5.

In additional embodiments, the invention embraces compounds of Formula 9-10:

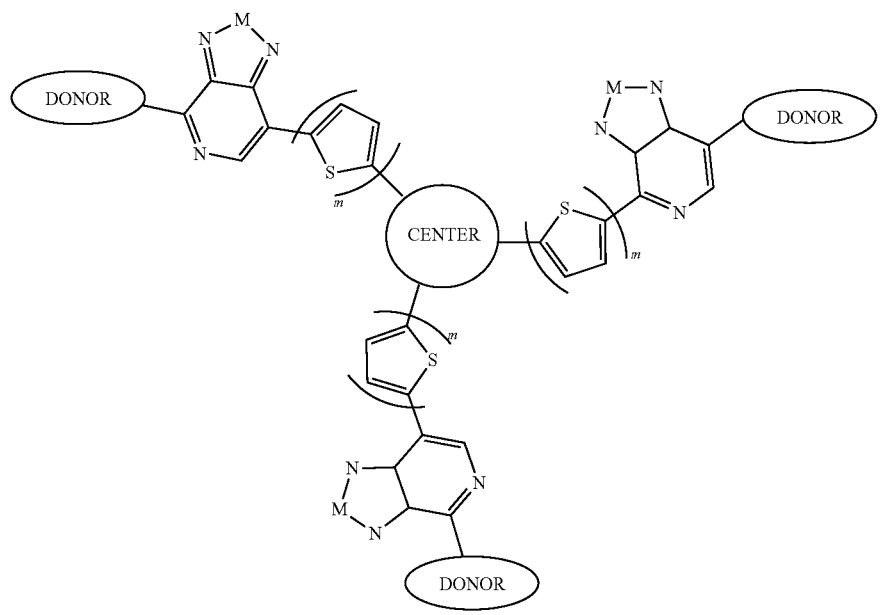 where 

is selected from

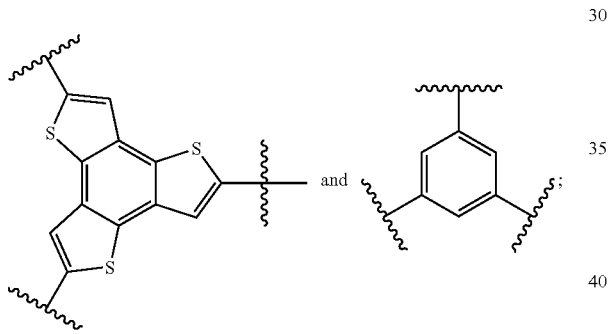

where M is selected from sulfur (S), oxygen (O), or N—$R_1$, where. $R_1$ is H, $C_1$-$C_{30}$ alkyl or $C_6$-$C_{30}$ aryl;

n is an integer from 1 to 5 inclusive, and m is an integer from 0 to 5 inclusive; and where DONOR is as defined below.

In one embodiment, n is 1. In another embodiment, n is 2. In another embodiment, n is 3. In another embodiment, n is 4. In another embodiment, n is 5. In another embodiment, m is 0. In another embodiment, m is 1. In another embodiment, m is 2. In another embodiment, m is 3. In another embodiment, m is 4. In another embodiment, m is 5

In additional embodiments, the invention embraces compounds of Formula 9 or Formula 10:

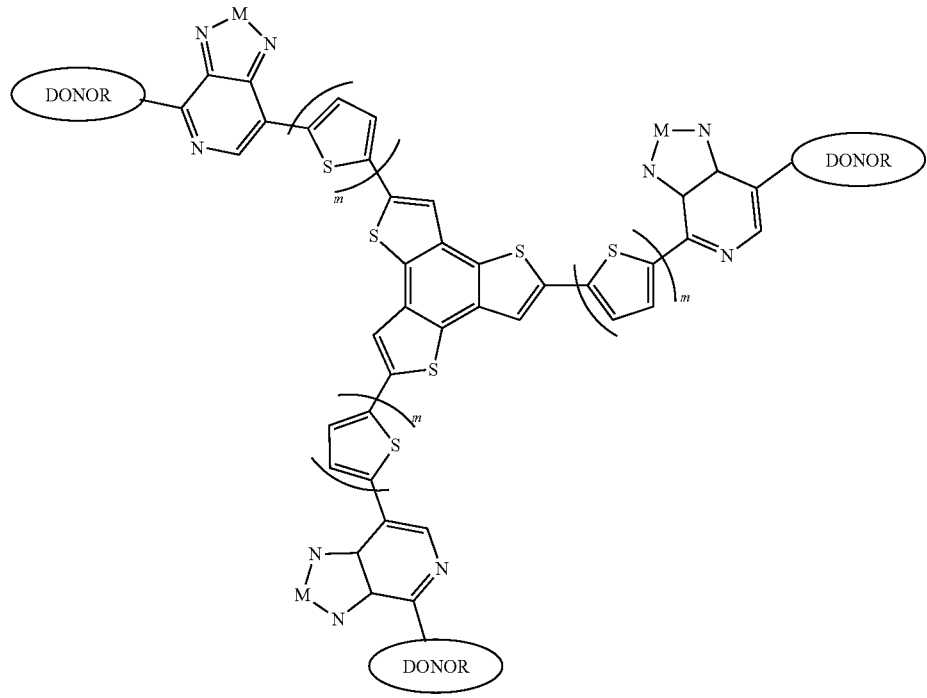

9

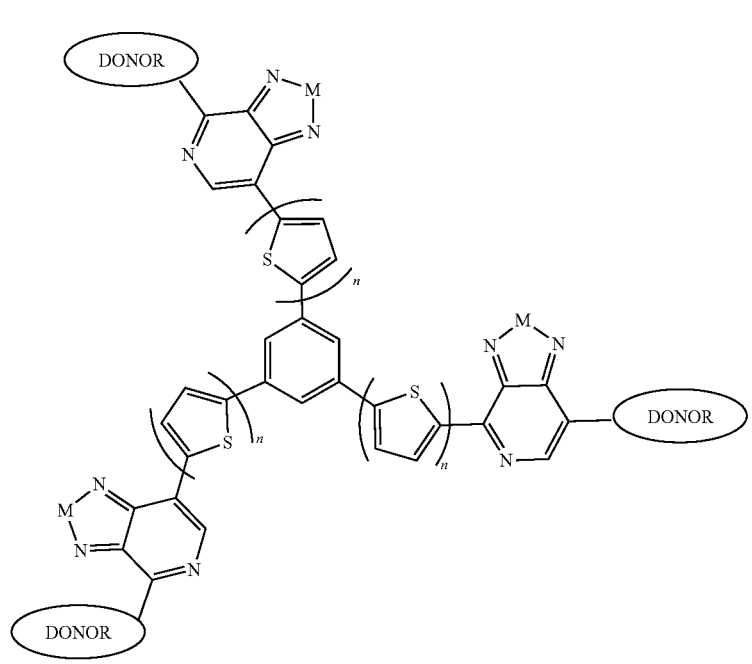

10

In the structures for Formula 9 and Formula 10 above:

M is selected, from sulfur (S), oxygen (O), or N—$R_1$, where $R_1$ is H, $C_1$-$C_{30}$ alkyl or $C_6$-$C_{30}$ aryl;

n is an integer from 1 to 5 inclusive, and m is an integer from 0 to 5 inclusive. In another embodiment, n is 1. In another embodiment, n is 2. In another embodiment, n is 3. In another embodiment, n is 4. In another embodiment, n is 5. In another embodiment, m is 0. In another embodiment, m is 1, In another embodiment, m is 2. In another embodiment, m is 3. In another embodiment, m is 4. In another embodiment, in is 5; and where DONOR is as defined below.

In the structures for Formula 1-2-3-4-5, Formula 1, Formula 2, Formula 3, Formula 4, Formula 5, Formula 6-7-8, Formula 6, Formula 7, Formula 8, Formula 9-10, Formula 9, and Formula 10 above, each DONOR moiety is independently selected from the following group:

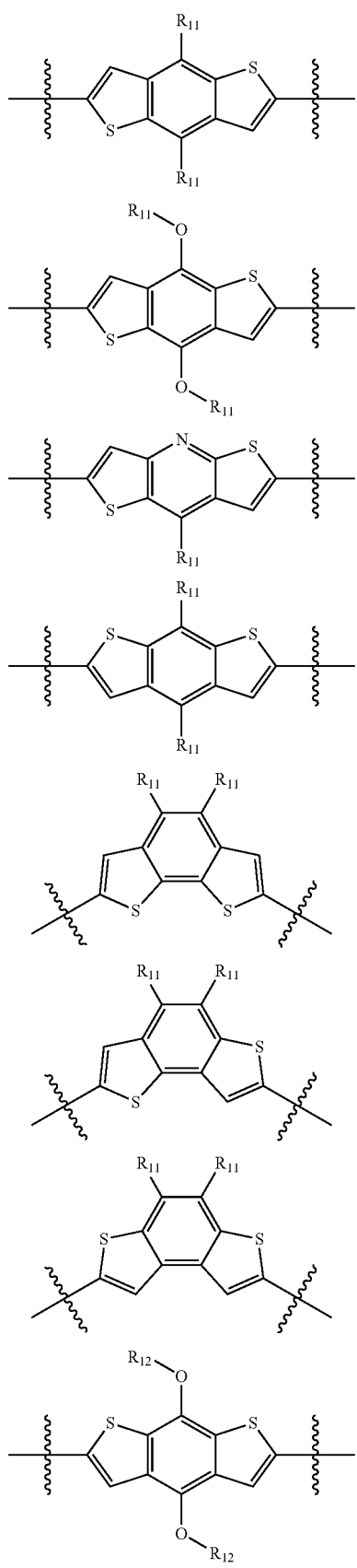
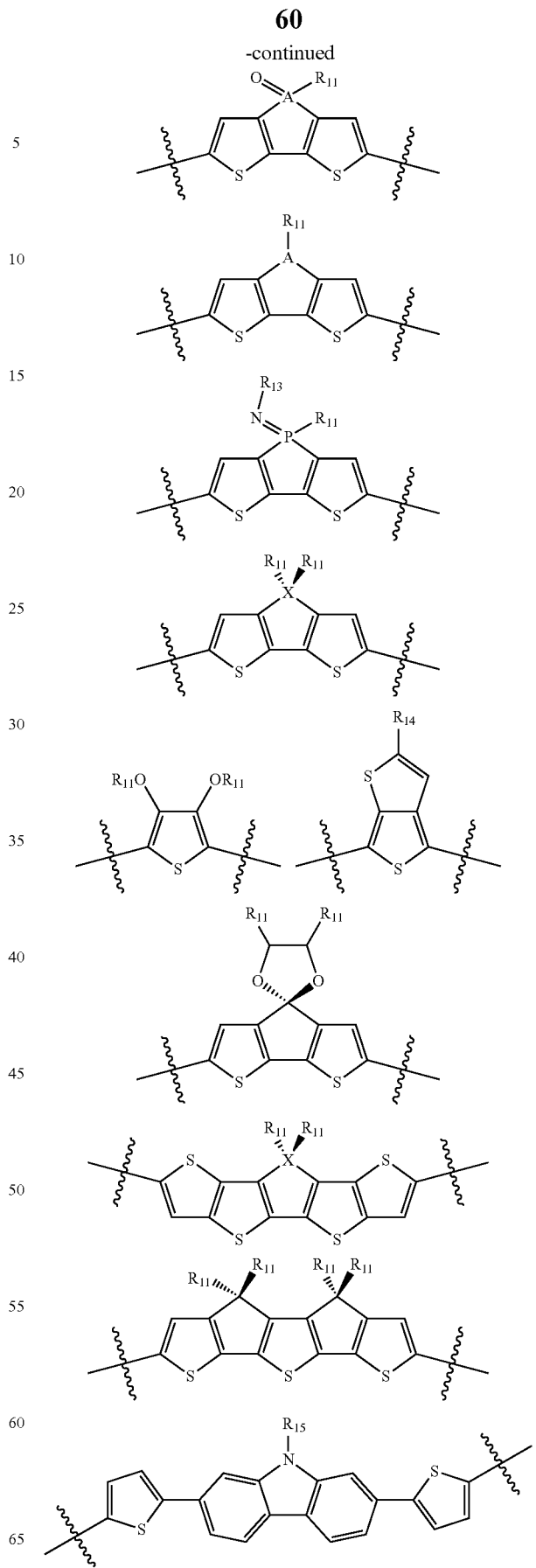

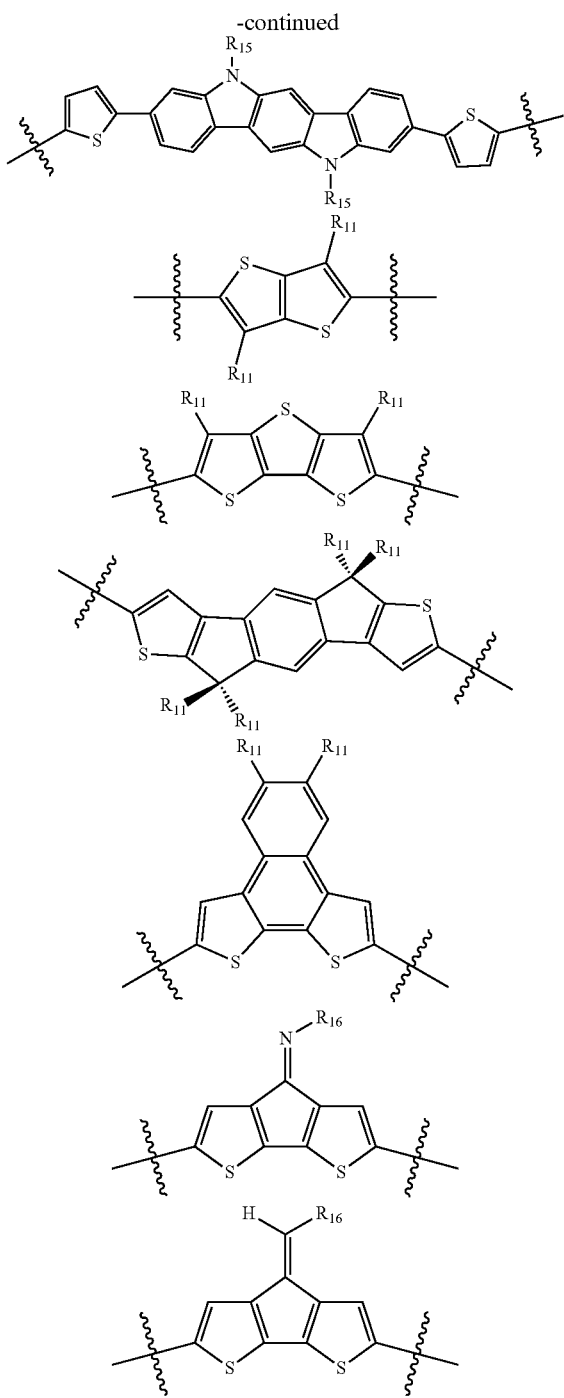

where X is C or Si;
A is N or P;
$R_{11}$ is selected from $C_1$-$C_{16}$ alkyl;
$R_{12}$ is selected from $C_1$-$C_{16}$ alkyl, $C_6$-$C_{20}$ unsubstituted aryl, or $C_6$-$C_{20}$ aryl substituted with one or more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl;
$R_{13}$ is selected from $C_1$-$C_{16}$ alkyl or $C_6$-$C_{20}$ aryl;
$R_{14}$ is selected from $C_1$-$C_{16}$ alkyl, —O—$C_1$-$C_{16}$ alkyl, —C(=O)—O—$C_1$-$C_{16}$ alkyl, or —O—C(=O)—$C_1$-$C_{16}$ alkyl; and
$R_{15}$ is selected from $C_1$-$C_{16}$ alkyl, $C_6$-$C_{20}$ unsubstituted aryl, or $C_6$-$C_{20}$ aryl substituted with one or more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl; and
$R_{16}$ is selected from $C_1$-$C_{16}$ alkyl, $C_6$-$C_{20}$ unsubstituted aryl, or $C_6$-$C_{20}$ aryl substituted with one or more groups selected from —F, $C_1$-$C_{20}$ alkyl, $C_1$-$C_{20}$ fluoroalkyl, —O—$C_1$-$C_{20}$ alkyl, or —$C_1$-$C_{20}$ fluoroalkyl.

In further embodiments, in the structure for Formula 1-2-3-4-5, each DONOR moiety is the same moiety.

In further embodiments, in the structure for Formula 1, each DONOR moiety is the same moiety.

In further embodiments, in the structure for Formula 2, each DONOR moiety is the same moiety.

In further embodiments, in the structure for Formula 3, each DONOR moiety is the same moiety.

In further embodiments, in the structure for Formula 4, each DONOR moiety is the same moiety.

In further embodiments, in the structure for Formula 5, each DONOR moiety is the same moiety.

In further embodiments, in the structure for Formula 6-7-8, each DONOR moiety is the same moiety.

In further embodiments, in the structure for Formula 6, each DONOR moiety is the same moiety.

In further embodiments, in the structure for Formula 7, each DONOR moiety is the same moiety.

In further embodiments, in the structure for Formula 8, each DONOR moiety is the same moiety.

In further embodiments, in the structure for Formula 9-10, each DONOR moiety is the same moiety.

In further embodiments, in the structure for Formula 9, each DONOR moiety is the same moiety.

In further embodiments, in the structure for Formula 10, each DONOR moiety is the same moiety.

In additional embodiments, the invention embraces electronic and optoelectronic devices comprising a non-polymeric compound, said compound incorporating one or more groups of Formula A:

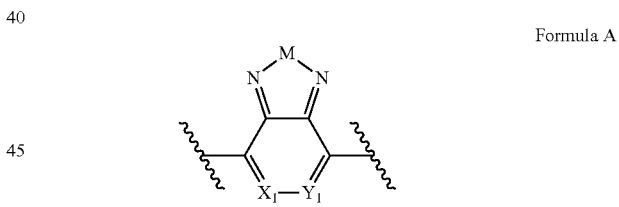

Formula A where said non-polymeric compound is an electron acceptor or is an electron donor in an active layer of the electronic or optoelectronic device, where M is selected from sulfur (S), oxygen (O), or N—$R_1$, where $R_1$ is H, $C_1$-$C_{30}$ alkyl or $C_6$-$C_{30}$ aryl and either $X_1$ is CH and $Y_1$ is N, or $X_1$ is N and $Y_1$ is CH. In one embodiment, where more than one moiety of Formula A is present, M, $X_1$, and $Y_1$ for each moiety is chosen independently of the other moiety or moieties. In another embodiment, where more than one moiety of Formula A is present, M is the same for each moiety, $X_1$ is the same for each moiety, and $Y_1$ is the same for each moiety.

In additional embodiments, the invention embraces electronic and optoelectronic devices comprising, a non-polymeric compound, said non-polymeric compound incorporating a pyridalthiadiazole group, a pyridaloxadiazole group, or a pyridaltriazole group, wherein said non-polymeric compound is an electron acceptor or is an electron donor in an active layer of the electronic or optoelectronic device.

In additional embodiments, the invention embraces electronic and optoelectronic devices utilizing the compounds described above.

In additional embodiments, the invention embraces optoelectronic devices, such as organic solar cells, with the general device architecture using the compounds described above as a light harvesting electron donor, comprising:

1) a first hole-collecting electrode, optionally coated onto a transparent substrate;

2) an optional layer or layers adjacent to the first electrode, such as an electron-blocking, excitors-blocking, or hole-transporting layer;

3) a layer comprising a mixture of an electron acceptor, such as an organic electron acceptor or an inorganic electron acceptor, and an organic non-polymeric electron donor, said donor comprising one or more compounds selected from Formula I, Formula Ia, Formula Ib, Formula Ic, Formula II, Formula IIa, Formula IIb, Formula IIc, Formula III, Formula IIIa, Formula IIIb, Formula IIIc, Formula IIId, Formula IV-V, Formula IV, Formula IVa, Formula IVb, Formula V, Formula Va, Formula Vb, Formula VI-VII, Formula VI, Formula VIa, Formula VIb, Formula VII, Formula VIIa, Formula VIIb, Formula 1-2-3-4-5, Formula 1, Formula 2, Formula 3, Formula 4, Formula 5, Formula 6-7-8, Formula 6, Formula 7, Formula 8, Formula 9-10, Formula 9, or Formula 10;

4) an optional layer or layers such as hole-blocking, exciton-blocking, or electron-transporting layers; and 5) a second electron-collecting electrode.

In additional embodiments, the invention embraces optoelectronic devices, such as organic solar cells, with the general device architecture using the compounds described above as a light harvesting electron acceptor, comprising:

1) a first hole-collecting electrode, optionally coated onto a transparent substrate;

2) an optional layer or layers adjacent to the first electrode, such as an electron-blocking, exciton-blocking, or hole-transporting layer;

3) a layer comprising a mixture of an electron donor, such as an organic electron donor or an inorganic electron donor, and an organic non-polymeric electron acceptor material selected from Formula I, Formula Ia, Formula Ib, Formula Ic, Formula II, Formula IIa, Formula IIb, Formula IIc, Formula III, Formula IIIa, Formula IIIb, Formula IIIc, Formula IIId, Formula IV-V, Formula IV, Formula IVa, Formula IVb, Formula. V, Formula Va, Formula Vb, Formula VI-VII, Formula VI, Formula VIa, Formula VIb, Formula VII, Formula VIIa, Formula VIIb, Formula 1-2-3-4-5, Formula 1, Formula 2, Formula 3, Formula 4, Formula 5, Formula 6-7-8, Formula 6, Formula 7, Formula 8, Formula 940, Formula 9, or Formula 10;

4) an optional layer or layers such as hole-blocking, exciton-blocking, or electron-transporting layers; and 5) a second electron-collecting electrode.

In additional embodiments, the invention embraces devices such as organic field-effect transistors with the general device architecture using the compounds described above as a hole transporting medium, comprising:

1) a dielectric substrate; in one embodiment, this dielectric substrate is Si/SiO$_2$;

2) an optional layer or layers adjacent the dielectric substrate, used to modify the surface energy of the dielectric and/or to facilitate deposition of the active layer; 3) an active layer comprising an organic non-polymeric hole transporting material selected from Formula I, Formula Ia, Formula Ib, Formula Ic, Formula II, Formula IIa, Formula IIb, Formula IIc, Formula III, Formula IIIa, Formula IIIb, Formula IIIc, Formula IIId, Formula IV-V, Formula IV, Formula IVa, Formula IVb, Formula V, Formula Va, Formula Vb, Formula VI-VII, Formula VI, Formula VIa, Formula VIb, Formula VII, Formula VIIa, Formula VIIb, Formula 1-2-3-4-5, Formula 1, Formula 2, Formula 3, Formula 4, Formula 5, Formula 6-7-8, Formula 6, Formula 7. Formula 8, Formula 9-10, Formula 9, or Formula 10; and 4) a metal electrode to facilitate charge injection and collection.

In additional embodiments, the invention embraces devices, such as organic field-effect transistors with the general device architecture using the compounds described above as an electron transporting medium, comprising:

1) a dielectric substrate; in one embodiment, this dielectric substrate is Si; SiO$_2$;

2) an optional layer or layers adjacent the dielectric substrate, used to modify the surface energy of the dielectric and/or to facilitate deposition of the active layer;

3) an active layer comprising an organic non-polymeric electron transporting material selected from Formula I, Formula Ia, Formula Ib, Formula Ic, Formula II, Formula IIa, Formula IIb, Formula IIc, Formula III, Formula IIIa, Formula IIIb, Formula IIIc, Formula IIId, Formula IV-V, Formula IV, Formula IVa, Formula IVb, Formula V, Formula Va, Formula Vb, Formula VI-VII, Formula VI, Formula VIa, Formula VIb, Formula VII, Formula VIIa, Formula VIIb, Formula 1-2-3-4-5, Formula 1, Formula 2, Formula 3, Formula 4, Formula 5, Formula 6-7-8, Formula 6, Formula 7, Formula 8, Formula 9-10, Formula 9, or Formula 10; and 4) a metal electrode to facilitate charge injection and collection.

BRIEF DESCRIPTION OF THE DRAWINGS

FIG. 20 shows data for solar cells fabricated using compound 103. Active layer thickness=75 nm. Thermally annealed devices.

FIG. 22 shows data for solar cells fabricated using compound 103. Active layer thickness=85 nm. Thermally annealed devices.

FIG. 24 shows data for solar cells fabricated using compound 103. Active layer thickness=105 nm. Thermally annealed devices.

Figure 1:
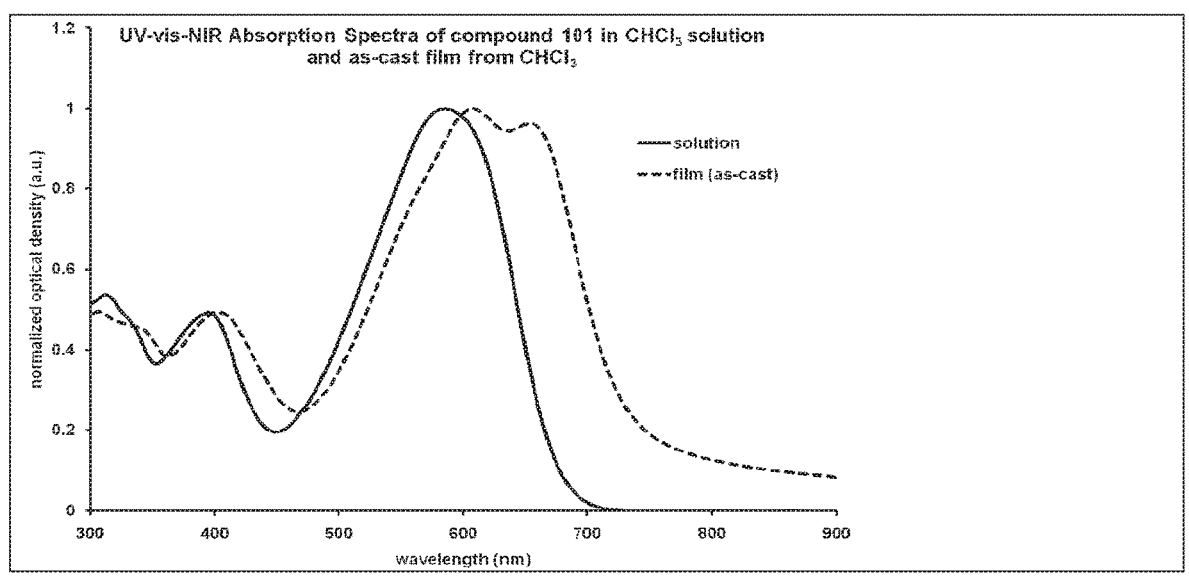
FIG. 1 shows a UV-VIS-NIR absorption spectrum of compound 101 in CHCl$_3$ solution and of a film of compound 101 as-cast from CHCl$_3$ solution.

cyclic hydrocarbon chain(s) and/or ring(s) having at least one carbon-carbon triple bond, and having the number of carbon atoms specified, or if no number is specified, having 2 to 19 carbon atoms, preferably 2 to 16 carbon atoms.

"Fluoroalkyl" indicates an alkyl group where at least one hydrogen of the alkyl group has been replaced with a fluorine substituent.

"Aryl" is defined as an optionally substituted aromatic ring system. Aryl groups include monocyclic aromatic rings, polyaromatic ring systems, and polycyclic aromatic ring systems containing the number of carbon atoms specified, or if no number is specified, containing six to thirty carbon atoms. In other embodiments, aryl groups may contain six to twenty carbon atoms six to twelve carbon atoms, or six to ten carbon atoms. In other embodiments, aryl groups can be unsubstituted.

"Heteroaryl" is defined as an optionally substituted aromatic ring system. Heteroaryl groups contain the number of carbon atoms specified, and one or more heteroatoms (such as one to six heteroatoms, or one to three heteroatoms), where heteroatoms include, but are not limited to, oxygen, nitrogen, sulfur, and phosphorus. In other embodiments, heteroaryl groups may contain six to twenty carbon atoms and one to four heteroatoms, six to twelve carbon atoms and one to three heteroatoms, six to ten carbon atoms and one to three heteroatoms, or three to six carbon atoms and one to three heteroatoms. In other embodiments, heteroaryl groups can be unsubstituted.

"Polymer" or "polymeric molecule" is defined herein as a structure containing at least eight repeating units. A "non-polymeric" molecule is a molecule containing seven or fewer repeating units. Thus, monomers, dimers, trimers, tetramers, pentamers, hexamers, and heptamers are non-polymeric molecules for the purposes of this disclosure. Interruption of a repeating unit "resets" the count of subunits for the purposes of this disclosure; thus, for example, for a molecule such as Formula 6:

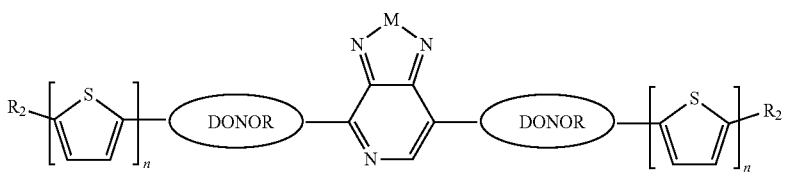

6

DETAILED DESCRIPTION OF THE INVENTION

Definitions

"Alkyl" is intended to embrace a saturated linear, branched, cyclic, or a combination of linear and/or branched and/or cyclic hydrocarbon chains) and/or ring(s) having the number of carbon atoms specified, or if no number is specified, having 1 to 16 carbon atoms.

"Alkenyl" is intended to embrace a linear, branched, cyclic, or a combination of linear and/or branched and/or cyclic hydrocarbon chain(s) and/or ring(s) having at least one carbon-carbon double bond, and having the number of carbon atoms specified, or if no number is specified, having 2 to 16 carbon atoms.

"Alkynyl" is intended to embrace a linear, branched, cyclic, or a combination of linear and/or branched and/or when n is 5, the molecule is considered to have two separate five-subunit pieces, that is, it is comprised of two pentamers of thiophene, and is not considered a decamer or 10-subunit polymer of thiophene.

Non-polymeric molecules typically have a discrete molecular weight, while polymeric molecules typically have a distribution of molecular weights due to varying numbers of monomers that are incorporated into the growing chain during polymerization. Thus, in one embodiment, a preparation of a non-polymeric molecule will be characterized by a single molecular weight (where the molecular weight is averaged only over isotopic variation due to differing isotopes such as hydrogen, deuterium, carbon-12, carbon-13, etc.) of about 90%, preferably 95%, more preferably 98%, still more preferably 99%, of the molecular species. In contrast, preparations of a polymeric molecule will typically have a distribution of molecular weights due to varying numbers of monomers in the final polymer, where the molecular weight is an average over each individual polymeric species present in a given preparation (measured in either number-average molecular weight or weight-average molecular weight).

Small Molecule Chromophores

The current invention provides several advantages for preparation of optoelectronic devices. The organic materials described are non-polymeric allowing for synthesis and purification producers to be more repeatable than organic polymers. Unlike polymers, the organic materials described are discrete mono-disperse small molecules which allows for their exact structure to be known and reproduced. Synthesis of organic small molecule chromophores containing the pyridalthiadiazole (PT, [1,2,5]thiadiazolo[3,4-c]pyridine) organic structure is facile. Preparation of the PT organic structure can be found in M. Leclerc et al. Journal of the American Chemical Society, 2008, 130, 732. The asymmetry of the PT structure induced by the nitrogen atom in the aromatic backbone allows for facile mono-functionalization of the PT structure, forgoing numerous synthetic steps and purification procedures common with related symmetric structures. The organic small molecule chromophores described herein have relatively planar structures allowing for good inter-chromophore interaction, which facilitates charge transfer and transport.

The electronic properties of the pyridalthiadiazole (PT, [1,2,5]thiadiazolo[3,4-c]pyridine) compounds are favorable. The pyridalthiadiazole (PT, [1,2,5]thiadiazolo[3,4-c]pyridine) organic structure has an ideal electron affinity. Donor-acceptor organic materials based on this unit have favorable frontier molecular orbital levels (HOMO and LUMO) to accept and transport holes and electrons. The organic small molecule chromophores described also have favorable frontier molecular orbital levels (HOMO and LUMO) for use as electron donating materials in organic solar cell devices with fullerene, methanofullerene, rylene diimides or related $\pi$ conjugated organic electron acceptors. In addition, the organic small molecule chromophores described have favorable frontier molecular orbital levels (HOMO and LUMO) for use as electron accepting materials in organic solar cell devices with thiophene or phenyl based $\pi$-conjugated organic electron donors.

The optical properties of the pyridalthiadiazole (PT, [1,2,5]thiadiazolo[3,4-c]pyridine) compounds are also very good. The organic small molecule chromophores described have broad absorption spectra that absorb ultraviolet, visible, and near infrared radiation. The absorption spectra of the organic small molecule chromophores described have a favorable spectral overlap with the terrestrial solar spectrum, making them excellent light harvesting materials for organic solar cells.

The compounds are also readily handled in solution, as the organic small molecule chromophores described retain good solubility in many common organic solvents. This allows solution processing during the preparation of the optoelectronic devices.

While solution processing is preferred for its ease of handling and low cost, vapor deposition can also be used for PT, PO, or P3N molecules, or mixtures of said molecules with other components, which are suitable for use in such a method (e.g., vacuum deposition, physical vapor deposition, chemical vapor deposition).

Device Architectures, Materials, and Fabrication

In one embodiment, the optoelectronic device of the invention comprises the following layers:

a) a first hole-collecting electrode, optionally coated onto a transparent substrate;

b) an optional layer or layers adjacent to the first electrode, such as an electron-blocking, exciton-blocking, or hole-transporting layer;

c) a layer comprising a mixture of an electron donor of the general Formula I-VII and an electron acceptor (donor: acceptor);

d) an optional layer or layers such as hole-blocking, exciton-blocking, or electron-transporting layers; and e) a second electron-collecting electrode.

Typically, the first electrode can be transparent, allowing light to enter the device, but in some embodiments, the second electrode can be transparent. In some embodiments, both electrodes are transparent.

Typically, the first electrode (layer "a") is deposited onto a substrate, and the device is fabricated by subsequent deposition of layers "b" (if present), "c", "d" (if present), and "e". However, the second electrode "e" can be deposited onto a substrate, with subsequent deposition of layers "d" (if present), "c", "b" (if present), and "a".

In another embodiment, the optoelectronic device of the invention comprises the following layers:

a) indium tin oxide (ITO) coated onto a transparent substrate (a first electrode), where the transparent substrate can be glass, plastic, or any other transparent material compatible with ITO;

b) poly(3,4-ethylene dioxythiophene:poly(styrenesulfonate) (PEDOT:PSS) or a electron-blocking, exciton-blocking, or hole-transporting metal oxide, including, but not limited to, MoO3, c) a mixture of electron-donating chromophores of the general Formula I-VII, and an electron-acceptor (donor: acceptor), and e) a metal electrode (a second electrode); where layer (d) in the previous embodiment is absent.

Typically, the first electrode (layer "a") is deposited onto the substrate, and the device is fabricated by subsequent deposition of layers "b", "c", and "e". However, the second electrode "e" can be deposited onto a substrate, with subsequent deposition of layers "c", "b", and "a".

The PT, PO, or P3N electron donors or electron acceptors can be used in tandem solar cells, such as those disclosed in US 2009/0126779. Tandem solar cells are arranged so that light which is not absorbed by a first solar cell passes to a second solar cell, where the second solar cell typically has a smaller bandgap than the first solar cell in order to absorb electromagnetic radiation that cannot be usefully absorbed by the first solar cell.

Passivating layers, such as those disclosed in US 2007/0221926 and US 2007/0169816, can be incorporated into devices using the PT, PO, or P3N electron donors or electron acceptors.

Optical spacer layers, such as those disclosed in US 2006/0292736, can also be employed in devices using the PT, PO, or P3N electron donors or electron acceptors.

In one configuration, where light passes though a transparent first electrode (such as ITO-coated glass), it is absorbed by the donor:acceptor mixture, which results in the separation of electrical charges and migration of the charges to the electrodes, yielding a usable electrical potential.

The first electrode can be made of materials such as indium-tin oxide, indium-magnesium oxide, cadmium tin-oxide, tin oxide, aluminum- or indium-doped zinc oxide, gold, silver, nickel, palladium and platinum. Preferably the first electrode has a high work function (4.3 eV or higher). Preferably, the first electrode is transparent.

The optional layer adjacent to the first electrode is preferably polystyrenesulfonic acid-doped polyethylenedioxythiophene (PEDOT:PSS). Other hole transporting materials, such as polyaniline (with suitable dopants), or N,N'-diphenyl-N,N'-bis(3-methylphenyl)[1,1'-biphenyl]-4,4-'-diamine (TPD), nickel oxide, can be used. Electron-blocking, exciton-blocking, or hole-transporting metal oxides, such as $MoO_3$, $MoO_{3-x}$, $V_2O_{5-x}$, NiO, $Ta_2O_5$, $Ag_2O$, CuO, $Cu_2O$, $CrO_{3-x}$, and $WO_3$, where x is between 0.01 and 0.99, more preferably between 0.1 and 0.9, can be used as materials between the hole-transporting electrode and the active layer. Other suitable materials are described in Greiner, Mark T. et al., "Universal energy-level alignment of molecules on metal oxides," Nature Materials, DOI: 10.1038/NMAT3159 (Nov. 6, 2011).

One method of fabricating the optoelectronic device is as follows: A conductive, transparent substrate is prepared from commercially available indium tin oxide-coated glass and polystyrenesulfonic acid doped polyethylenedioxythiophene using standard procedures. A solution containing a mixture of the donor and acceptor materials is prepared so that the ratio of donor to acceptor is between 1:99 and 99:1 parts by mass; more preferably between 3:7 and 7:3 parts by mass. The overall concentration of the solution may range between 0.1 mg/mL, and 100 mg/mL, but is preferably in the range of 10 mg/mL and 30 mg/mL. In in one embodiment of the invention, PT, PO, or P3N non-polymeric molecules are used that have a solubility of at least about 0.1 mg/mL in an organic solvent, 1 mg/mL in an organic solvent, 5 mg/mL, 10 mg/mL in an organic solvent, 30 mg/mL in an organic solvent, or 100 mg/mL in an organic solvent. The organic solvent can be selected from chloroform, toluene, chlorobenzene, methylene dichloride, tetrahydrofuran, or carbon disulfide.

The electron acceptor is preferably [6,6]-phenyl C61-butyric acid methyl ester (PCBM), but may be a different fullerene (including, but not limited to, C71-PCBM), a tetracyanoquinodimethane, a vinazene, a perylene, tetracarboxylic acid-dianhydride, a perylene tetracarboxylic acid-diimide, an oxadiazole, carbon nanotubes, or any other organic electron acceptor, such as those compounds disclosed in U.S. 2008/0315187.

In other embodiments, the electron acceptor is an inorganic acceptor selected from $TiO_2$ (titanium dioxide), $TiO_x$ (titanium suboxide, where x<2) and ZnO (zinc oxide). The titanium dioxide can be anatase, rutile, or amorphous. A titanium dioxide layer can be prepared by depositing a sol-gel precursor solution, for example by spincasting or doctorblading, and sintering at a temperature between about 300° C. and 500° C. When an inorganic layer is used, component (c) of the optoelectronic device described above can be comprised of a layer of electron-donating chromophores of the general Formula I-VII and an inorganic electron-acceptor layer. Alternatively, the inorganic material can be dispersed in the electron-donating chromophores to create a single layer. Preparation of $TiO_2$ for use in solar cells is described in Brian O'Regan & Michael Grätzel, Nature 353:737 (1991) and Scrap Günes et al., 2008 Nanotechnology 19 424009.

When titanium suboxide according to the formula $TiO_x$ where x<2, is used, x is preferably 1<x<1.98, 1.1<x<1.9, 1.2<x<1.8, or 1.3<x<1.8. X in the formula $TIO_x$ can be <2, <1.98, <1.9, <1.8, <1.7, or <1.6.

Useful solvents include chloroform, toluene, chlorobenzene, methylene dichloride, tetrahydrofuran, and carbon disulfide. However, the solvent used may be any solvent which dissolves or partially dissolve both donor and acceptor materials and has a non-zero vapor pressure.

The solution of donor and acceptor is deposited by spin casting, doctor-blading, ink-jet printing, roll-to-roll coating, slot-dye coating, gravure coating, or any process which yields a continuous film of the donor-acceptor mixture such that the thickness of the film is within the range of 10 to 1000 nm, more preferably between 50 and 150 nm.

In certain embodiments, the layer of the donor and acceptor is cast from a solution comprising a solvent and the electron donor and the electron acceptor. The solvent can comprise chloroform, thiophene, trichloroethylene, chlorobenzene, carbon disulfide, a mixture of any of the foregoing solvents or any solvent or solvent mixture that dissolves both the donor and acceptor organic small molecule. The solvent can also include processing additives, such as those disclosed in US Patent Application Publication Nos. 2009/0032808, 2008/0315187, or 2009/0108255. For example, 1,8-diiodooctane (DIO) can be added to the solvent/donor/acceptor mixture in an amount of 0.1-10% by volume. The additive, such as 2% DIO, can be added to any organic solvent used to cast the layer of donor/acceptor, such as chloroform. The solvent can also include doping agents such as molybdenum trioxide ($MoO_3$). For example, $MoO_3$ can be added to the solvent/donor/acceptor mixture in an amount of 0.1-10% by volume.

An additional layer or layers of material (i.e., the layer(s) adjacent to the second electrode) may optionally be deposited on top of the donor-acceptor film in order to block holes or excitons, act as an optical buffer, or otherwise benefit the electrical characteristics of the device. 2,9-dimethyl-4,7-diphenyl-1,10-phenanthroline can act as a hole-blocking or exciton-blocking material, while 4,4'4"-tris[N-(3-methylphenyl)-N-phenylamino]triphenylamine, and polyethylene dioxythiophene can act as exciton-blocking materials. Other materials that can be used between the second electrode and the active layer are titanium suboxide, ZnO, $Cs_2CO_3$, and $ZrO_3$. Additional materials suitable for use are described in Greiner, Mark T. et al., "Universal energy-level alignment of molecules on metal oxides," Nature Materials, DOI: 10.1038/NMAT3159 (Nov. 6, 2011).

Finally, an electrode, such as a metal electrode, is deposited on top of the structure by thermal evaporation, sputtering, printing, lamination or some other process. Conducting metal oxides, such as indium tin oxide, zinc oxide, or cadmium oxide, can also be used as electrodes, as well as conducting organic materials, such as electrodes comprising graphene. For metal electrodes, the metal is preferably aluminum, silver or magnesium, but may be any metal. Nanowires such as silver nanowires can also be used. If a transparent electrode is desired, very thin metallic sheets of metals can also be used. In some embodiments, the device is annealed before and/or after evaporation of the metal electrode.

Hole and electron mobilities are important parameters to consider in the fabrication/function of bulk heterojunction solar cells. For optimal device performance, a balance in the mobility of both charge carriers is desirable. Preferably, the electron and hole mobilities are both on the order of $10^{-4}$ cm$^2$/Vs or higher. More preferably, the electron mobilities are on the order of $10^{-3}$ cm$^2$/Vs or higher. In some embodiments, the electron mobilities are on the order of $10^{-4}$ cm$^2$/Vs or higher, and the hole mobilities are between $10^{-8}$ cm$^2$/Vs and $10^{-4}$ cm$^2$/Vs or higher. In other embodiments, the electron mobilities are on the order of $10^{-3}$ cm$^2$/Vs or higher, and the hole mobilities are between $10^{-8}$ cm$^2$/Vs and $10^{-4}$ cm$^2$/Vs or higher.

Optoelectronic devices of the present invention have excellent photovoltaic properties. In some embodiments, the power conversion efficiency (PCE) is at least 0.5%, at least 1.0%, at least 2.0%, or at least 3.0%. In some embodiments, the short circuit current density is greater than 3.0 mA/cm$^2$, and preferably greater than 8 mA/cm$^2$. In some embodiments, the open circuit voltage is between 0.3 and 1.0 V or higher. In some embodiments, the device exhibits an external quantum efficiency of approximately 35% or greater between 300 and 800 nm.

The morphological properties of the donor:acceptor films can be measured using atomic force microscopy or other surface-sensitive techniques. Preferably, the films will have a root-mean-squared surface roughness of less than 1.0 nm, more preferably less than 0.5 nm.

For embodiments of the devices using an inverted device architecture, the first electrode can comprise Au or another material having a work function higher than the work function of the second electrode, while the second electrode can comprise an ITO substrate modified using a self-assembled monolayer of 3-aminopropyltrimethoxysiloxane or another material having a work function lower than the work function of the first electrode.

EXAMPLES

General Experimental Procedures

General Data: Preparations were carried out on a bench top or under an atmosphere of dry, O$_2$-free N$_2$ employing both Schlenk line techniques and a Vacuum Atmospheres inert atmosphere glove box. Solvents (toluene, xylenes) were dried over sodium/benzophenone, distilled under vacuum, and stored over molecular sieves (4 Å). Solvents (chloroform) were dried over calcium hydride, distilled under vacuum, and stored over molecular sieves (4 Å). Molecular sieves (4 Å) were purchased from Aldrich Chemical Company and dried at 140° C. tinder vacuum for 24 hours prior to use. Deuterated solvents were dried over CaH$_2$ (CDCl$_3$) All reactants and reagents are commercially available and used as received unless otherwise noted.

Materials: Compound 5,5'-Bis(trimethylstannyl)-3,3'-di-2-ethylhexylsilylene-2,2'-bithiophene {DTS(SnMe$_3$)$_2$} (Hou, J. H.; Chen, H. Y.; Chang, S. Q.; Li, G.; Yang, Y. *Journal of the American Chemical Society* 2008, 130, 16144-16145) and 5'-Hexyl-2,2'-bithiophene-5-trimethylstannane (Parab, K.; Venkatasubbaiah, K.; Jakle, F. *Journal of the American Chemical Society* 2006, 128, 12879-12885) were prepared by methods similar to those reported in the literature. Compounds 5,5'-dibromo-3,3'-di-2-ethylhexylsilylene-2,2'-bithiophene (DTS-Bin) and 4,7-dibromo-pyridal[2,1,3]thiadiazole (PTBr$_2$) were purchased from Luminescence Technology Corp. (Lumtec) and used as received.

NMR: $^1$H and $^{13}$C nuclear magnetic resonance (NMR) spectroscopy spectra were recorded on a Bruker Avance-500 MHz spectrometer at 25° C. unless otherwise noted. $^1$H and $^{13}$C NMR spectra are referenced to SiMe$_4$ using the residual solvent peak impurity of the given solvent. Chemical shifts are reported in ppm and coupling constants in Hz as absolute values. DEPT, $^1$H-$^1$H and $^1$H-$^{13}$C correlation experiments were completed for assignment of the carbon atoms. $^1$H-$^1$H NOE experiments were carried out with a mixing time of 0.8 seconds.

UV-vis-nearIR: UV-visible spectra were recorded using either a Beckman Coulter DU 800 series or Perkin Elmer Lambda 750 spectrophotometer at room temperature unless otherwise noted. All solution UV-vis experiments were run in CHCl$_3$ under an N$_2$, atmosphere in Teflon-capped 1 mm quartz cuvettes. Films were prepared by spin-coating a 1% (w/w) solution of a compound of the invention, or a compound of the invention with PC$_{71}$BM, from CHCl$_3$ onto quartz substrates.

CHN: Combustion analyses were performed by the MST analytical lab at the University of California, Santa Barbara.

Electrochemistry: All electrochemical measurements were performed using CHI instrument model 730B in a standard three-electrode, one compartment configuration equipped with Ag/AgCl electrode, Pt wire and Glassy carbon electrode (dia, 3 mm), as the pseudo reference, counter electrode and working electrode respectively. Glassy carbon electrodes were polished with alumina. The cyclic voltammetry (CV) experiments were performed in anhydrous acetonitrile (AcCN) solution with 0.1 M tetrabutylammonium hexafluorophosphate (TBAPF$_6$) as the supporting electrolyte at scan rate 100 mV/s unless otherwise stated. All electroChemical solutions were purged with dry Ar for 15 minutes at least to deoxygenate the system. Under these conditions, a Fc/Fc$^+$ standard was calibrated to be 0.48 V. A mixture of small molecule in dry CHCl$_3$ (~3 ma/mL) was used for preparation films at room temperature. Films were prepared by drop-cast onto Glassy carbon electrode for CV measurement.

Example 1

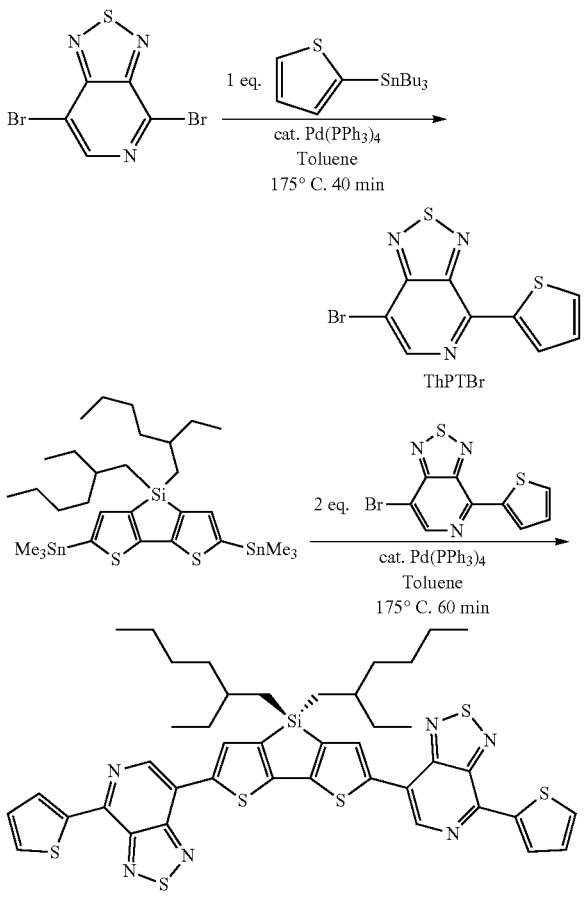

101

Synthesis of 7-bromo-4-thienyl[1,2,5]thiadiazolo[3,4-c] pyridine (ThPTBr): A 20 mL microwave tube was charged with 4,7-dibromo-pyridal[2,1,3]thiadiazole (PTBr$_2$, 1.51 g, 5.12 mmol), 2-(tributylstanayl)thiophene (Bu$_3$Sn—Th, 1.99 g, 5.33 mmol), Pd(PPh$_3$)$_4$. (0.050 g, 0.04 mmol), toluene (10 mL), and sealed with a Teflon® cap. The reaction mixture was heated to 120° C. for 3 minutes, 140° C. for 3 minutes, and 175° C. for 40 minutes, using a Biotage microwave reactor. Upon cooling, the residue was passed through a short silica plug eluting with CH$_2$Cl$_2$ (500 mL). All volatiles were removed in vacuo to give the crude product as an orange solid. The solid was slurried in MeOH (300 mL), sonicated for 10 minutes, and filtered. The solid was washed with copious amounts of MeOH and then dried under vacuum for 24 hours. The product was collected as an orange solid. Recovered yield: 920 mg (60%).

$^1$H NMR (CD$_2$Cl$_2$): δ 8.67 (dd, $^3J_{H-H}$=4 Hz, $^4J_{H-H}$=1 Hz, 1H, Th-CH), 8.63 (s, 1H, PT-CH), 7.64 (dd, $^3J_{H-H}$=4 Hz, $^4J_{H-H}$=1 Hz 1H, Th-CH), 7.26 (dd, $^3J_{H-H}$=5 Hz. $^3J_{H-H}$=4 Hz 1H, Th—CH), $^{13}$C{$^1$H}NMR (CD$_2$Cl$_2$): 156.90, 148.46, 147.96 (s, quaternary), 146.18 (s, CH), 141.65 (s, quaternary), 133.09 (s, CH), 131.74 (s, CH), 129.57 (s, CH), 108.91 (s, quaternary). Anal. Calcd. for C$_9$H$_4$BrN$_3$S$_2$: C, 36.25; H, 1.35; N. 14.09. Found: C, 36.6; H, 1.35; N, 13.8%. HRMS (EI) m/z, calcd for C$_{13}$H$_7$N$_3$S$_3$ (M$^+$): 298.9; found: 299.

Synthesis of 101: A 20 mL microwave tube was charged with 5,5'-Bis(trimethylstannyl)-3,3'-Di-2-ethylhexylsi-lylene-2,2'-bithiophene (M$_3$Sn—SD$_{TEH}$-SnM$_{e3}$, 961 mg, 1.29 mmol), 7-bromo-4-thienyl[1,2,5]thiadiazolo[3,4-c] pyridine (ThPTBr, 770 mg, 2.58 mmol), Pd(PP$_3$)$_4$ (0.050 g, 0.04 mmol), toluene (15 mL), and sealed with a Teflon® cap. The reaction mixture was heated to 12° C. for 3 minutes, 14° C. for 3 minutes, and 17° C. for 60 minutes, using a Biotage microwave reactor. Upon cooling, the residue was passed through a short silica plug eluting with CHC$_{13}$. (5% E$_{t3}$N) (500 mL). All volatiles were removed in vacuo to give the crude product as a purple solid. The material was then loaded onto silica and purified by flash chromatography using a hexanes/CHCl$_3$ (5% E$_{t3}$N) gradient. After fraction collection and solvent removal a purple solid was obtained. The solid was slurried in MeOH (300 mL), sonicated for 10 minutes, and filtered. The solid was washed with copious amounts of MeOH and then dried under vacuum for 24 hours. The product was collected as purple solid. Recovered yield: 980 mg (88%). $^1$H NMR (C$_{D2}$C$_{12}$); δ 8.74 (s, 2H, PT-CH), 8.63 (d, $^3J_{H-H}$=4 Hz, 2H Th-CH), 8.25 (t, 2H, SDT-CH), 7.60 (d, $^3J_{H-H}$=4 Hz, 2H Th-CH), 7.27 (dd, $^3J_{H-H}$=5 Hz, $^3J_{H-H}$=4 Hz 2H, Th-CH), 1.59 (h, $^3J_{H-H}$=6 Hz, 2H, CH), 1.38 (m, 4H, C$_{H2}$), 1.32 (m, 4H, C$_{H2}$), 1.25 (m, 8H, C$_{H2}$), 1.16 (m, 4H, SiC$_{H2}$), 0.86 (t, $^3J_{H-H}$=8 Hz, 6H, C$_{H3}$), 0.83 (t, $^3J_{H-H}$=8 Hz, 6H, C$_{H3}$). $^{13}$C{$^1$H}NMR (C$_{D2}$C$_{12}$): 155.06, 151.01, 148.44, 145.97, 142.57 (s, quaternary), 140.42 (s, CH), 139.02, 132.07 (s, CH), 131.79 (s, SDT-CH), 130.81 (s, CH), 129.37 (s, CH), 121.39 (s, quaternary), 36.70 (s, CH), 36.40 (s, SiC$_{H2}$), 29.59 (s, 2×C$_{H2}$), 23.62 (s, C$_{H2}$), 18.28 (s, C$_{H2}$), 14.54 (s, C$_{H3}$), 11.24 (s, C$_{H3}$) Anal. Calcd. for $_{c42}H_{44}N_6S_6$Si: C, 59.12; H, 5.20; N, 9.85. Found: C, 59.0; H, 4.31; N, 9.32%. HRMS (EI) m/z, calcd for $_{c42}H_{44}N_6S_6$Si ($^{M+}$): 852; found: 852. Absorbance: (CHC$_{13}$) λ$_{max}$=582 nm, λ$_{onset}$=678 nm. (As Cast Film) λ$_{max}$=604, 652 nm, λ$_{onset}$=736 nm.

The UV-VIS-NIR absorption spectrum of 101 in CHCl$_3$ solution and of a film of 101 as-cast from CHCl$_3$ solution is shown in FIG. 1.

Example 2

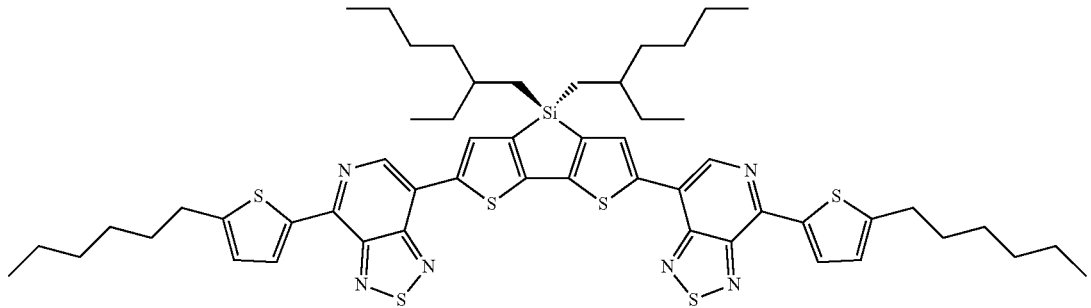

102

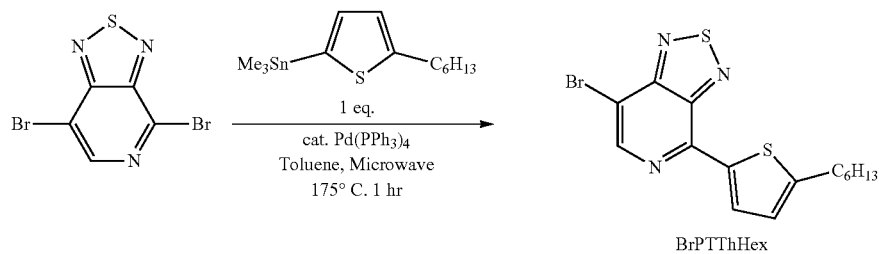

BrPTThHex

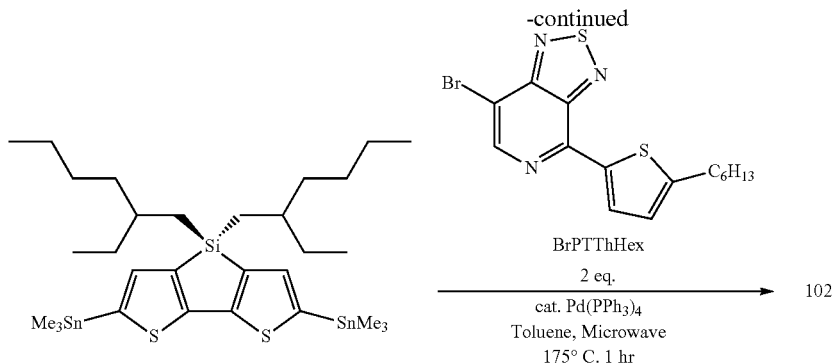

Synthesis of 7-bromo-4-(5-hexylthiophen-2-yl)-[1,2,5]thiadiazolo[3,4-c]pyridine (HexThPTBr): In a $N_2$ filled glove box a 20 mL glass tube was charged with 4,7-dibromo-pyridal[2,1,3]thiadiazole ($PTBr_2$, 1.41 g, 4.78 mmol), (5-hexylthiophen-2-yl)trimethylstannane (1.58 g, 4.78 mmol), $Pd(PPh_3)_4$ (0.025 g, 0.02 mmol), toluene (15 mL), and sealed with a Teflon® cap. The reaction mixture was heated to 120° C. for 3 minutes, 140° C. for 3 minutes, and 175° C. for 30 minutes, using a Biotage microwave reactor. Upon cooling, the residue was passed through a short silica plug eluting with $CHCl_3$ (5% $Et_3N$) (500 mL), All volatiles were removed in vacuo to give the crude product as a red tacky solid. MeOH (100 mL) was added and the mixture sonicated for 5 minutes, followed by removal of MeOH in vacuo. The product was then slurried in MeOH (200 mL), filtered, washed with MeOH (200 mL), and dried under high vacuum for 24 hours. The product was collected as red solid. Recovered yield: 1.7 mg (94%), $^1H$ NMR ($CDCl_3$): δ 8.62 (s, 1H, PT-CH), 8.51 (d, 1H, $^3J_{H-H}$=5 Hz, Th-CH), 6.94 (d, 1H, $^3J_{H-H}$=5 Hz, Th-CH), 2.90 (t, 2H, $^3J_{H-H}$=8 Hz, Th-$CH_2$), 1.71 (tt, 2H, $^3J_{H-H}$=8 Hz, $CH_2$), 1.42 (br m, 2H, $CH_2$), 1.33 (br m, 4H, $CH_2$), 0.90 (m, 3H, $^3J_{H-H}$=8 Hz, $CH_3$). $^{13}C\{^1H\}$NMR ($CDCl_3$): 156.31, 153.21, 147.92, 47.65 (s, quaternary), 145.82 (s, CH), 138.19 (s, quaternary), 133.15, 126.56 (s, CH), 107.48 (s, quaternary), 31.53 (s, $CH_2$), 31.36 (s, $CH_2$), 30.58 (s, $CH_2$) 28.75 (s, $CH_2$), 22.54 (s, $CH_2$), 14.05 (s, $CH_3$). Anal. Calcd. for $C_{15}H_{16}BrN_3S_2$: C, 47.12; H, 4.22; N, 10.99. Found: C, 47.4; H, 4.03; N, 10.6%.

Synthesis of 102: In a $N_2$ filled glove box a 20 mL microwave tube was charged with 5,5'-Bis(trimethylstannyl)-3,3'-di-2-ethylhexylsilylene-2,2'-bithiophene ($Me_3Sn$-$SDT_{EH}$-$SnMe_3$, 510 mg, 0.68 mmol), 7-bromo-4-(5-hexylthiophen-2-yl)-[1,2,5]thiadiazolo[3,4-c]pyridine (HexThPTBr, 574 mg, 1.50 mmol.), $Pd(PPh_3)_4$ (0.025 g, 0.02 mmol), toluene (15 mL), and sealed with a Teflon® cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with $CHCl_3$ (5% $Et_3N$) (500 mL). All volatiles were removed in vacuo to give the crude product as a purple solid. The material was then loaded onto silica and purified by flash chromatography using a hexanes/$CHCl_3$ (5% $Et_3N$) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 562 mg (80%). $^1H$ NMR ($CDCl_3$): δ 8.70 (s, 2H, PT-CH), 8.43 (d, $^3J_{H-H}$=5 Hz, 2H, Th-CH), 8.18 (t, 2H, SDT-CH), 6.93 (d, $^3J_{H-H}$=5 Hz, 2H, Th-CH), 2.92 (t, $^3J_{H-H}$=7 Hz, 4H Th-$CH_2$), 1.79 (tt, $^3J_{H-H}$=7 Hz, 4H, $CH_2$), 1.59 (br m, 2H, CH), 1.44 (br m, 4H, $CH_2$), 1.35 (m, 14H, $CH_2$), 1.25 (m, 8H, $CH_2$), 1.19-1.08 (m, 4H, Si$CH_2$). 0.92 (m, 6H, $CH_3$), 0.88-0.83 (m, 12H, $CH_3$). $^{13}C\{^1H\}$ NMR ($CDCl_3$): 154.51, 152.09, 150.27, 147.90, 145.05 (s, quaternary), 140.09 (s, CH), 139.23, 138.53 (s, quaternary), 132.03 (s, CH), 130.88 (s, CH), 126.40 (s, CH, 120.22 (s, quaternary), 36.08 (s, CH). 35.83 (s, $CH_2$), 31.61 (s, Si$CH_2$), 31.45 (s, $CH_2$), 30.62 (s, Th$CH_2$), 29.05 (s, $CH_2$), 28.98 (s, $CH_2$), 28.83 (s, $CH_2$), 23.08 (s, $CH_2$), 22.60 (s, $CH_2$), 17.79 (s, $CH_2$), 14.24 (s, $CH_3$), 14.10 (s, $CH_3$), 10.89 (s, $CH_3$), Anal. Calcd. for $C_{54}H_{68}N_6S_6Si$: C, 63.48; H, 6.71; N, 8.23. Found: C, 63.5; H, 6.65; N, 8.20%. Absorbance: ($CHCl_3$) $\lambda_{max}$=600 nm, $\lambda_{onset}$=700 nm. (As Cast Film) $\lambda_{max}$=620, 670 nm, $\lambda_{onset}$=760 nm.

Figure 2:
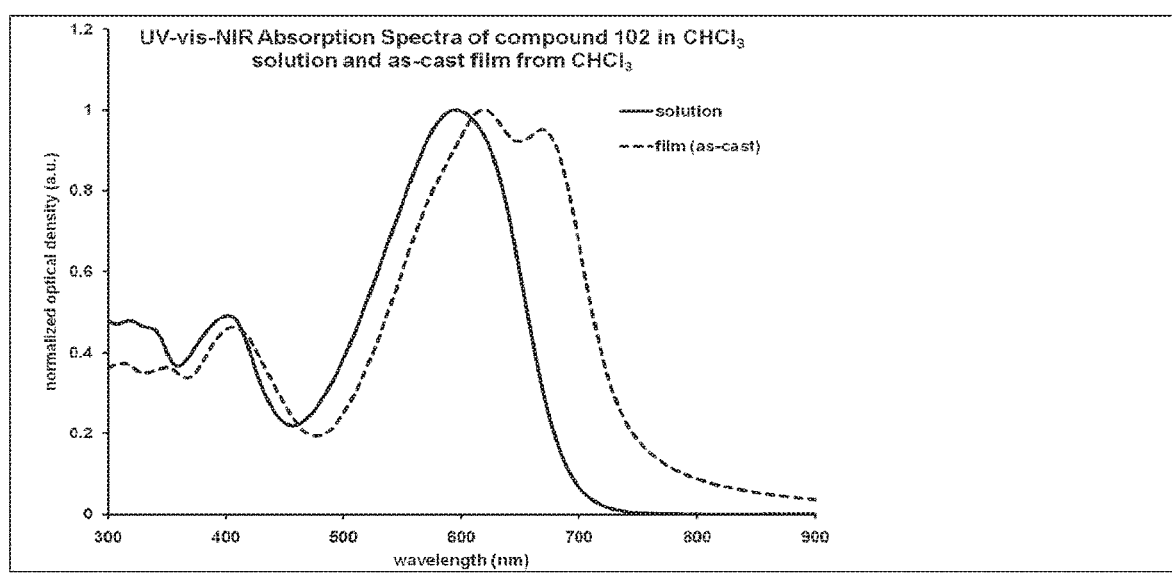
FIG. 2 shows a UV-VIS-NIR absorption spectrum of compound 102 in CHCl$_3$ solution and of a film of compound 102 as-cast from CHCl$_3$ solution.

The UV-VIS-NIR absorption spectrum of 102 in $CHCl_3$ solution and of a film of 102 as-cast from $CHCl_3$ solution is shown in FIG. 2.

Example 3

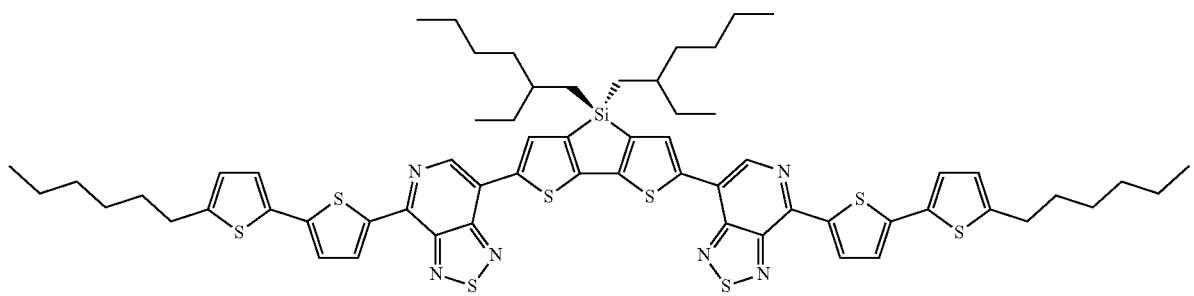

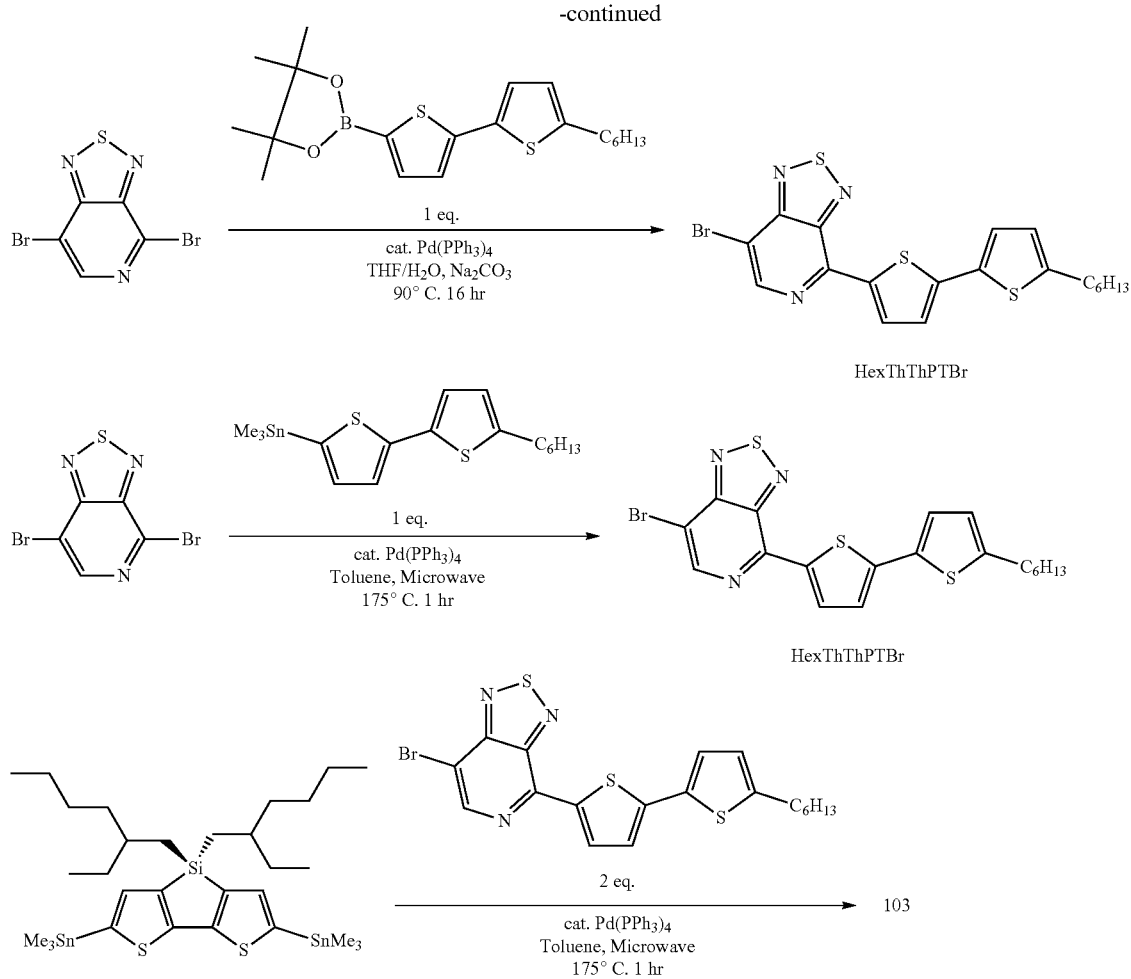

HexThThPTBr

HexThThPTBr

103

Synthesis of 7-bromo-4-5-(5-hexylthiophen-2-yl)thiophen-2-yl)-[1,2,5]thiadiazolo[3,4-c]pyridine (HexThThPTBr): Suzuki: In a $N_2$ filled glove box a 20 mL glass tube was charged with 4,7-dibromo-pyridal[2,1,3]thiadiazole ($PTB_2$, 550 mg, 1.86 mmol), $Na_2CO_3$ (1 g), $Pd(PPh_3)_4$ (0.050 g, 0.04 mmol), anhydrous THF (10 mL), and sealed with a Teflon® cap. To this mixture was added de-gassed de-ionized water (5 mL) under Ar and the mixture stirred for 5 minutes. 5'-Hexyl-2,2'-bithiophene-5-boronic acid pinacol ester (773 mg, 2.05 mmol) in anhydrous THF (5 mL) was then added to the reaction mixture which was subsequently purged with Ar for 5 minutes. The reaction mixture was heated to 90° C. and vigorously stirred for 16 hours. Upon cooling the reaction mixture was poured into 500 mL of a 1:1 MeOH/$H_2O$ solution and stirred for 20 minutes. The precipitate that formed was collect by filtration and washed with 500 mL of a 2:1 MeOH/$H_2O$ solution and 100 mL of MeOH. The crude product was purified, by flash chromatography eluting with a hexanes/$CHCl_3$ gradient. After fraction collection and solvent removal the resulting red solid was dried under high vacuum for 48 hours. The product was collected as red solid. Recovered yield: 555 mg (65%). Stille: In a $N_2$ filled glove box a 5 mL glass tube was charged with 4,7-dibromo-pyridal[2,1,3]thiadiazole ($PTB_2$, 550 mg, 1.86 mmol), 5'-Hexyl-2,2'-bithiophene-5-trimethylstannane (770 mg, 1.86 mmol), $Pd(PPh_3)_4$ (0.025 g, 0.02 mmol), toluene (4 mL), and sealed with a Teflon® cap. The reaction mixture was heated to 120° C. for 3 minutes, 140° C. for 3 minutes, and 175° C. for 25 minutes, using a Biotage microwave reactor. Upon cooling, the residue was passed through a short silica plug eluting with $CHCl_3$ (5% $Et_3N$) (500 mL). All volatiles were removed in vacuo to give the crude product as a red solid. The product was slurried in MeOH (200 mL), filtered, washed with MeOH (20 mL), and dried under high vacuum for 24 hours. The product was collected as red solid. Recovered yield: 750 mg (87%), $^1H$ NMR ($CDCl_3$): δ 8.62 (s, 1H, PT-CH), 8.56 (d, 1H, $^3J_{H-H}$=5 Hz, Th—CH), 7.21 (m, 1H, Th-CH), 7.17 (m, 1H, Th-CH), 6.74 (m, Th-CH), 2.83 (d, 2H, $^3J_{H-H}$=8 Hz, Th-$CH_2$), 1.71 (m, 2H. $CH_2$), 1.41 (m, 2H, $CH_2$), 1.33 (m, 4H, $CH_2$), 0.92 (m, 3H, $CH_3$). $^{13}C\{^1H\}$ NMR ($CDCl_3$): 147.44, 147.26 (s, quaternary), 145.85 (s, CH), 143.86, 138.48, 134.32 (s, quaternary), 133.79 (s, CH), 128.63 (s, quaternary), 125.00, 124.58 (5, CH), 124.07 (s, quaternary), 31.57 (5, $CH_2$), 31.52 (s, $CH_2$), 30.30 (s, $CH_2$), 28.80 (s, $CH_2$), 22.61 (s, $CH_2$), 14.12 (s, $CH_3$), Anal. Calcd. for $C_{19}H_{18}BrN_3S_3$: C, 49.13; H, 3.91; N, 9.05, Found: C, 48.8; H, 3.60; N, 9.01%.

Synthesis of 103: In a $N_2$ filled glove box a 20 mL microwave tube was charged with 5,5'-Bis(trimethylstannyl)-3,3'-Di-2-ethylhexylsilylene-2,2'-bithiophene ($Me_3Sn$-$SDT_{EH}$-$SnMe_3$, 617 mg, 0.83 mmol), 7-bromo 4-(5-(5 hexylthiophen-2-yl)thiophen-2-yl)-[1,2,5]thiadiazolo[3,4-c] pyridine (HexThThPTBr, 770 Mg, 1.66 mmol), $Pd(PPh_3)_4$ (0.025 g, 0.02 mmol), toluene (15 mL), and sealed with a Teflon® cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with CHCl$_3$ (5% Et$_3$N) (500 mL). All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 700 mg (71%). $^1$H NMR (CDCl$_3$): δ 8.79 (s, 2H, PT-CH), 8.55 (d, $^3J_{H-H}$5 Hz, 2H, Th-CH), 8.17 (t, 2H, SDT-CH), 7.23 (d, $^3J_{H-H}$=5 Hz, 2h Th-CH), 7.20 (d, $^3J_{H-H}$=5 Hz, 2H Th-CH), 6.75 (m, 2H, Th-CH), 2.84 (t, $^3J_{H-H}$=7 Hz, 4H Th-CH$_2$), 1.74 (h, $^3J_{H-H}$=6 Hz, 4H, CH), 1.60 (m, 2H, CH), 1.43 (m, 4H, CH$_2$), 1.31 (m, 14H, CH$_2$), 1.24 (m, 10H, CH$_2$), 1.13 (m, 4H, SiCH$_2$), 0.92 (m, 6H, CH$_3$), 0.85 (m, 12H, CH$_3$). $^{13}$C{$^1$H} NMR (CDCl$_3$): 154.55, 150.50, 148.03, 146.99, 145.19, 142.82 (s, quaternary), 140.17 (s, CH), 139.66, 138.58, 134.62 (s, quaternary), 132.70 (s, CH), 130.87 (s, CH), 125.22 (s, CH), 124.66 (s, CH), 124.60 (s, CH), 120.47 (s, quaternary), 36.05 (s, CH), 35.79 (s, CH$_2$), 31.57 (s, SiCH$_2$), 31.54 (s, CH$_2$), 30.29 (s, ThCH$_2$), 29.02 (s, CH$_2$), 28.99 (s. CH$_2$), 28.78 (s, CH$_2$), 23.05 (s, CH$_2$), 22.58 (s, CH$_2$), 17.75 (s, CH$_2$), 14.21 (s, CH$_3$), 14.08 (s, CH$_3$), 10.87 (s, CH$_3$). Anal. Calcd. for C$_{62}$H$_{72}$N$_6$S$_8$Si: C, 62.79; H, 6.12; N, 7.09. Found: C, 62.5; H, 6.00; N, 7.05%. HRMS (EI) m/z, calcd for C$_{62}$H$_{72}$N$_6$S$_8$Si (M$^+$): 1184; found: 1184. Absorbance: (CHCl$_3$) λ$_{max}$=625 nm. λ$_{onset}$=725 mm, ε=35000 cm$^{-1}$M$^{-1}$. (As Cast Film) λ$_{max}$=655, 710 nm, λ$_{onset}$=795 nm.

Figure 3:
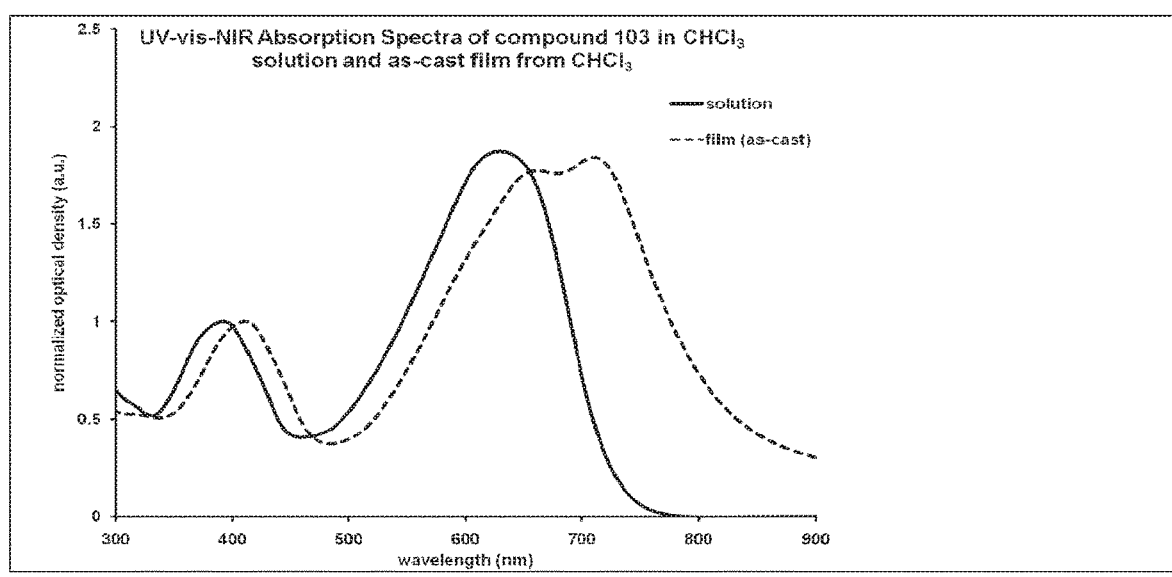
FIG. 3 shows a UV-VIS-NIR absorption spectrum of compound 103 in CHCl$_3$ solution and of a film of compound 103 as-cast from CHCl$_3$ solution.

The UV-VIS-NIR absorption spectrum of 103 in CHCl$_3$ solution and of a film of 103 as-cast from CHCl$_3$ solution is shown in FIG. 3.

Example 4

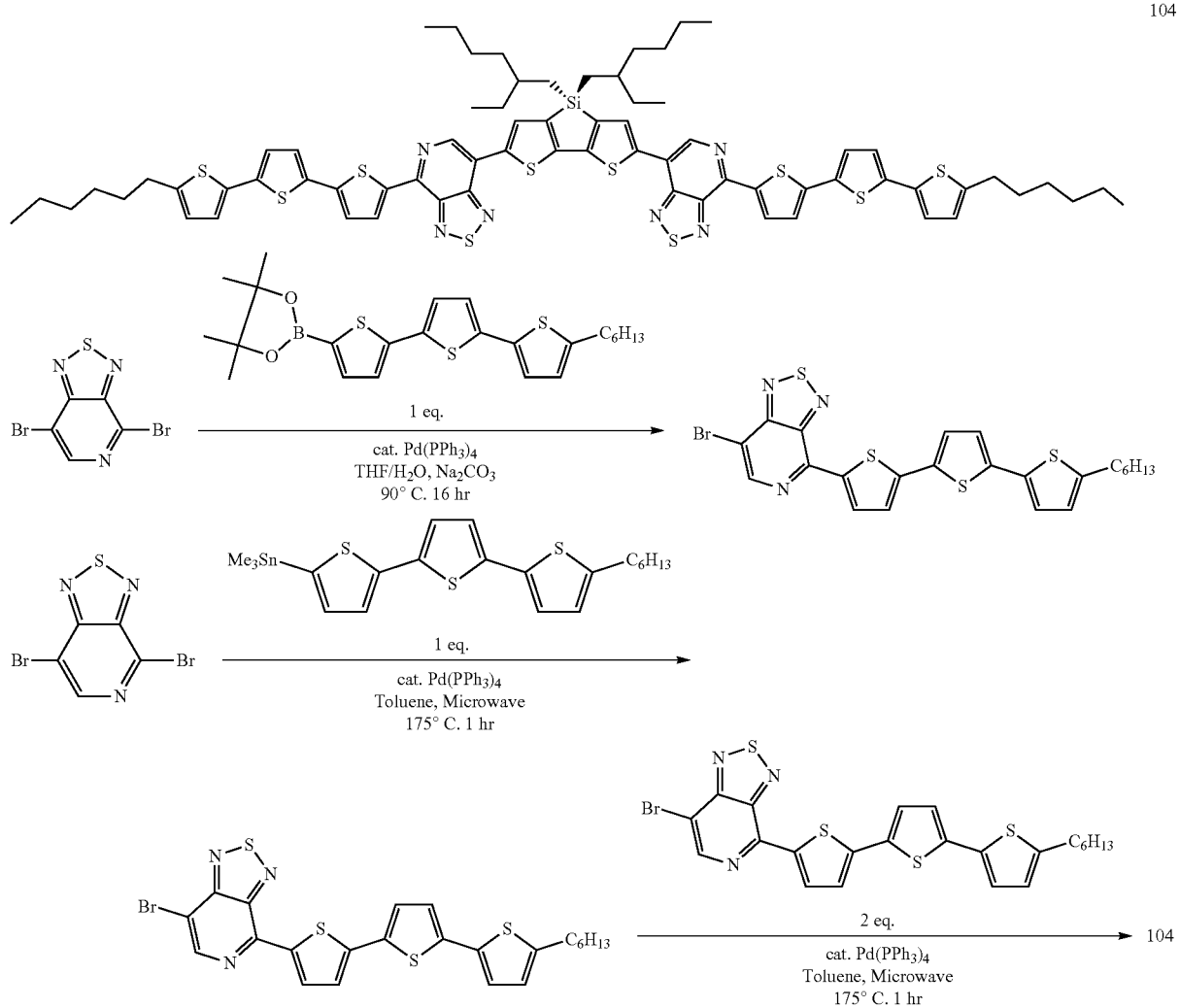

Synthesis of 7-bromo-4-(5-(5-(5-hexylthiophen-2-yl)thiophen-2-yl)thiophen-2-yl)-[1,2,5]thiadiazolo[3,4-c]pyridine (HexThThThPTBr): Suzuki: In a N$_2$ filled glove box a 20 mL glass tube was charged with 4,7-dibromo-pyridal[2,1,3]thiadiazole (PTBr$_2$, 470 mg, 1.59 mmol), Na$_2$CO$_3$ (1g), Pd(PPh$_3$)$_4$ (0.050 g, 0.01 mmol), anhydrous THF (10 mL), and sealed with a Teflon® cap. To this mixture was added de-gassed de-ionized water (5 mL) under Ar and the mixture stirred for 5 minutes. 5'Hexyl-2,2',2"-trithiophene-5-boronic acid pinacol ester (729 mg, 1.59 mmol) in anhydrous THF (5 mL) was then added to the reaction mixture which was subsequently purged with Ar for 5 minutes. The reaction mixture was heated to 90° C. and vigorously stirred for 16 hours. Upon cooling the reaction mixture was poured into 500 mL of a 1:1 MeOH/H$_2$O solution and stirred for 20 minutes. The precipitate that formed was collect by filtration and washed with 500 mL of a 2:1 MeOH/H$_2$O solution and 100 mL of MeOH. The crude product was purified by flash chromatography eluting with a hexanes/CH$_2$Cl$_2$ gradient. After fraction collection and solvent removal the resulting red solid was dried under high vacuum for 48 hours. The product was collected as red solid. Recovered yield: 400 mg (46%). Stille: In a N$_2$ filled glove box a 5 mL glass tube was charged with 4,7-dibromo-pyridal[2,1,3]thiadiazole (PTBr$_2$, 197 mg, 0.67 mmol), 5'-Hexyl-2,2',2"-trithiophene-5-trimethylstannane (330 mg, 0.067 mmol), Pd(PPh$_3$)$_4$ (0.025 g, 0.02 mmol), toluene (4 mL), and sealed with a Teflon® cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with CHCl$_3$ (5% Et$_3$N) (500 mL). All volatiles were removed in vacuo to give the crude product as a red solid. The product was slurried in MeOH (200 mL), filtered, washed with MeOH (200 mL), and dried under high vacuum for 24 hours. The product was collected as red solid. Recovered yield: 310 mg (85%). $^1$H NMR (CDCl$_3$): δ 8.64 (s, 1H, PT-CH), 8.59 (d, 1H, $^3J_{H-H}$=5 Hz, Th-CH), 7.26 (d, 1H, $^3J_{H-H}$=5 Hz, Th-CH), 7.24 (d, 1H, $^3J_{H-H}$=5 Hz, Th-CH), 7.05 (d, 1H, $^3J_{H-H}$=5 Hz, Th-CH), 7.03 (d, 1H, $^3J_{H-H}$=5 Hz, Th-CH), 6.71 (d, $^3J_{H-H}$=5 Hz, Th-CH), 2.80 (m, 2H, Th-CH$_2$), 1.67 (m, 2H, CH$_2$), 1.41 (m, 2H. CH$_2$), 1.34 (m, 4H, CH$_2$), 0.92 (m, 3H, CH$_3$).

Synthesis of 104: In a N$_2$ filled glove box a 20 mL microwave tube was charged with 5,5'-Bis(trimethylstannyl)-3,3'-Di-2-ethylhexylsilylene-2,2'-bithiophene (Me$_3$Sn-SDT$_{LH}$-SnMe$_3$, 188 mg, 0.25 mmol), 7-bromo-4-(5-(5-(5-hexylthiophen-2-yl)thiophen-2-yl)thiophen-2-yl)-[1,2,5]thiadiazolo[3,4-c]pyridine (HexThThThPTBr, 290 mg, 0.53 mmol), Pd(PPh$_3$)$_4$. (0.025 g. 0.02 mmol), toluene (15 mL), and sealed with a Teflon® cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with CHCl$_3$ (5% Et$_3$N) (500 mL). All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 250 mg (73%). $^1$H NMR (CDCl$_3$): δ 8.74 (s, 2H, PT-CH), 8.50 (d, $^3J_{H-H}$=5 Hz, 2H, Th-CH), 8.14 (t, 2H, SDT-CH), 7.23 (d, $^3J_{H-H}$=5 Hz, 2H Th-CH), 7.21 (d, $^3J_{H-H}$=5 Hz, 2H Th-CH), 7.02 (d, $^3J_{H-H}$=5 Hz, 2H Th-CH), 6.99 (d, $^3J_{H-H}$=5 Hz, 2H Th-CH), 6.68 (d, $^3J_{H-H}$=5 Hz, 2H Th-CH), 2.81 (m, $^3J_{H-H}$=7 Hz, 4H Th-CH$_2$), 1.70 (h, $^3$1$_{H-H}$=7 Hz, 4H, CH), 1.60 (m, 2H, CH), 1.40 (m, 4H, CH$_2$), 1.34 (m, 14H, CH$_2$), 1.27 (m, 10H, CH$_2$), 1.15 (m, 4H, SiCH$_2$), 0.91 (m, 8H, CH$_3$), 0.87 (m, 10H, CH$_3$). Absorbance: (CHCl$_3$) $\lambda_{max}$=645 nm, $\lambda_{onset}$=765 nm, ε=36500 cm$^{-1}$M$^{-1}$. (As Cast Film) $\lambda_{max}$=680 nm, $\lambda_{onset}$=875 nm.

Figure 4:
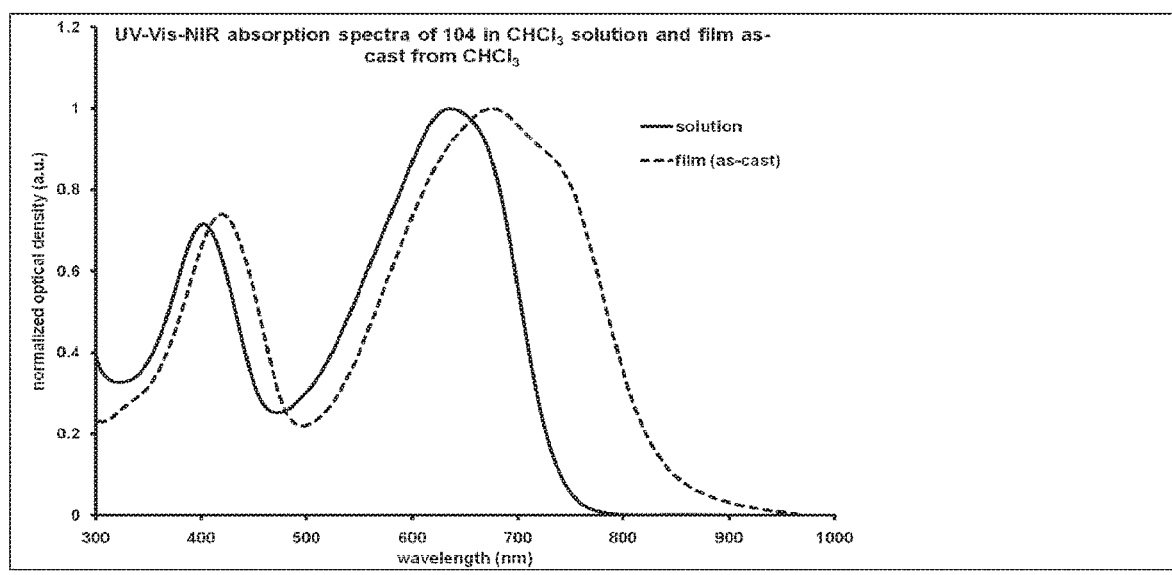
FIG. 4 shows a UV-VIS-NIR absorption spectrum of compound 104 in CHCl$_3$ solution and of a film of compound 104 as-cast from CHCl$_3$ solution.

The UV-VIS-NIR absorption spectrum of 104 in CHCl$_3$ solution and of a film of 104 as-cast from CHCl$_3$ solution is shown in FIG. 4.

Example 5

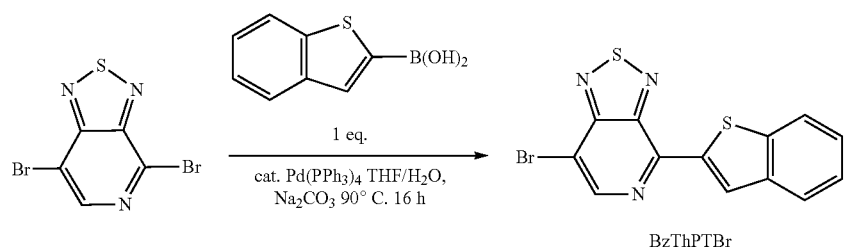

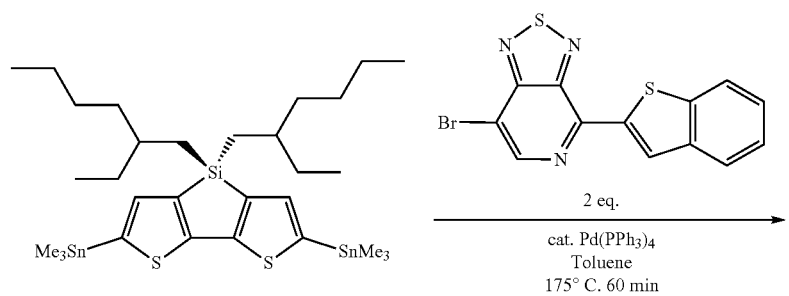

-continued

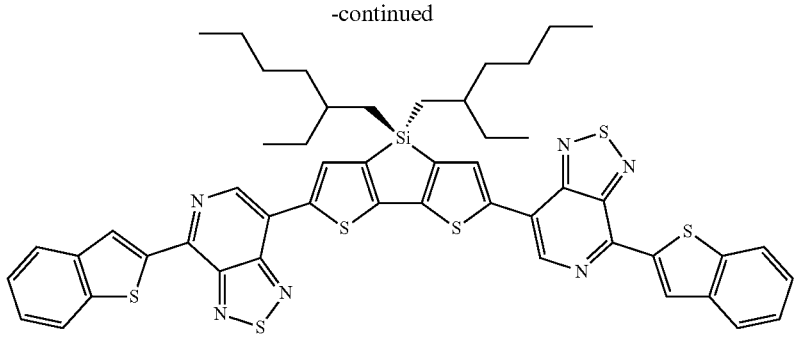

105

Synthesis of 4-(benzo[b]thiophen-2-yl)-7-bromo-[1,2,5]thiadiazolo[3,4-c]pyridine (BzThPTBr): in a $N_2$ filled glove box a 20 mL glass tube was charged with 4,7-dibromo-pyridal[2,1,3]thiadiazole ($PTBr_2$, 510 mg, 1.73 mmol), $Na_2CO_3$ (1 g), $Pd(PPh_3)_4$ (0.050 g, 0.04 mmol), anhydrous THF (6 mL), and sealed with a Teflon® cap. To this mixture was added de-gassed de-ionized water (5 mL) under Ar and the mixture stirred for 5 minutes. Benzothiophene-2-boronic acid (340 mg, 1.9 mmol) in anhydrous THF (6 mL) was then added to the reaction mixture which was subsequently purged with Ar for 5 minutes. The reaction mixture was heated to 90° C. and vigorously stirred for 16 hours. Upon cooling the reaction mixture was poured into 500 mL of a 1:1 $MeOH/H_2O$ solution and stirred for 20 minutes. The precipitate that formed was collect by filtration and washed with 500 mL of a 2:1 $MeOH/H_2O$ solution and 100 mL of MeOH (product is slightly soluble in MeOH). The solid was dried under high vacuum for 48 hours. The product was collected as an orange solid. Recovered yield: 410 mg (68%). $^1H$ NMR ($CDCl_3$): δ 8.99 (s, 1H, PT-CH), 8.74 (s, 1H, Th-CH), 7.94 (d, $^3J_{H-H}$=8 Hz, 1H Bz-CH), 7.91 (d, $^3J_{H-H}$=8 Hz, 1H Bz-CH), 7.74 (t, $^3J_{H-H}$=8 Hz, 1H, Bz-CH), 7.71 (t, $^3J_{H-H}$=8 Hz, 1H, Bz-CH). $^{13}C\{^1H\}$ NMR ($CDCl_3$): 156.6, 148.4, 147.8 (s, quaternary), 145.7 (s, CH), 141.7, 141.1, 140.9 (s, quaternary), 130.3 (s, CH), 126.7 (s, CH), 125.5 (s, CH), 125.1 (s, CH), 122.5 (s, CH), 109.7 (s, quaternary). Anal. Calcd. for $C_{13}H_6BrN_3S_2$: C, 44.84; H, 1.74; N, 12.07. Found: C, 45.0; H, 1.46; N, 11.8%.

Synthesis of 105: In a $N_2$ filled glove box a 20 mL microwave tube was charged with 5,5'-Bis(trimethylstannyl)-3,3'-Di-2-ethylhexylsilylene-2,2'-bithiophene ($Me_3Sn$-$SDT_{EH}$-$SnMe_3$, 395 mg, 0.53 mmol), 4-(benzo[b]thiophen-2-yl)-7-bromo-[1,2,5]thiadiazolo[3,4-c]pyridine (BzThPTBr, 374 mg, 1.07 mmol), $Pd(PPh_3)_4$ (0.025 g, 0.02 mmol), toluene (15 mL), and sealed with a Teflon® cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with $CHCl_3$ (5% $Et_3N$) (500 mL). All volatiles were removed in vacuo to give the crude product as a purple solid. The material was then loaded onto silica and purified by flash chromatography using a hexanes/$CHCl_3$ (5% $Et_3N$ gradient. After fraction collection and solvent removal a purple solid was obtained. The solid was slurried in MeOH (300 mL), sonicated for 10 minutes, and filtered. The solid was washed with copious amounts of MeOH and then dried under vacuum for 24 hours. The product was collected as purple solid. Recovered yield: 350 mg (77%). $^1H$ NMR ($CDCl_3$): δ 8.77 (s, 2H, PT-CH), 8.64 (m, 2H Th—CH), 8.27 (t, 2H, SDT-CH), 7.88 (d, $^3J_{H-H}$=8 Hz, 2H Bz-CH), 7.85 (d, $^3J_{H-H}$=8 Hz, 2H Bz-CH), 7.34 (m, $^3J_{H-H}$=8 Hz, 4H, Bz-CH), 1.65 (h, $^3J_{H-H}$=6 Hz, 2H, CH), 1.43 (m, 4H, $CH_2$), 1.38 (m, 4H, $CH_2$), 1.31 (m, 8H, $CH_2$), 1.19 (m, 4H, $SiCH_2$), 0.92 (t, $^3J_{H-H}$=8 Hz, 6H, $CH_3$), 0.89 (t, $^3J_{H-H}$=8 Hz, 6H, $CH_3$). $^{13}C\{^1H\}$ NMR ($CDCl_3$): 154.17, 150.75, 148.09, 145.50, 145.49, 145.08, 141.74 (s, quaternary), 141.20 (s, CH), 139.65 (s, quaternary), 138.60 (s, CH), 131.71 (m. SDT-CH, 128.82 (s, CH), 126.03 (s, quaternary), 125.04 (s, CH), 124.59 (s, quaternary), 122.39 (s, CH), 121.27 (s, CH), 36.13 (s, $SiCH_2$), 35.89 (s, CH), 29.10 (s, $2 \times CH_2$), 23.11 (s, $CH_2$), 17.81 (s, $CH_2$), 14.27 (s, $CH_3$), 10.93 (s, $CH_3$). Anal. Calcd. for $C_{50}H_{48}N_6S_6Si$: C, 62.99; H, 5.07; N, 8.81. Found: C, 62.8; H, 4.59; N, 8.82%. HRMS (EI) m/z, calcd for $C_{50}H_{48}N_6S_6Si$ ($M^+$): 952; found: 952. Absorbance: ($CHCl_3$) $\lambda_{max}$=594 nm, $\lambda_{onset}$=696 nm. (As Cast Film) $\lambda_{max}$=620, 664 nm, $\lambda_{onset}$=758 nm.

Figure 5:
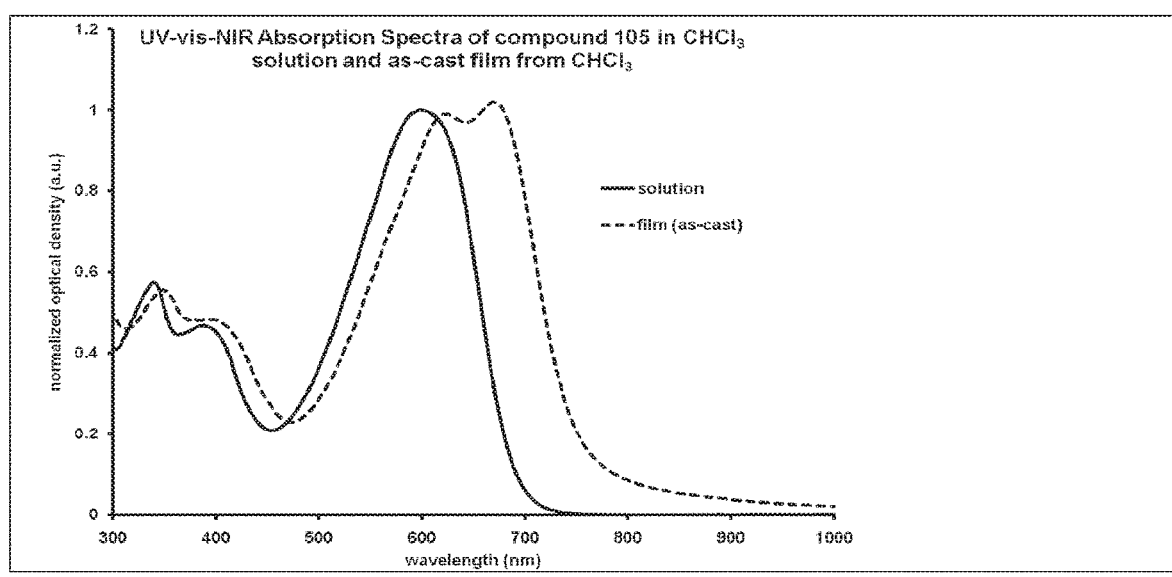
FIG. 5 shows a UV-VIS-NIR absorption spectrum of compound 105 in CHCl$_3$ solution and of a film of compound 105 as-cast from CHCl$_3$ solution.

The UV-VIS-NIR absorption spectrum of 105 in $CHCl_3$ solution and of a film of 105 as-cast from $CHCl_3$ solution is shown in FIG. 5.

Example 6

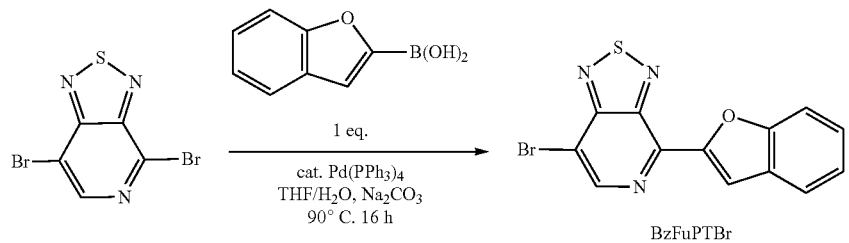

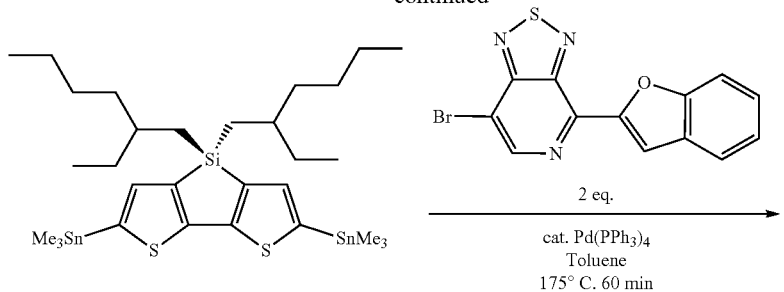

-continued

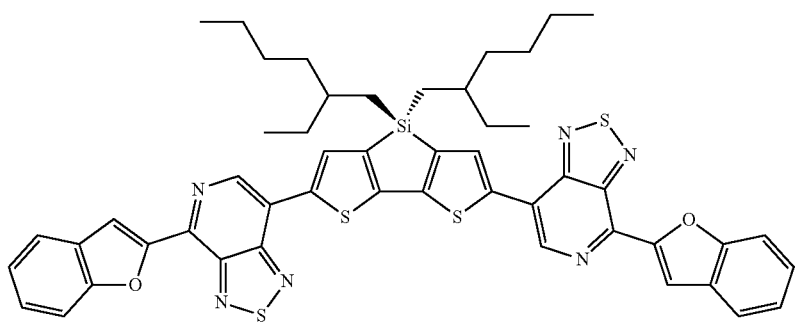

106

Synthesis of 4-(benzofuran-2-yl)-7-bromo-[1,2,5]thiadiazolo[3,4-c]pyridine (BzFuPTBr): In a $N_2$ filled glove box a 20 mL glass tube was charged with 4,7-dibromo-pyridal[2,1,3]thiadiazole (PTBr$_2$, 300 mg, 1.01 mmol), Na$_2$CO$_3$ (1 g), Pd(PPh$_3$)$_4$ (0.050 g, 0.04 mmol), anhydrous THF (6 mL), and sealed with a Teflon® cap. To this mixture was added de-gassed de-ionized water (5 mL) under Ar and the mixture stirred for 5 minutes. Benzofuran-2-boronic acid (164 mg, 1.01 mmol) in anhydrous THF (6 mL) was then added to the reaction mixture which was subsequently purged with Ar for 5 minutes. The reaction mixture was heated to 90° C. and vigorously stirred for 16 hours. Upon cooling the reaction mixture was poured into 500 mL of a 1:1 MeOH/H$_2$O solution and stirred for 20 minutes. The precipitate that formed was collect by filtration and washed with 500 mL of a 2:1 MeOH/H$_2$O solution and 100 mL of MeOH. The crude product was purified by flash chromatography eluting with a hexanes/CHCl$_3$ gradient. After fraction collection and solvent removal the resulting orange solid was dried under high vacuum for 48 hours. The product was collected as orange solid. Recovered yield: 205 mg (61%). $^1$H NMR (CDCl$_3$): δ 8.88 (s, 1H, PT-CH), 8.44 (s, 1H, Th-CH), 7.78 (d, $^3J_{H-H}$=8 Hz, 1H Bz-CH), 7.72 (d, $^3J_{H-H}$=8 Hz, 1H Bz-CH), 7.47 (dd, $^3J_{H-H}$=8 Hz, 1H, Bz-CH), 7.34 (dd, $^3J_{H-H}$=8 Hz, 1H, Bz-CH). $^{13}$C{$^1$H} NMR (CDCl$_3$): 152.2, 148.1, 146.2. (s, quaternary), 144.4 (s, CH), 141.2, 140.1, 138.3 (s, quaternary), 130.5 (s, CH), 125.5 (s, CH), 124.1 (s, CH), 123.8 (s, CH), 122.4 (s, CH), 110.2 (s, quaternary).

Synthesis of 106: In a $N_2$ filled glove box a 20 mL microwave tube was charged with 5,5'-Bis(trimethylstannyl)-3,3'-Di-2-ethylhexylsilylene-2,2'-bithiophene (Me$_3$Sn-SDT$_{EH}$-SnMe$_3$, 93 mg, 0.12 mmol), 4-(benzofuran-2-yl)-7-bromo-[1,2,5]thiadiazolo[3,4-c]pyridine (BzFuPTBr, 83 mg, 0.25 mmol), Pd(PPh$_3$)$_4$ (0.025 g, 0.02 mmol), toluene (15 mL), and sealed with a Teflon® cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with CHCl$_3$ (5% Et$_3$N) (500 mL). All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 59 mg (51%). $^1$H NMR (CDCl$_3$); δ 8.97 (s, 2H, PT-CH), 8.35 (m, 2H Fu-CH), 8.25 (m, 2H, SDT-CH), 7.75 (d, $^3J_{H-H}$=8 Hz, 2H Bz-CH), 7.72 (d, $^3J_{H-H}$=8 Hz, 2H Bz-CH), 7.44 (dd. $^3J_{H-H}$=8 Hz, 2H, Bz-CH), 7.32 (dd, $^3J_{H-H}$=8 Hz, 2H, Bz-CH), 1.59 (h, $^3J_{H-H}$=7 Hz, 2H, CH), 1.40 (m, 4H, CH$_2$), 1.32 (m, 4H, CH$_2$), 1.26 (m, 8H, CH$_2$), 1.15 (m, 4H, SiCH$_2$), 0.86 (M, 12H, CH$_3$). $^{13}$C{$^1$H} NMR (CDCl$_3$): 155.63, 154.36, 151.23, 148.13, 145.63, 141.19 (s, quaternary), 140.16 (s, PT-CH), 138.36 (s, quaternary), 138.60 (s, CH), 131.71 (s, SDT-CH), 128.89 (s, quaternary), 126.18, 123.56, 122.32 (s, Bz-CH), 121.77 (s, quaternary), 113.53 (s, Fu-CH), 112.06 (s, Bz-CH), 36.07 (s, CH$_2$), 35.80 (s, CH), 29.02 (s, CH$_2$), 28.97 (s, CH$_2$), 23.06 (s, CH$_2$), 17.76 (s, CH$_2$), 14.21 (s, CH$_3$), 10.87 (s, CH$_3$). Anal. Calcd. for C$_{50}$H$_{48}$N$_6$O$_2$S$_4$Si: C, 65.18; H, 5.25; N, 912. Found: C, 65.2; H, 5.22; N, 9.14%. HRMS (EI) m/z, calcd for C$_{50}$H$_{48}$N$_6$O$_2$S$_4$Si (M$^+$): 920; found: 920. Absorbance: (CHCl$_3$) $\lambda_{max}$=610 nm, $\lambda_{onset}$=695 nm. (As Cast Film) $\lambda_{max}$=625, 675 nm, $\lambda_{onset}$=760 nm.

Figure 6:
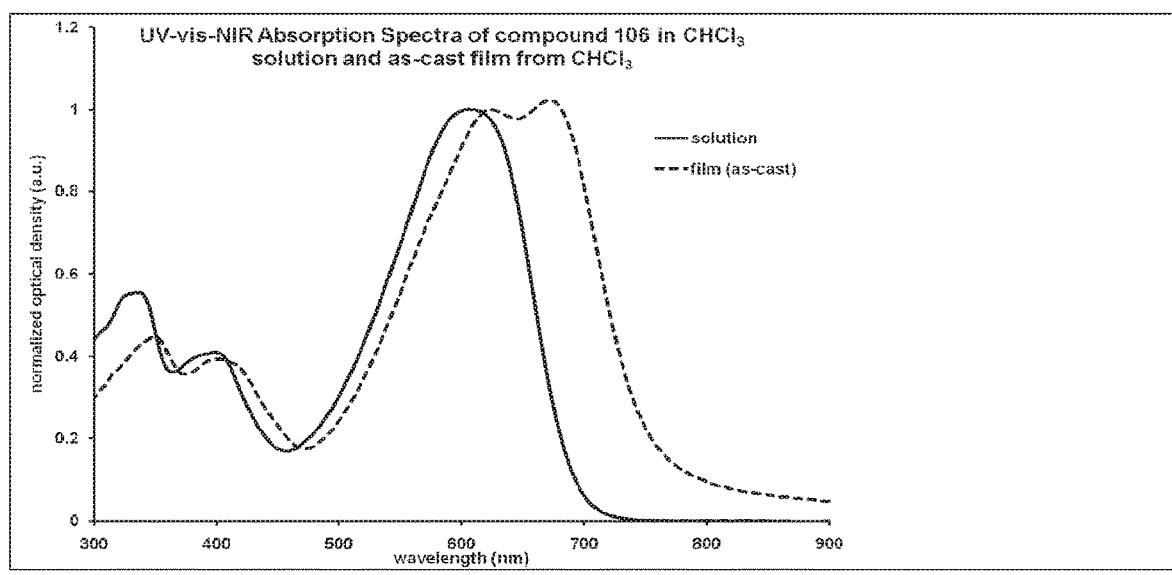
FIG. 6 shows a UV-VIS-NIR absorption spectrum of compound 106 in CHCl$_3$ solution and of a film of compound 106 as-cast from CHCl$_3$ solution.

The UV-VIS-NIR absorption spectrum of 106 in CHCl$_3$ solution and of a film of 106 as-cast from CHCl$_3$ solution is Shown in FIG. 6.

Example 7

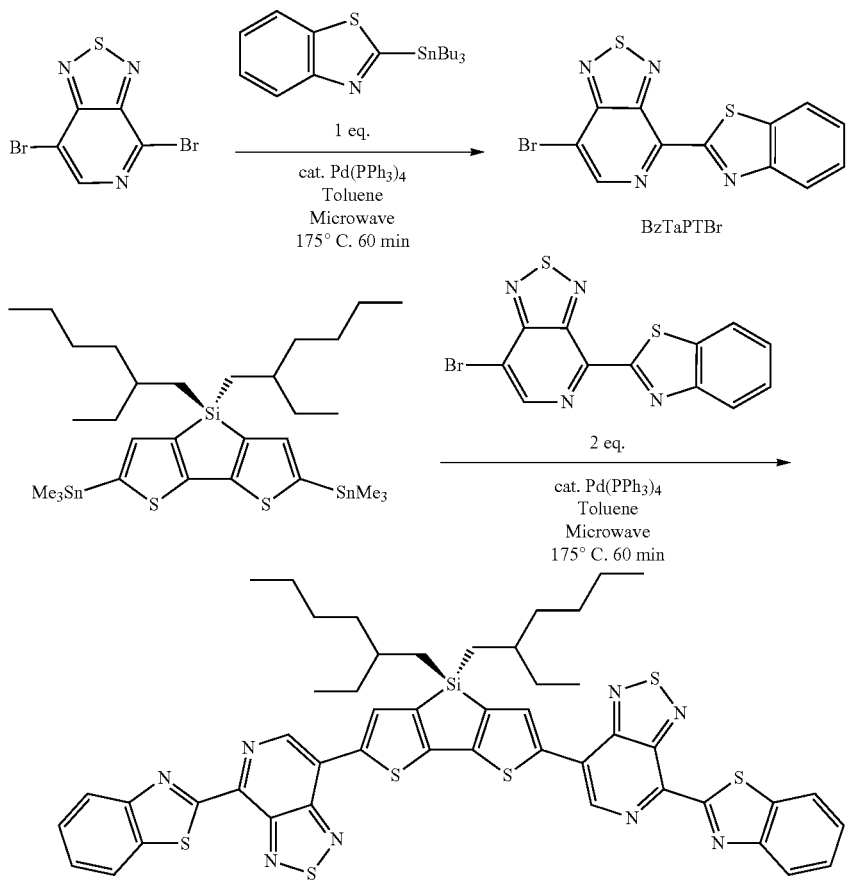

107

Synthesis of 4-(benzo[d]thiazol-2-yl)-7-bromo-[1,2,5]thiadiazolo[3,4-c]pyridine (BzTaPTBr): In a $N_2$ filled glove box a 20 mL glass tube was charged with 4,7-dibromo-pyridal[2,1,3]thiadiazole ($PTBr_2$, 710 mg, 2.40 mmol), 2-tributylstannylbenzothiazole (1.0 g, 2.36 mmol), $Pd(PPh_3)_4$ (0.050 g, 0.04 mmol), anhydrous Toluene (15 mL), and sealed with a Teflon cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with $CHCl_3$ (5% $Et_3N$) (500 mL). All volatiles were removed in vacuo to give the crude product as an orange solid. The material was then loaded onto silica and purified by flash chromatography using a hexanes/$CHCl_3$ (5% $Et_3N$) gradient. After fraction collection and solvent removal an orange solid was obtained. The solid was slurried in MeOH (300 mL), sonicated for 10 minutes, and filtered. The solid was washed with copious amounts of MeOH and then dried under vacuum for 24 hours. The product was collected as orange solid. Recovered yield: 442 mg (53%). $^1$H NMR ($CDCl_3$): δ 8.90 (s. 1H, PT-CH), 8.40 (d, $^3J_{H-H}$=9 Hz, 1H Bz-CH), 8.03 (d, $^3J_{H-H}$=9 Hz, 1H Bz-CH), 7.59 (m, $^3J_{H-H}$=9 Hz, 1H, Bz-CH), 7.53 (m, $^3J_{H-H}$=9 Hz, 1H, Bz-CH). $^{13}$C{$^1$H} NMR ($CDCl_3$): 158.2, 148.7, (s, quaternary), 146.5 (s, CH), 145.2, 141.7, 141.1, 140.9 (s, quaternary), 126.2 (s, CH), 125.3 (s, CH), 124.6 (s, CH), 122.8 (s, CH), 111.4 (s, quaternary).

Figure 7:
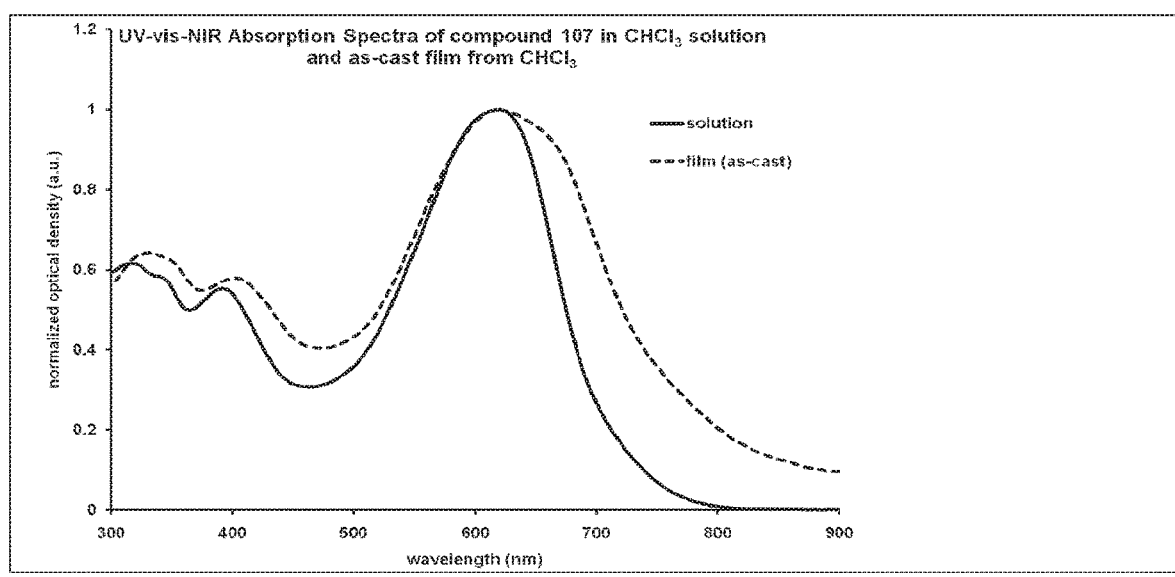
FIG. 7 shows a UV-VIS-NIR absorption spectrum of compound 107 in CHCl$_3$ solution and of a film of compound 107 as-cast from CHCl$_3$ solution.

Synthesis of 107: In a $N_2$ filled glove box a 20 mL microwave tube was charged with 5,5'-Bis(trimethylstannyl)-3,3'-Di 2 ethylhexylsilylene-2,2'-bithiophene ($Me_3Sn$-$SDT_{EH}$-$SnMe_3$, 280 mg, 0.38 mmol), benzo[d]thiazol-2-yl)-7-bromo-[1,2,5]thiadiazolo[3,4-c]pyridine (BzTaPTBr, 263 mg, 0.75 mmol), $Pd(PPh_3)_4$ (0.025 g, 0.02 mmol), toluene (15 mL), and sealed with a Teflon cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with $CHCl_3$ (5% $Et_3N$) (500 mL). All volatiles were removed in vacuo to give the crude product as a purple solid. The material was then loaded onto silica and purified by flash chromatography using a hexanes/$CHCl_3$ (5% $Et_3N$) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 220 mg (61%). $^1$H NMR ($CDCl_3$): δ 9.07 (s, 2H, PT-CH), 8.41 (t, 2H, SDT-CH), 8.31 (d, $^3J_{H-H}$=9 Hz, 2H Bz-CH), 8.04 (d, $^3J_{H-H}$=9 Hz, 2H Bz-CH), 7.56 (m, $_3J_{H-H}$8 Hz, 2H, Bz-CH), 7.51 (m, $^3J_{H-H}$=8 Hz, 2H, Bz-CH), 1.57 (m, 2H, CH), 1.4-1.1 (bm, 16H, $CH_2$), 0.9-0.8 (m, 12H, CH$_3$). Anal. Calcd. for C$_{18}$H$_{46}$N$_8$S$_6$Si: C, 60.34; H, 4.85; N, 11.73. Found: C, 58.1; H, 4.51; N, 12.2%, HRMS (EI) m/z, calcd for C$_{50}$H$_{48}$N$_6$S$_6$Si (M$^+$): 954; found: 954. Absorbance: (CHCl$_3$) $\lambda_{max}$=620 nm, $\lambda_{onset}$=725 nm. (As Cast Film) $\lambda_{max}$=620, 660 nm, $\lambda_{onset}$=775 nm.
The UV-VIS-NIR absorption spectrum of 107 in CHCl$_3$ solution and of a film of 107 as-cast from CHCl$_3$ solution is shown in FIG. 7.
Example 8
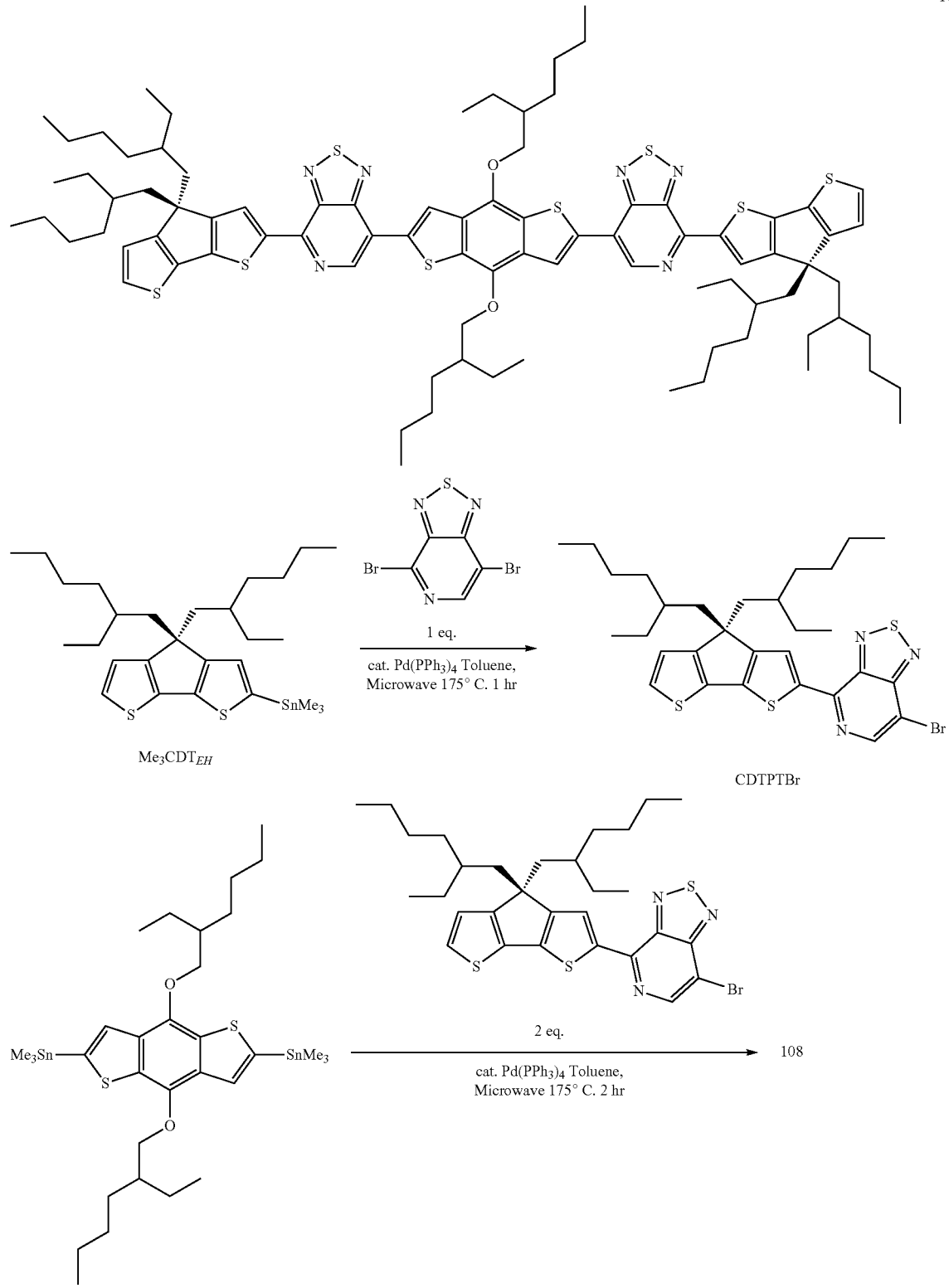

Synthesis of 5-(trimethylstannyl)-4,4-bis(2-ethylhexyl)-4H-cyclopenta[2,1-b;3,4-b']dithiophene (Me$_3$Sn-CDT$_{EH}$): A dry three-neck round bottom flask was equipped with a Schlenk adapter, dropping funnel, and rubber septum. Under argon, compound CDT$_{EH}$ (2 g, 4.96 mmol) was dissolved in dry THF (200 mL) and cooled −78° C. using a dry ice/acetone cold bath. A solution of t-butyllithium (1.7 M pentane, 3.21 mL, 5.46 mmol) diluted with dry pentane (30 mL) was then added dropwise over 20 minutes via a dropping funnel. The dropping funnel was rinsed with dry pentane (30 mL) to ensure all lithium reagent was transferred to the reaction vessel. The reaction was stirred at −78° C. under argon for 2 hours. A solution of trimethyltin chloride (1.5 g, 7.5 mmol) in dry pentane (30 mL) was then added dropwise over 5 minutes via a dropping funnel. The dropping funnel was rinsed with dry pentane (30 mL) to ensure all tin reagent was transferred to the reaction vessel. The reaction was stirred at −78° C. under argon for 1 hour and subsequently warmed to room temperature and stirred for a further 1 hour. The mixture was then poured into de-ionized water (300 mL) and the organic phase extracted with hexanes (3×100 mL). The organic phases were collected and washed with de-ionized water (5×100 mL), dried over magnesium sulphate, filtered, and concentrated to give the product as yellow oil. Yield 2.65 g (95%). $^1$H NMR (500 MHz, CD$_2$Cl$_2$): δ 7.11 (m, 1H), 7.00 (m, 1H), 6.95 (m, 1H), 1.89 (m, 4H, C-CH$_2$), 1.1-0.8 (m, 18H, alkyl), 0.75 (m, 6H, alkyl), 0.60 (m, 8H, alkyl), 0.36 (s, d, 9H, $^2J_{H-Sn}$=57 Hz, Sn—CH$_3$).

Synthesis of 4-4,4-bis(2-ethylhexyl)-4H-cyclopenta[2,1-b;3,4-']dithiophene-7-bromo-[1,2,5]thiadiazolo[3,4-c]pyridine (CDTPTBr): In a N$_2$ filled glove box a 20 mL glass tube was charged with 4,7-dibromo-pyridal[2,1,3]thiadiazole (PTBr$_2$, 520 mg, 1.76 mmol), 5-(trimethylstannyl)-4,4-bis(2-ethylhexyl)-4H-cyclopenta[2,1-b;3,4-b']dithiophene (Me$_3$Sn-CDT$_{EH}$, 985 mg, 1.74 mmol), Pd(PPh$_3$)$_4$ (0.025 g, 0.02 mmol), anhydrous xylenes (15 mL), and sealed with a Teflon® cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with CHCl$_3$ (5% Et$_3$N) (500 mL). All volatiles were removed in vacuo to give the crude product as a red-purple oil. The material was then loaded onto silica and purified by flash chromatography using a hexanes/CH$_2$Cl$_2$ gradient. The second fraction was collected and all solvent was removed in vacuo to give the product as a deep-red oil. Recovered yield: 910 mg (85%). $^1$H NMR (CD$_2$Cl$_2$): δ 8.62 (m, 1H, Th-CH), 8.56 (s, 1H, PT-CH), 7.34 (d, $^3J_{H-H}$=8 Hz, 1H Th—CH), 7.03 (m, $^3J_{H-H}$=6 Hz, 1H Th-CH), 2.04 (m, 2H, C-CH$_2$), 1.95 (m, 2H, C-CH$_2$), 1.00 (m, 8H, alkyl), 0.96 (m, 8H, alkyl), 0.73 (m, 4H, alkyl), 0.69 (m, 2H, alkyl), 0.61 (m, 8H, alkyl).

Synthesis of 108: In a N$_2$ filled glove box a 5 mL microwave tube was charged with Me$_3$Sn-BDT$_{EH}$-SnMe$_3$ (270 mg, 0.35 mmol), CDTPTBr (430 mg, 0.70 mmol), Pd(PRh$_3$)$_4$ (0.025 g, 0.02 mmol), xylenes (4 mL), and sealed with a Teflon® cap. The reaction mixture was heated to 120° C. for 3 minutes, 140° C. for 3 minutes, and 175° C. for 180 minutes, using a Biotage microwave reactor. Upon cooling, the residue was passed through a short silica plug eluting with CHCl$_3$. All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. The solid was slurried in MeOH (300 mL), sonicated for 10 minutes, and filtered. The solid was washed with copious amounts of MeOH and then dried under vacuum for 24 hours. The product was collected as purple solid. Recovered yield: 430 mg (81%). $^1$H NMR (CDCl$_3$): δ 8.92 (s, 2H, PT-CH), 8.76 (m, 2H, Th-CH), 8.66 (m, 2H, Th-CH), 7.32 (d, $^3J_{H-H}$=5 Hz, 2H Th-CH), 7.02 (m, $^3J_{H-H}$=5 Hz, 2H Th-CH), 4.36 (m, 4H, OCH), 2.09 (m, 4h, CH$_2$), 1.98 (m, 6H, CH$_2$), 1.85 (m, 2H, CH$_2$), 1.79 (m, 2H, CH$_2$), 1.72 (m, 2H, CH$_2$), 1.62 (m, 2H, CH$_2$), 1.51 (m, 8H, CH$_2$), 1.14 (m, 6H, CH$_3$), 1.00 (m, 36H, CH$_2$, CH $_3$), 0.75 (m, 12H, CH$_3$), 0.62 (m, 18H, CH$_3$). $^{13}$C{$^1$H} NMR (CDCl$_3$): 160.41, 159.75, 155.15, 148.10, 147.79, 144.80, 143.99 (s, quaternary), 142.73 (s, PT-CH), 141.39, 136.95, 136.75, 133.30, 129.47 (s, quaternary), 127.88, 127.39, 122.53, 121.97 (s CH), 119.22 (s, quaternary), 76.27 (s, OCH$_2$), 53.88, 43.35, 43.12, 40.81, 35.28, 35.25, 32.23, 30.68, 29.37, 28.66, 28.52, 27.49, 27.40, 24.02, 23.27, 22.78, 14.31, 14.07, 14.02, 11.52, 10.78, 10.63. Anal. Calcd. for C$_{86}$H$_{112}$N$_6$O$_2$S$_8$: C, 68.03; H, 7.43; N, 5.53. Found: C, 67.9; H, 7.22; N, 5.63%. Absorbance: (CHCl$_3$) $\lambda_{max}$=635 nm, $\lambda_{onset}$=715 nm. (As Cast Film) $\lambda_{max}$=640, 670 nm, $\lambda_{onset}$=790 nm.

Figure 8:
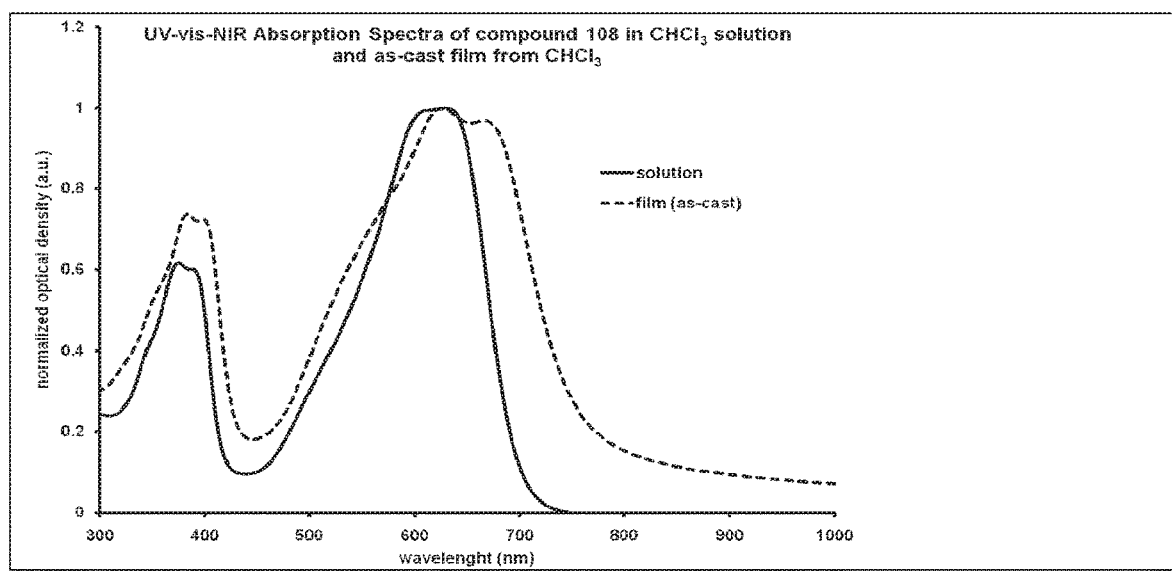
FIG. 8 shows a UV-VIS-NIR absorption spectrum of compound 108 in CHCl$_3$ solution and of a film of compound 108 as-cast from CHCl$_3$ solution.

The UV-VIS-NIR absorption spectrum of 108 in CHCl$_3$ solution and of a film of 108 as-cast from CHCl$_3$ solution is shown in FIG. 8.

Example 9

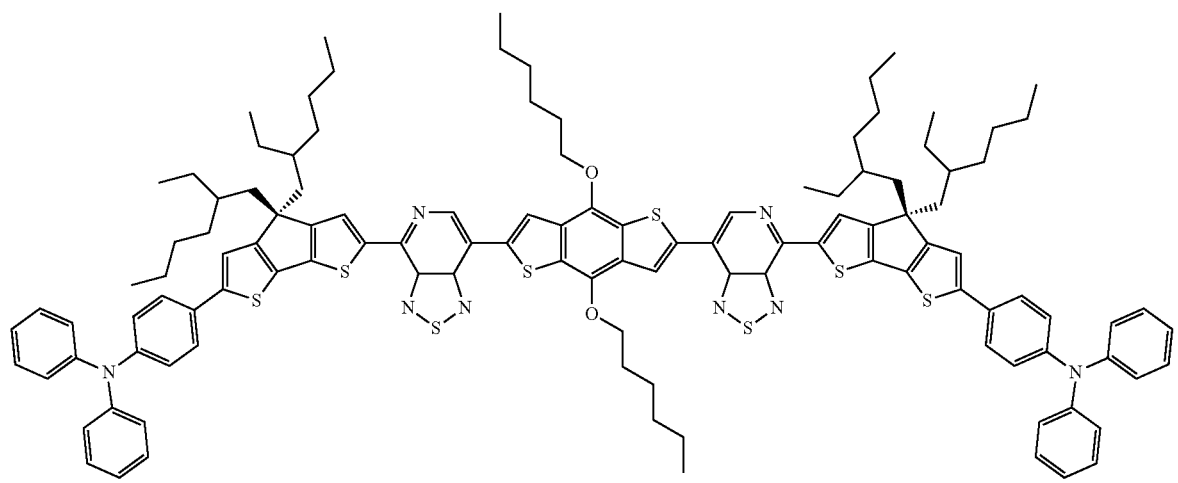

109

-continued
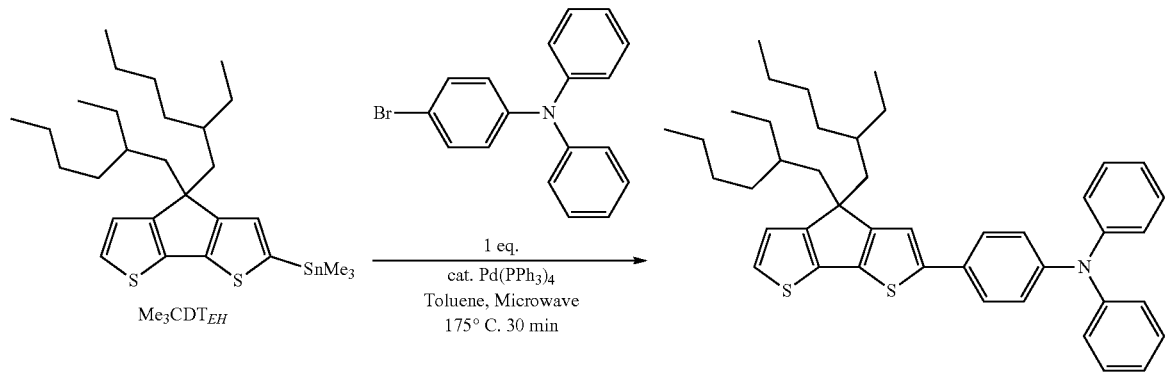
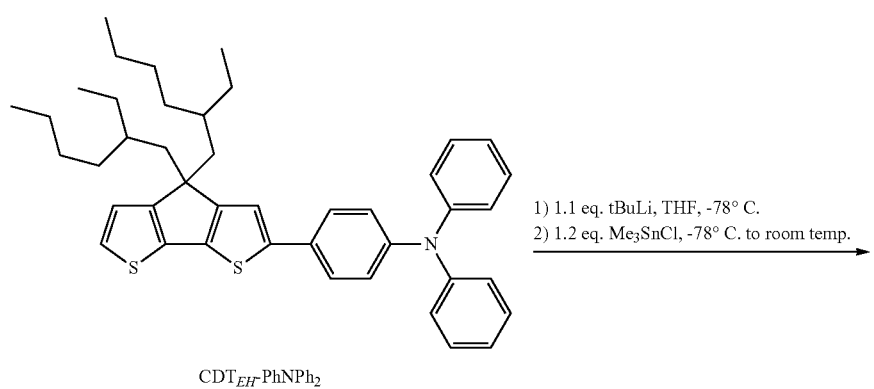
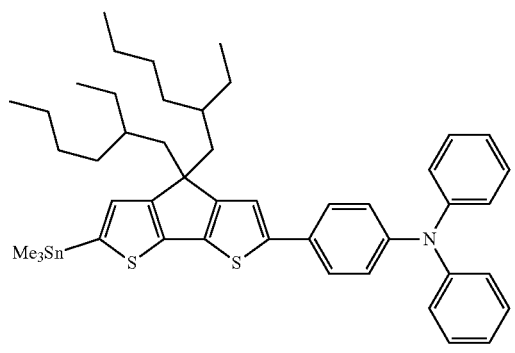
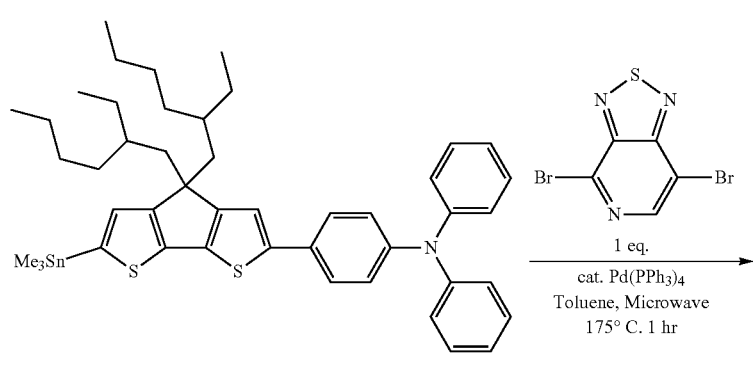

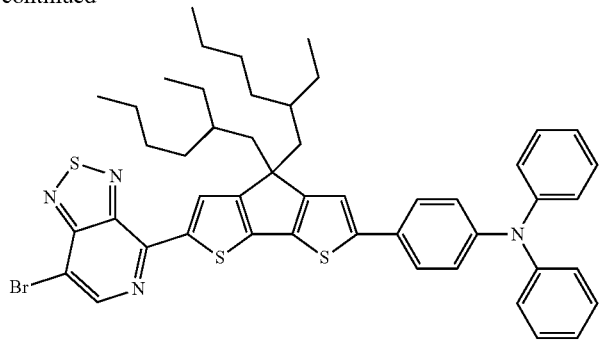

BrPT-CDT$_{EH}$-PhNPh$_2$

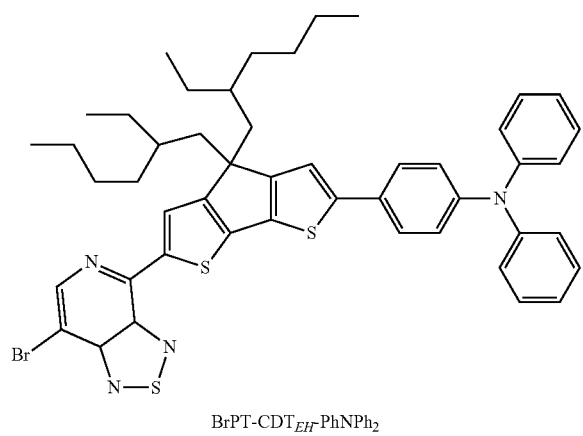

BrPT-CDT$_{EH}$-PhNPh$_2$

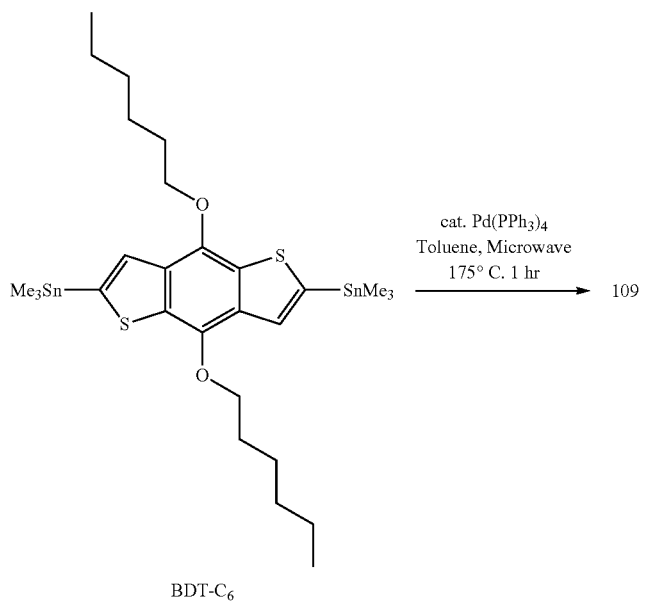

BDT-C$_6$

Synthesis of 5-(trimethylstannyl)-4,4-bis(2-ethylhexyl)-4H-cyclopenta[2,1-b;3,4-b']dithiophene (Me$_3$Sn-CDT$_{EH}$): A dry three-neck round bottom flask was equipped with a Schlenk adapter, dropping funnel, and rubber septum. Under argon, compound CDT$_{EH}$ (2 g, 4.96 mmol) was dissolved in dry THF (200 mL) and cooled −78° C. using a dry ice/acetone cold bath. A solution of t-butyllithium (1.7 M pentane, 3.21 mL, 5.46 mmol) diluted with dry pentane (30 mL) was then added dropwise over 20 minutes via a dropping funnel. The dropping funnel was rinsed with dry pentane (30 mL) to ensure all lithium reagent was transferred to the reaction vessel. The reaction was stirred at −78° C. under argon for 2 hours. A solution of trimethyltin chloride (1.5 g, 7.5 mmol) in dry pentane (30 mL) was then added dropwise over 5 minutes via a dropping funnel. The dropping funnel was rinsed with dry pentane (30 mL) to ensure all tin reagent was transferred to the reaction vessel. The reaction was stirred at −78° C. under argon for 1 hour and subsequently warmed to room temperature and stirred for a further 1 hour. The mixture was then poured into de-ionized water (300 mL) and the organic phase extracted with hexanes (3×100 mL). The organic phases were collected and washed with de-ionized water (5×100 mL), dried over magnesium sulphate, filtered, and concentrated to give the product as yellow oil. Yield 2.65 g (95%). $^1$H NMR (500 MHz, $CD_2Cl_2$): δ 7.11 (m, 1H), 7.00 (m, 1H), 6.95 (m, 1H), 1.89 (m, 4H, C-$CH_2$), 1.1-0.8 (m 18H, alkyl), 0.75 (m, 6H, alkyl), 0.60 (m, 8H, alkyl), 0.36 (s, d, 9H, $^2J_{H-Sn}$=57 Hz, Sn—$CH_3$).

Synthesis of $CDT_{EH}PhNPh_2$: In a $N_2$ filled glove box a 20 mL glass tube was charged with 4-bromotriphenylamine (404 mg, 1.25 mmol), ($Me_3$Sn-$CDT_{EH}$, 700 mg, 1.24 mmol), Pd(PPh$_3$)$_4$ (0.025 g, 0.02 mmol), anhydrous xylenes (15 mL), and sealed with a Teflon cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with CHCl$_3$ (500 mL). An volatiles were removed in vacuo to give the crude product as an orange oil. The material was then loaded onto silica and purified by flash chromatography using a hexanes/$CH_2Cl_2$ gradient. The second fraction was collected and all solvent was removed in vacuo to give the product as an orange oil. The product was dried under high vacuum for 24 hours. Recovered yield: 658 mg (82%). $^1$H NMR ($CD_2Cl_2$): δ 7.47 (m, 2H), 7.27 (m, 4H), 7.15 (m, 1H, CDT), 7.14 (m, 1H, CDT), 7.11 (m, 4H), 7.05 (m, 4H), 6.97 (m, 1H, CDT), 1.91 (m, 4H), 1.01 (m, 10H), 0.95 (m, 4H), 0.93 (m, 2H), 0.76 (m, 3H), 0.73 (m, 3H), 0.68 (m, 2H), 0.63 (m, 3H), 0.61 (m, 3H), Anal. Calcd. for $C_{43}H_{51}N_1S_2$: C, 79.95; H, 7.96; N, 2.17. Found: C, 79.9; H, 7.99; N, 2.50%.

Synthesis of $Me_3$Sn-$CDT_{EH}PhNPh_2$: A dry three-neck round bottom flask was equipped with a Schlenk adapter, dropping funnel, and rubber septum. Under argon, compound $CDT_{EH}PhNPh_2$ (630 mg, 0.98 mmol) was dissolved in dry THF (100 mL) and cooled −78° C. using a dry ice/acetone cold bath. A solution of t-butyllithium (1.7 M pentane, 0.69 mL, 1.17 mmol) diluted with dry pentane (30 mL) was then added dropwise over 20 minutes via a dropping funnel. The dropping funnel was rinsed with dry pentane (30 mL) to ensure all lithium reagent was transferred to the reaction vessel. The reaction was stirred at −78° C. under argon for 2 hours. A solution of trimethyltin chloride (293 mg, 1.47 mmol) in dry pentane (30 mL) was then added dropwise over 5 minutes via a dropping funnel. The dropping funnel was rinsed with dry pentane (30 mL) to ensure all tin reagent was transferred to the reaction vessel. The reaction was stirred at −78° C. under argon for 1 hour and subsequently warmed to room temperature and stirred for a further 2 hours. The mixture was then poured into de-ionized water (300 mL) and the organic phase extracted with diethyl ether (3×200 mL). The organic phases were collected and washed with de-ionized water (5×200 mL), dried over magnesium sulphate, filtered, and concentrated to give the product as red oil. The product was dried under high vacuum for 24 hours. Yield 780 mg (95%). $^1$H NMR ($CD_2Cl_2$): δ 7.46 (m, 2H), 7.27 (m, 4H), 7.13 (m, 1H, CDT), 7.11 (m, 4H), 7.04 (m, 4H), 7.01 (m, 1H, CDT), 1.88 (m, 4H), 0.99 (m, 14H), 0.88 (m, 4H), 0.74 (m, 6H), 0.64 (m, 3H), 0.60 (m, 3H), 0.37 (m, 9H).

Synthesis of BrPT-$CDT_{EH}PhNPh_2$: In a filled glove box a 5 mL glass tube was charged with 4,7-dibromo-pyridal[2,1,3]thiadiazole (PTBr$_2$, 140 mg, 0.47 mmol), $Me_3$Sn-$CDT_{EH}PhNPh_2$ (385 mg, 0.48 mmol), Pd(PPh$_3$)$_4$ (0.025 g, 0.02 mmol), anhydrous xylenes (4 mL), and sealed with a Teflon cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with CHCl$_3$ (5% Et$_3$N) (500 mL). An volatiles were removed in vacuo to give the crude product as a dark solid. The material was then loaded onto silica and purified by flash chromatography using a hexanes/CHCl$_3$ (5% Et$_3$N) gradient. The product eluted as a large blue fraction at 60:40 hexanes/CHCl$_3$ (5% Et$_3$N). The fractions were collected and all solvent was removed in vacuo to give the product as a purple film. The product was then dissolved in a minimal amount of CHCl$_3$ and stirred for 5 minutes. All solvent was then removed and the product dried under high vacuum for 24 hours. The product was obtained as a purple solid. Recovered yield: 290 mg (71%). $^1$H NMR (CDCl$_3$): δ 8.59 (s, 1H, PT), 8.57 (m. J=6 Hz, 1H CDT), 7.49 (m, $^3J_{H-H}$=5 Hz, 2H), 7.29 (m, $^3J_{H-H}$=8 Hz, 4H), 7.15 (m, 5H), 7.08 (m, $^3J_{H-H}$=8 Hz, 4H), 2.05 (m, 2H), 1.95 (m, 2H), 0.99 (m, 16H), 0.81 (m, 2H), 0.73 (m, 3H), 0.64 (m, 9H).

Synthesis of 109: In a $N_2$ filled glove box a 5 mL microwave tube was charged with $Me_3$Sn-$BDT_{C6}$-$SnMe_3$ (100 mg, 0.14 mmol), BrPT-$CDT_{EH}PhNPh_2$ (240 mg, 0.28 mmol), Pd(PPh$_3$)$_4$ (0.025 g, 0.02 mmol), xylenes (4 mL), and sealed with a Teflon cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with CHCl$_3$ (5% Et$_3$N). All volatiles were removed in vacua to give the crude product as a dark solid. The material was then loaded onto silica and purified by flash chromatography using a hexanes/CHCl$_3$ (5% Et$_3$N) gradient. After fraction collection and solvent removal a dark purple film was obtained. The film was slurried in MeOH (300 mL), sonicated for 10 minutes, and filtered. The solid was washed with copious amounts of MeOH and then dried under vacuum for 24 hours. The product was collected as a dark metallic flakey solid was obtained. Recovered yield: 250 mg (92%). $^1$H NMR ($CD_2Cl_2$): δ 8.86 (s, 2H, BDT), 8.73 (s, 2H, PT), 8.71 (m, J=6 Hz, 2H, CDT), 7.52 (m, 2H, Ph), 7.50 (m, 2H, Ph), 7.23 (m, $^3J_{H-H}$=8 Hz, 8H, Ph), 7.22 (br s, 2H, CDT), 7.13 (m, $^3J_{H-H}$=8 Hz, 8H, Ph), 7.07 (m, 8H, Ph), 4.46 (t, $^3J_{H-H}$=6 Hz, 4H, $OCH_2$), 2.09 (m, 4H), 2.01 (m, 8H), 1.73 (m, 4H), 1.48 (m, 8H), 1.08-0.94 (m, 34H), 0.84 (m, 6H), 0.74 (m, 6H), 0.66 (m, 18H). $^{13}C\{^1H\}$ NMR ($CD_2Cl_2$): 162.33, 159.95, 155.67, 148.66, 148.30, 148.03, 147.99, 147.78, 145.15, 144.89 (quaternary), 143.26 (BDT-CH), 142.14, 137.55, 136.13, 133.83, 130.25 (quaternary), 129.92 (Ph-CH), 129.51 (quaternary), 1:28.52 (t, CDT-CH), 126.75, 125.23, 124.05, 123.87 (Ph-CH), 122.18 (PT-CH), 119.49 (quaternary), 118.36 (t, CDT-CH), 74.88 ($OCH_2$), 54.85 (CDT-bridge), 43.71, 43.64 (d, 2-ethylhexyl-CH), 36.00, 34.82, 34.77, 34.75, 32.37, 31.22, 29.27, 29.10, 28.15, 28.05, 26.50, 23.42, 23.40 ($CH_2$), 14.53, 14.42, 14.37, 11.15, 11.04 ($CH_3$). Anal Calcd. for $C_{118}H_{134}N_8O_2S_8$: C, 72.57; H, 6.92; N, 5.74. Found: C, 72.8; H, 6.55; N, 5.24%. Absorbance: (CHCl$_3$) $\lambda_{max}$=675 nm, $\lambda_{onset}$=766 nm, ε=56 000 cm$^{-1}$M$^{-1}$. (As Cast Film) $\lambda_{max}$=705, 665 nm, $\lambda_{onset}$=820 nm.

Figure 9:
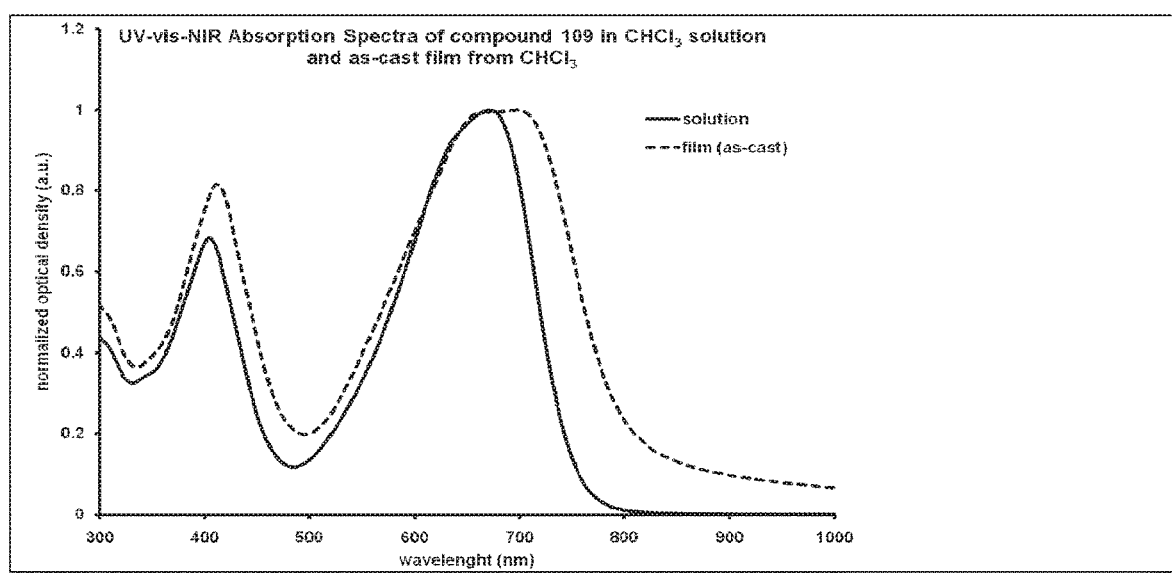
FIG. 9 shows a UV-VIS-NIR absorption spectrum of compound 109 in CHCl$_3$ solution and of a film of compound 109 as-cast from CHCl$_3$ solution.

The UV-VIS-NIR absorption spectrum of 109 in CHCl$_3$ solution and of a film of 109 as-cast from CHCl$_3$ solution is shown in FIG. 9.

Example 10

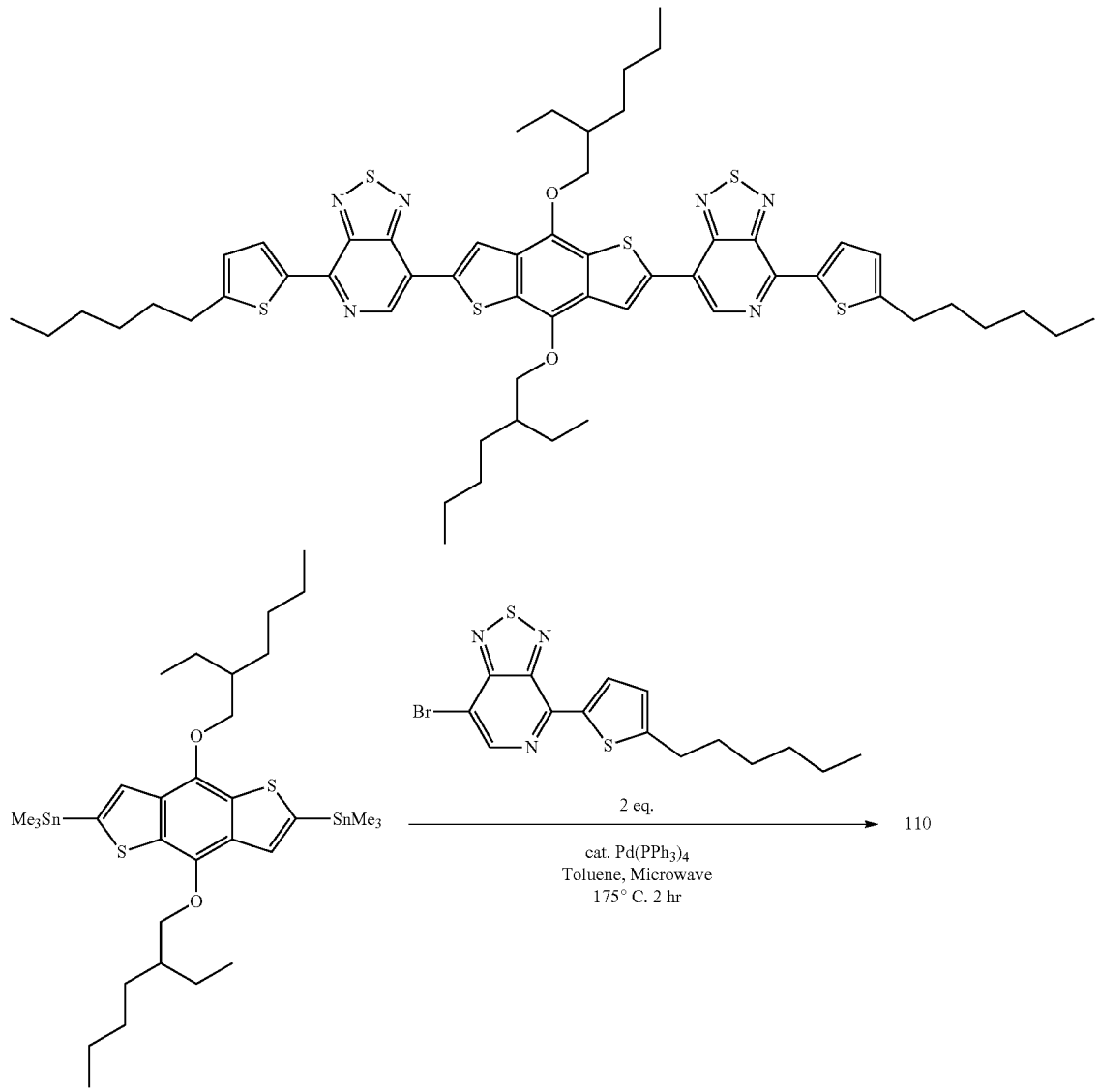

Synthesis of 110: In a N₂ filled glove box a 5 mL microwave tube was charged with Me₂Sn-BDT$_{EH}$-SnMe₃ (300 mg, 0.39 mmol), HexTPTBr (326 mg, 0.85 mmol), Pd(PPh₃)₄ (0.025 g, 0.02 mmol), xylenes (4 mL), and sealed with a Teflon cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with CHCl₃ (5% Et₃N) (500 mL). All volatiles were removed in vacuo to give the crude product as a purple solid. The material was then loaded onto silica and purified by flash chromatography using a hexanes/CHCl₃ (5% Et₃N) gradient. After fraction collection and solvent removal a purple solid was obtained. Purification by silica column chromatography was carried out twice to ensure complete removal of all trace impurities and by-products. The solid was slurried in MeOH (300 mL), sonicated for 10 minutes, and filtered. The solid was washed with copious amounts of MeOH and then dried under vacuum for 24 hours. The product was collected as a purple solid. Recovered yield: 390 mg (96%). ¹H NMR (CDCl₃): δ 8.45 (s, 2H, PT-CH), 8.31 (s, 2H, BDT-CH), 8.19 (d, ³J$_{H-H}$=5 Hz, 2H Th-CH), 6.66 (d, ³J$_{H-H}$=5 Hz, 2H Th-CH), 4.22 (br m, 4H, OCH), 2.76 (m, 4H, Th-CH₂), 1.86 (br m, 4H, CH₂), 1.79-1.60 (m, 10H, CH₂), 1.54 (br m, 8H, CH₂), 1.39 (br m, 4H, CH₂), 1.33 (br m, 8H, CH₂), 1.16 (t, ³J$_{H-H}$=8 Hz, 6H, CH₃), 1.06 (t, ³J$_{H-H}$=5 Hz, 6H, CH₃), 0.92 (m, ³J$_{H-H}$=8 Hz, 6H, CH₃). ¹³C{¹H} NMR (CDCl₃): 154.37, 152.45, 147.74, 146.25, 144.27, 142.84 (s, quaternary), 141.48 (CH), 138.81, 135.52, 132.86 (s, quaternary), 132.11 (CH), 128.70 (s, quaternary), 126.10, 122.13 (CH), 119.28 (s, quaternary). Anal. Calcd. for C₅₆H₆₈N₆O₂S₆: C, 64.08; H, 6.53; N, 8.01. Found: C, 64.0; H, 6.35; N, 8.10%. Absorbance: (CHCl₃) λ$_{max}$=560 nm, λ$_{onset}$=670 nm. (As Cast Film) λ$_{max}$=590, 630 nm, λ$_{onset}$=725 nm.

Figure 10:
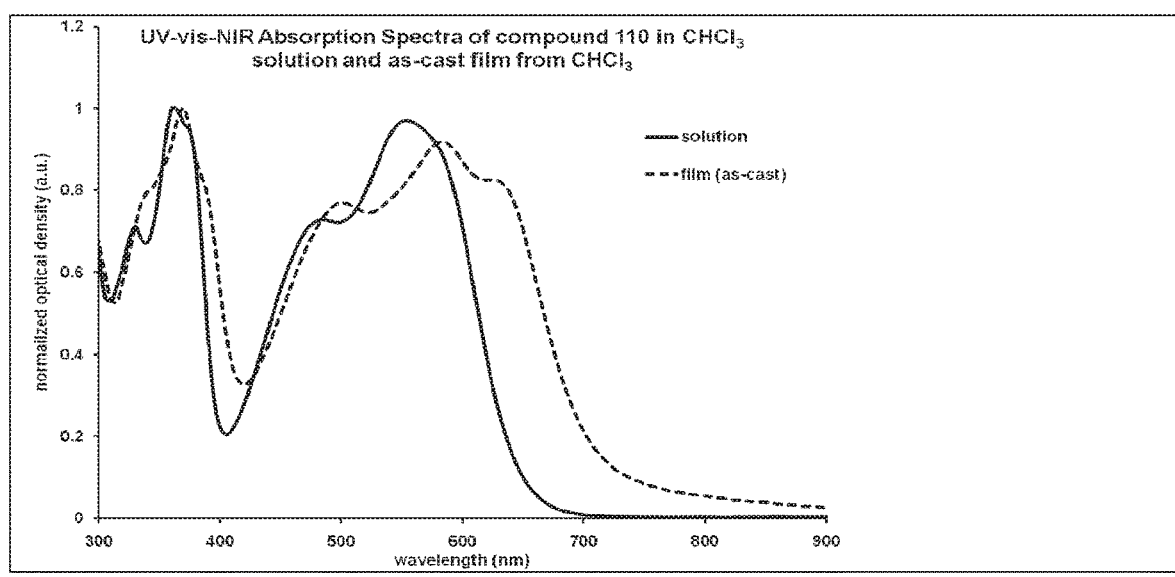
FIG. 10 shows a UV-VIS-NIR absorption spectrum of compound 110 in CHCl$_3$ solution and of a film of compound 110 as-cast from CHCl$_3$ solution.

The UV-VIS-NIR absorption spectrum of 110 in CHCl₃ solution and of a film of 110 as-cast from CHCl₃ solution is shown in FIG. 10.

Example 11

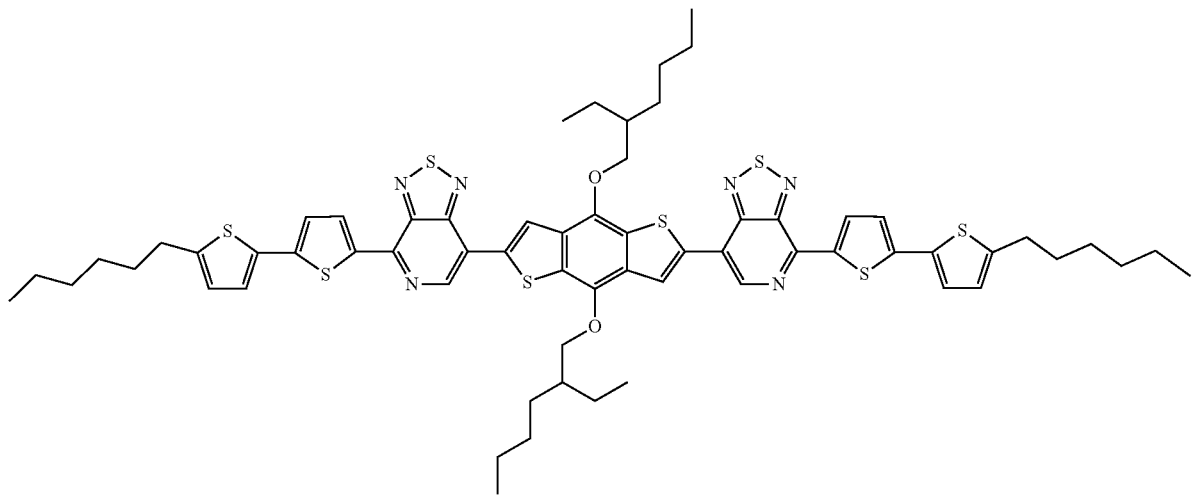

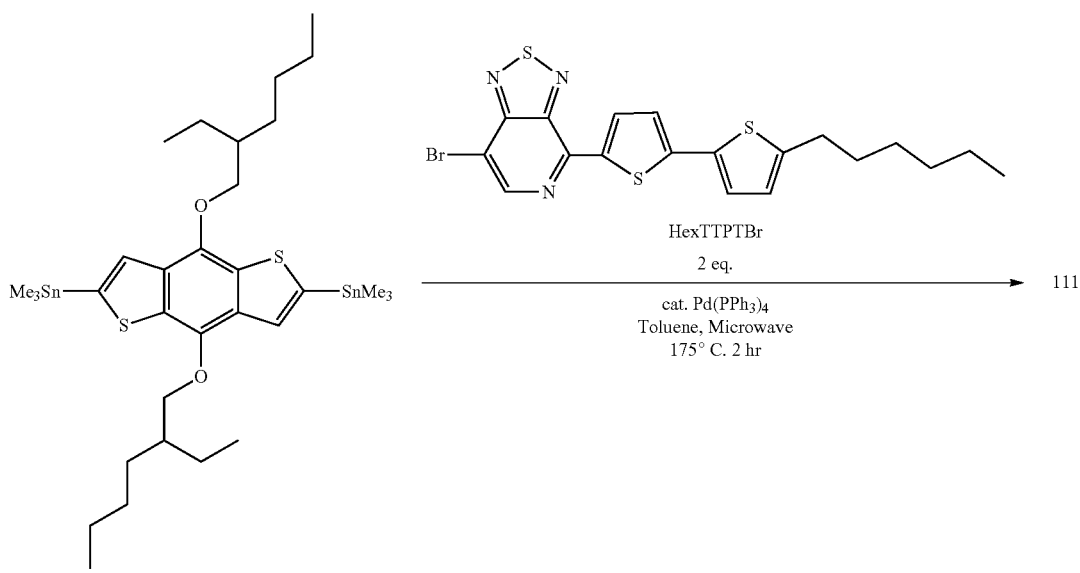

Synthesis of 111: In a N₂ filled glove box a 5 mL microwave tube was charged with Me₃Sn-BDT$_{EH}$-SnMe₃ (191 mg, 0.27 mmol), HexTTPTBr (230 mg, 0.50 mmol), Pd(PPh₃)₄ (0.025 g, 0.02 mmol), xylenes (4 mL), and sealed with a Teflon cap. The reaction mixture was heated to 120° C. for 3 minutes, 140° C. for 3 minutes, and 175° C. for 120 minutes, using a Biotage microwave reactor. Upon cooling, the residue was transferred to a 500 mL round bottom flask using CHCl₃ and all volatiles removed in vacuo to give the crude product as a purple solid. The solid was slurried in MeOH (300 mL), sonicated for 10 minutes, and filtered. The solid was washed with copious amounts of MeOH, Acetone, iPrOH, hexanes using a soxhelt apparatus and then dried under vacuum for 24 hours. The product was collected as a purple solid. Recovered yield: 170 mg (57%). Compound 111 exhibits very low solubility in organic solvents (<5 mg/mL in CHCl₃) and minimal movement on silica-gel.

Figure 11:
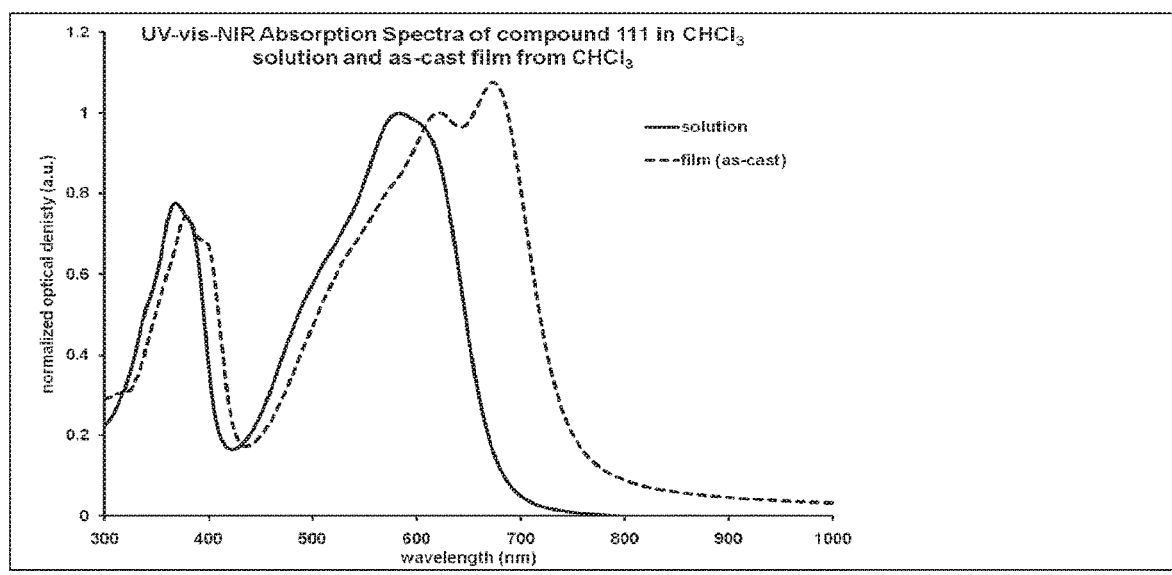
FIG. 11 shows a UV-VIS-NIR absorption spectrum of compound 111 in CHCl$_3$ solution and of a film of compound 111 as-cast from CHCl$_3$ solution.

The UV-VIS-NIR absorption spectrum of 111 in CHCl₃ solution and of a film of 111 as-cast from CHCl₃ solution is shown in FIG. 11.

Example 12

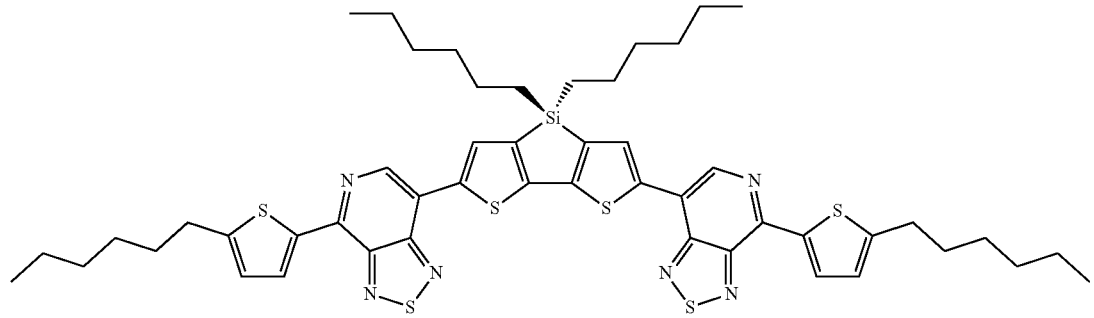

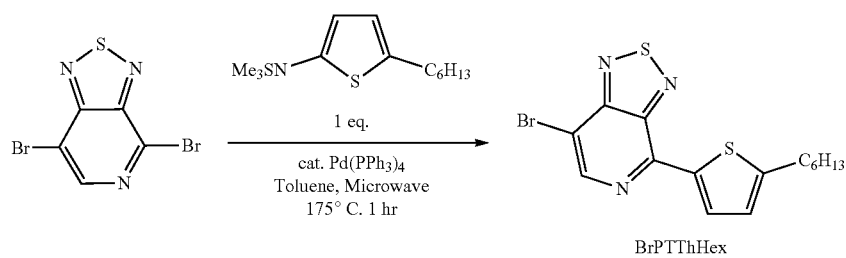

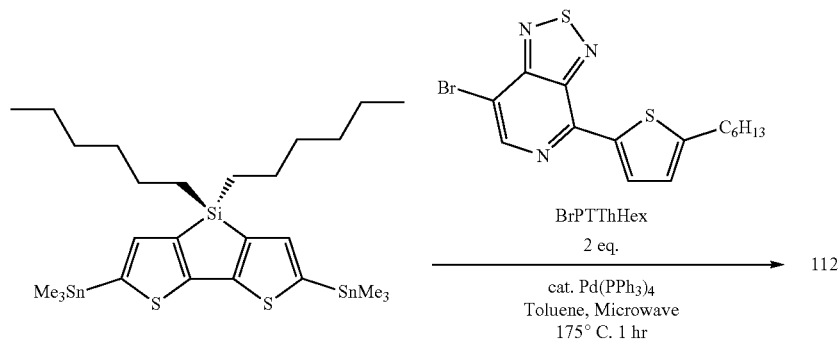

Synthesis of 112: In a filled glove box a 20 mL microwave tube was charged with 5,5'-Bis(trimethylstannyl)-3,3'-di-2-hexylsilylene-2,2'-bithiophene (Me$_3$Sn-SDT$_{Hex}$-SnMe$_3$, 500 mg, 0.73 mmol), 7-bromo-4-(5-hexylthiophen-2-yl)-[1,2,5]thiadiazolo[3,4-c]pyridine (HexThPTBr, 560 mg, 1.46 Pd(PPh$_3$)$_4$ (0.025 g, 0.02 mmol), toluene (15 mL), and sealed with a Teflon® cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with CHCl$_3$ (5% Et$_3$N) (500 mL). All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 480 mg (69%). $^1$H NMR (CDCl$_3$): δ 8.60 (s, 2H, PT-CH), 8.36 (d, $^3J_{H\text{-}H}$=5 Hz, 2H, Th-CH), 8.15 (t, 2H, SDT-CH), 6.90 (d, $^3J_{H\text{-}H}$=5 Hz, 2H, Th-CH), 2.90 (t, $^3J_{H\text{-}H}$=7 Hz, 4H Th-CH$_2$), 1.79 (tt, $^3J_{H\text{-}H}$=7 Hz, 4H, CH$_2$), 1.56 (m, 4H, CH), 1.44 (br m, 8H, CH$_2$), 1.36 (m, 8H, CH$_2$), 1.32 (m, 8H, CH$_2$), 1.10 (m, 4H, SiCH$_2$), 0.92 (m, 6H, CH$_3$), 0.88 (m, 6H, CH$_3$). $^{13}$C{$^1$H} NMR (CDCl$_3$): 154.25, 152.97, 150.47, 147.69, 145.35, 143.97 (s, quaternary), 139.96 (s, CH), 139.10, 138.65 (s, quaternary), 131.96 (s, CH), 130.63 (s, CH), 126.30 (s, CH), 119.99 (s, quaternary), 32.99 (s, CH$_2$), 31.57 (s, CH$_2$), 31.51 (s, CH$_2$), 30.39 (s, CH$_2$), 30.56 (s, CH$_2$), 28.81 (s, CH$_2$), 24.29 (s, CH$_2$), 26.61 (s, CH$_2$), 22.57 (s, CH$_2$), 14.11 (s, CH$_2$), 14.07 (s, CH$_3$), 11.99 (s, CH$_3$). Anal, Calcd, for C$_{50}$H$_{60}$N$_6$S$_6$Si: C, 62.20; H, 6.26; N, 8.70. Found: C, 62.2; H, 6.16; N, 8.67%. Absorbance: (CHCl$_3$) $\lambda_{max}$=600 nm, $\lambda_{onset}$=715 nm. (As Cast Film) $\lambda_{max}$=625, 675 nm, $\lambda_{onset}$=795 nm.

Figure 12:
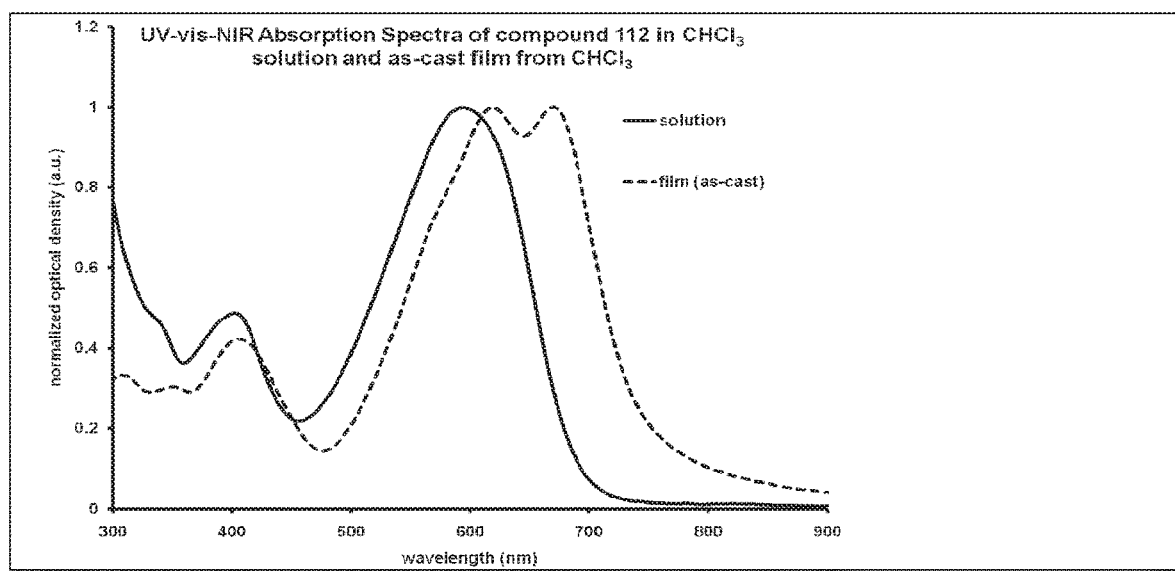
FIG. 12 shows a UV-VIS-NIR absorption spectrum of compound 112 in CHCl₃ solution and of a film of compound 112 as-cast from CHCl₃ solution.

The UV-VIS-NIR absorption spectrum of 112 in CHCl$_3$ solution and of a film of 112 as-cast from CHCl$_3$ solution is shown in FIG. 12.

Example 13

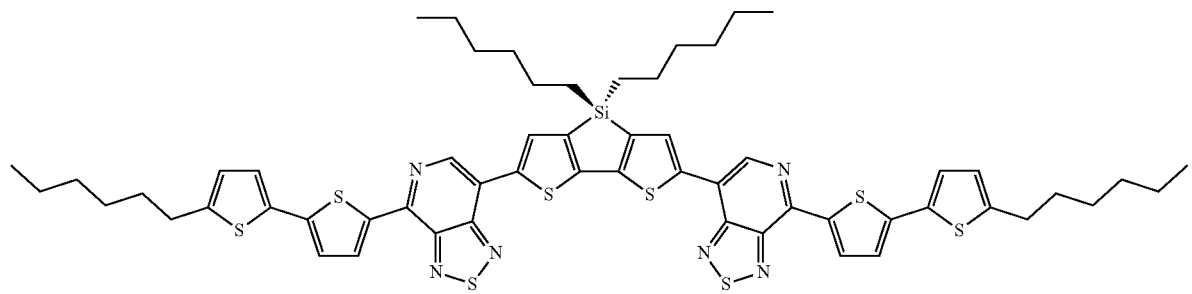

113

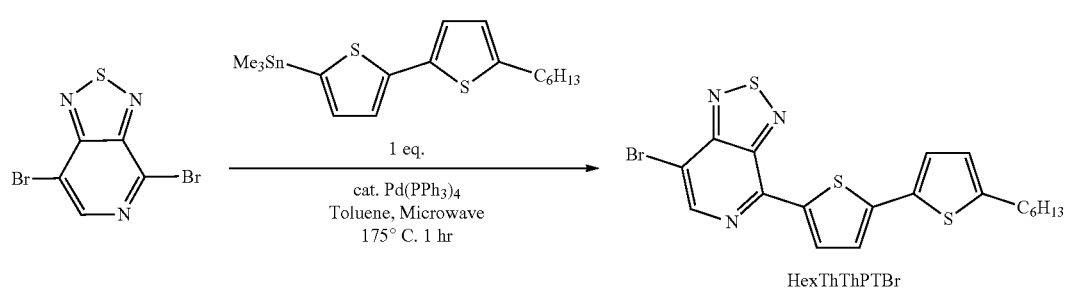

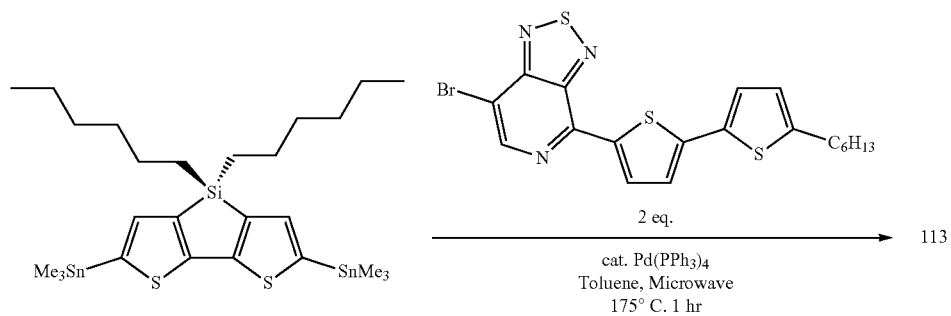

Synthesis of 113: In a N$_2$ filled glove box a 20 mL microwave tube was charged with 5,5'-Bis(trimethylstannyl)-3,3'-dihexylsilylene-2,2'-bithiophene (Me$_3$Sn-SDT$_{HEX}$-SnMe$_3$, 394 mg, 0.57 mmol), 7-bromo-4-(5-(5-hexylthiophen-2-yl)thiophen-2-yl)-[1,2,5]thiadiazolo[3,4-c]pyridine (HexThThPTBr, 530 mg, 1.14 mmol), Pd(PPh$_3$)$_4$ (0.025 g, 0.02 mmol), toluene (15 mL), and sealed with a Teflon cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with CHCl$_3$ (5% Et$_3$N) (500 mL). All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 520 mg (80%). $^1$H NMR (CDCl$_3$): δ 8.64 (s, 2H, PT-CH), 8.44 (m, 2H, Th-CH), 8.11 (m, 2H, SDT-CH), 7.16 (d, $^3J_{H-H}$=5 Hz, 2H Th-CH), 7.15 (d, $^3J_{H-H}$=5 Hz, 2 Hz, Th-CH), 6.72 (m, 2H, Th—CH), 2.81 (t, $^3J_{H-H}$=7 Hz, 4H Th-CH$_2$), 1.73 (tt, $^3J_{H-H}$=6 Hz, 4H, CH$_2$), 1.57 (m, 4H, CH$_2$), 1.41 (br m, 8, CH$_2$), 1.33 (br m, 16H, CH$_2$), 1.10 (m, 4H, CH$_2$), 0.93 (m, 6H, CH$_3$), 0.88 (m 6H, CH$_3$). Absorbance: (CHCl$_3$) λ$_{max}$=630 nm, λ$_{onset}$=735 nm. (As Cast Film) λ$_{max}$=660, 715 nm, λ$_{onset}$=800 nm.

Figure 13:
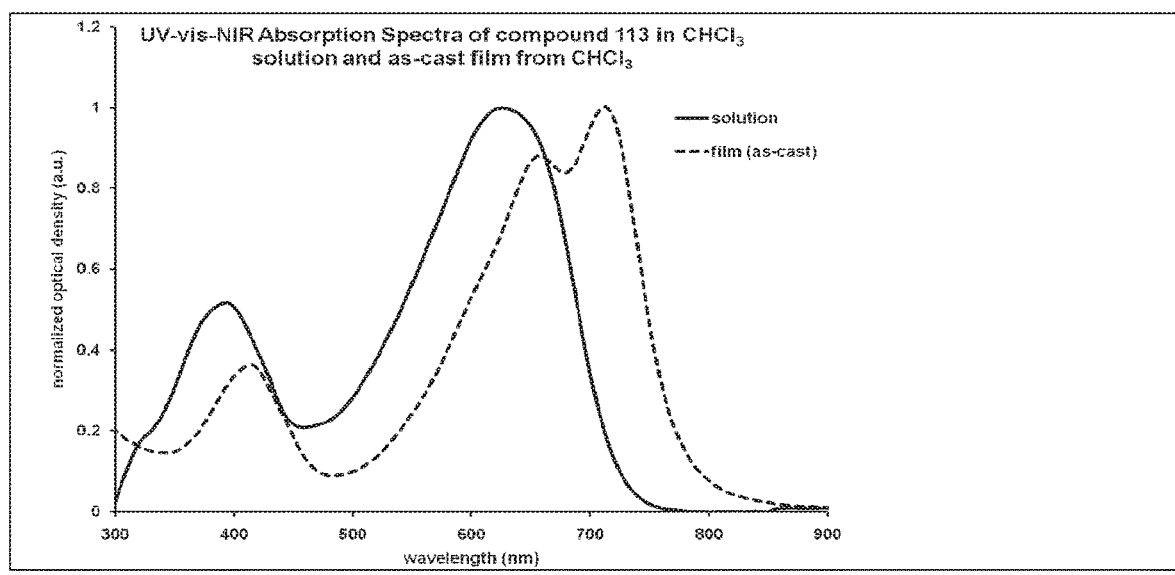
FIG. 13 shows a UV-VIS-NIR absorption spectrum of compound 113 in CHCl₃ solution and of a film of compound 113 as-cast from CHCl₃ solution.

The UV-VIS NIR absorption spectrum of 113 in CHCl$_3$ solution and of a film of 113 as-cast from CHCl$_3$ solution is shown in FIG. 13.

Example 14

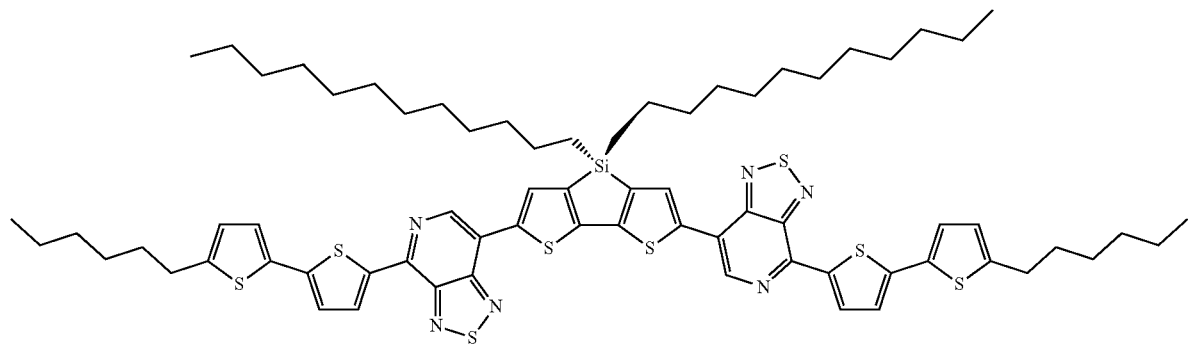

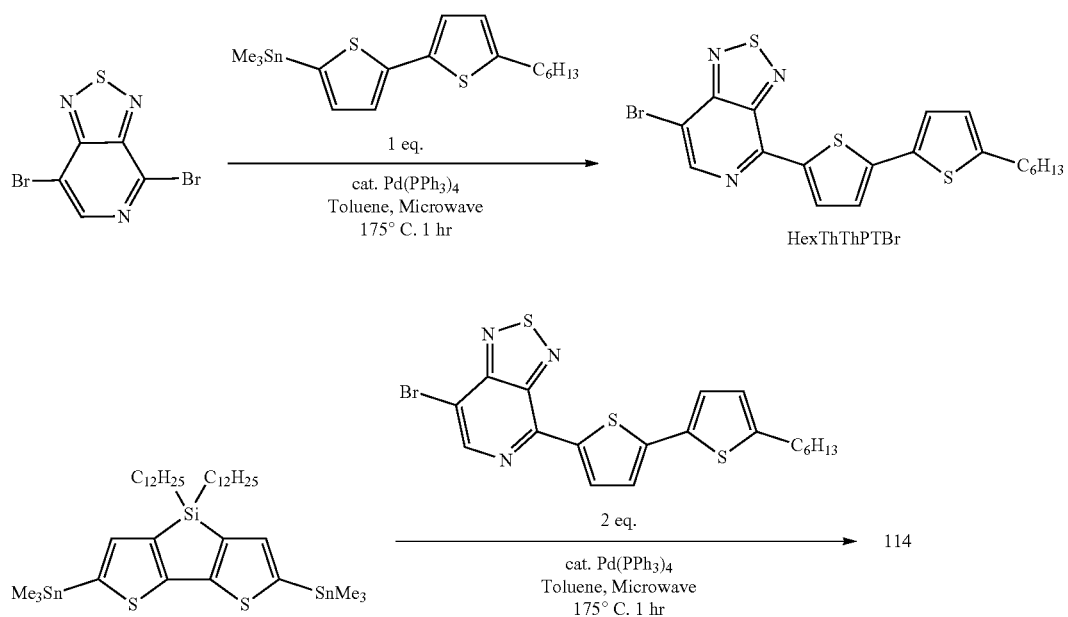

Synthesis of 114: In a $N_2$ filled glove box a 5 mL microwave tube was charged with 5,5'-Bis(trimethylstannyl)-3,3'-di-2-dodecilsilylene-2,2'-bithiophene ($Me_3Sn$-$SDT_{C12}$-$SnMe_3$, 370 mg, 0.43 mmol), 7-bromo-4-(5-(5-hexylthiophen-2-yl)thiophen-2-yl)-[1,2,5]thiadiazolo[3,4-c]pyridine (HexThThPTBr, 400 mg, 0.86 mmol), Pd(PPh$_3$)$_4$ (0.025 g, 0.02 mmol), toluene (4 mL), and sealed with a Teflon cap. The reaction mixture was heated to 120° C. for 3 minutes, 140° C. for 3 minutes, and 175° C. for 60 minutes, using a Biotage microwave reactor. Upon cooling, the residue was passed through a short silica plug eluting with CHCl$_3$ (5% Et$_3$N) (500 mL). All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 500 mg (89%). $^1$H NMR (CDCl$_3$): δ 8.57 (s, 2H, PT-CH), 8.36 (d, $^3J_{H-H}$=5 Hz, 2H, Th-CH), 8.09 (m, 2H, SDT-CH), 7.13 (d, $^3J_{H-H}$=5 Hz, 4H Th-CH), 6.71 (m, 2H, Th-CH), 2.81 (m, 4H Th—CH$_2$), 1.71 (m, 4H, CH$_2$), 1.59 (m, 4H, CH$_2$), 1.43 (br m, 8H, CH$_2$), 1.35 (m, 12H, CH$_2$), 1.24 (br m, 28H, CH$_2$), 1.11 (m, 4H, CH$_2$), 0.93 (m, 6H, CH$_3$), 0.85 (m, 6H, CH$_3$). Anal. Calcd. for C$_{70}$H$_{88}$N$_6$S$_8$Si: C, 64.77; H, 6.83; N, 6.47. Found: C, 64.5; H, 6.90; N, 6.56%. Absorbance: (CHCl$_3$) λ$_{max}$=630 nm, λ$_{onset}$=750 nm. (As Cast Film) λ$_{max}$=655, 715 nm. λ$_{onset}$=825 nm.

Figure 14:
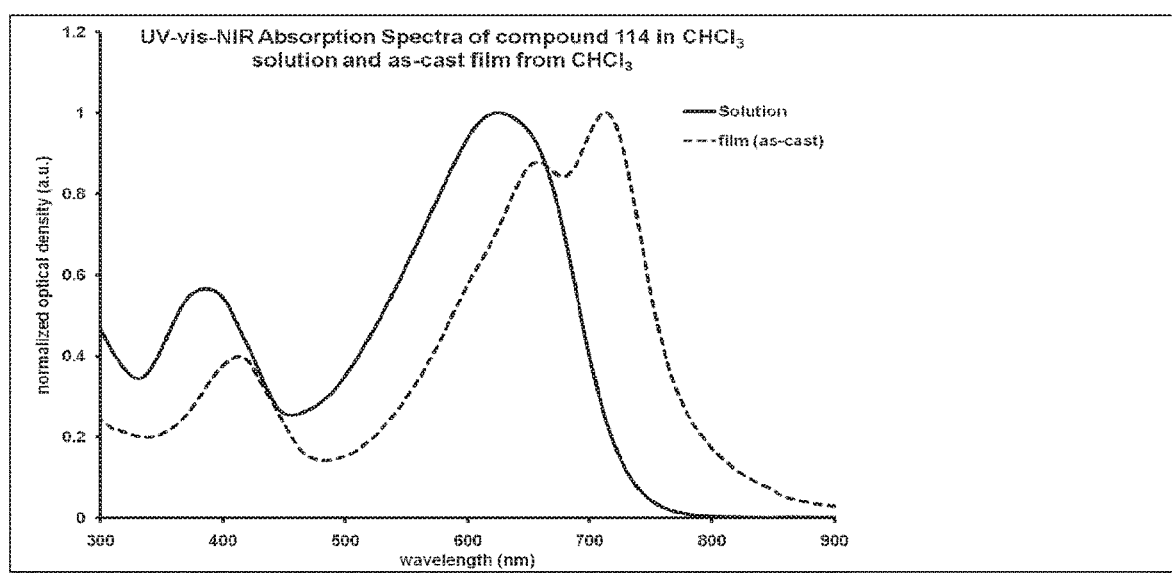
FIG. 14 shows a UV-VIS-NIR absorption spectrum of compound 114 in CHCl₃ solution and of a film of compound 114 as-cast from CHCl₃ solution.

The UV-VIS-NIR absorption spectrum of 114 in CHCl$_3$ solution and of a film of 114 as-cast from CHCl$_3$ solution is shown in FIG. 14.

Example 15

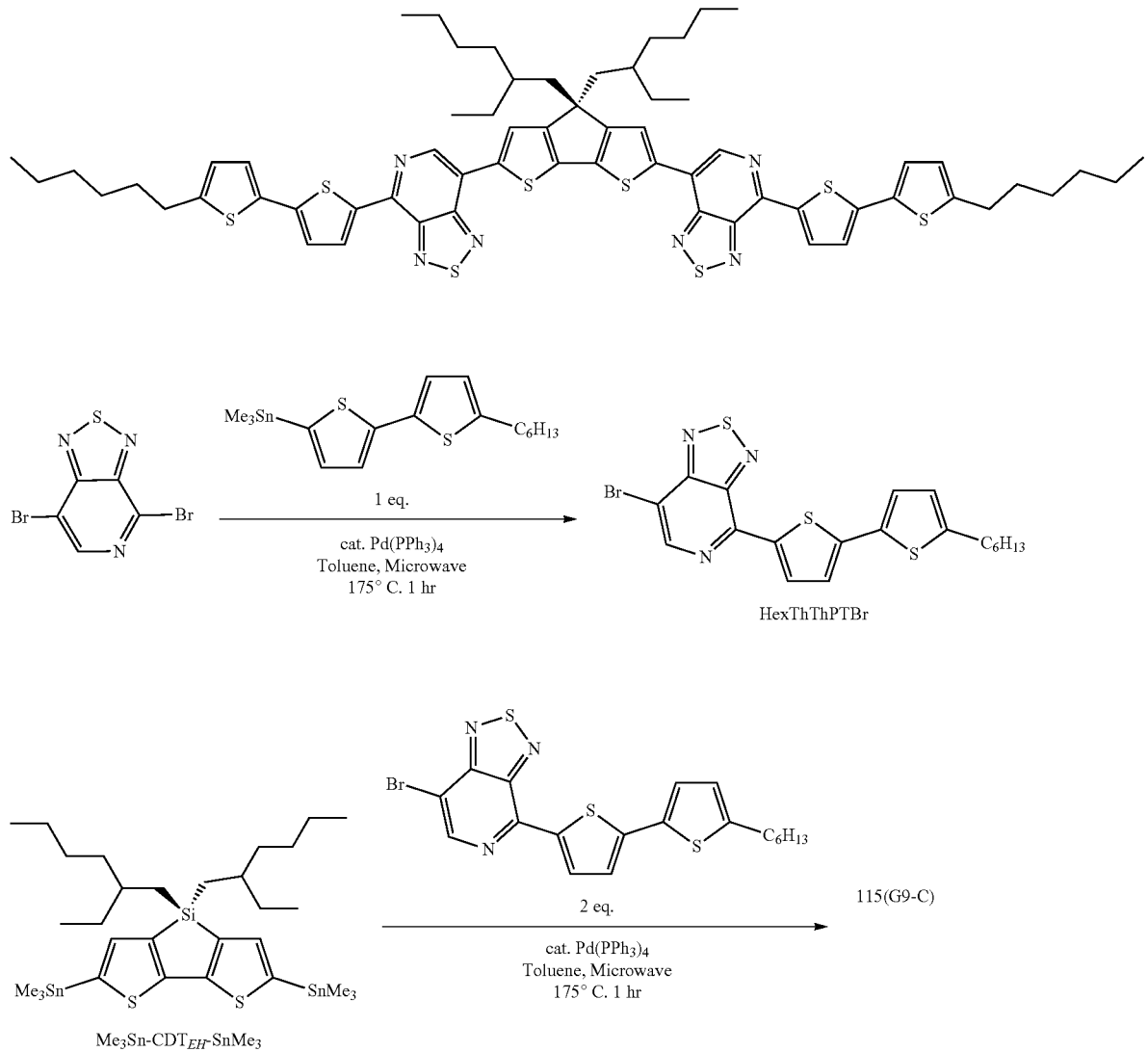

Synthesis of 11.5 (G9-C): In a $N_2$ filled glove box a 20 mL microwave tube was charged with 4,4-bis(2-ethylhexyl)-2,6-bis(trimethylstannyl)-4H-cyclopenta[2,1-b:3,4-b']dithiophene ($Me_3Sn\text{-}CDT_{EH}\text{-}SnME_3$, 520 mg, 0.71 mmol), 7-bromo-4-(5-(5-hexylthiophen-2-yl)thiophen-2-yl)-[1,2,5]thiadiazolo[34-c]pyridine (HexThThPTBr, 637 mg, 1.37 mmol), Pd(PPh$_3$)$_4$ (0.025 g, 0.02 mmol), toluene (15 mL), and sealed with a Teflon cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with CHCl$_3$ (5% Et$_3$N) (500 mL). All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. Purification by silica column chromatography was carried our twice. The solid was slurried in MeOH (300 sonicated for 10 minutes, and filtered. The solid was washed with copious amounts of MeOH and then dried under vacuum for 24 hours. The product was collected as purple solid. Recovered yield: 710 mg (85%). $^1$H NMR (CDCl$_3$): δ 8.83 (s, 2H, PT-CH), 8.58 (d, $^3J_{H\text{-}H}$=5 Hz, 2H, Th-CH), 8.10 (t, 2H, SDT-CH), 7.25 (d, $^3J_{H\text{-}H}$=5 Hz, 2 Hz, Th-CH), 7.19 (d, $^3J_{H\text{-}H}$=5 Hz, 2H Th-CH), 6.76 (m, 2H, Th-CH), 2.84 (m, 4H Th-CH$_2$), 2.08 (m, 4H, CH$_2$), 1.72 (tt, $^3J_{H\text{-}H}$=6 Hz, 4H, CH$_2$), 1.42 (m, 4H, CH), 1.35 (m, 8H, CH$_2$), 1.05-1.00 (br m, 14H, CH$_2$), 0.92 (m, 6H, CH$_2$), 0.84 (m, 4H, CH$_2$), 0.66 (m, 12H, CH$_3$). Absorbance: (CHCl$_3$) $\lambda_{max}$=655 nm, X$_{onset}$=765 nm. (As Cast Film) $\lambda_{max}$=680, 740 nm, $\lambda_{max}$=845 nm.

Figure 15:
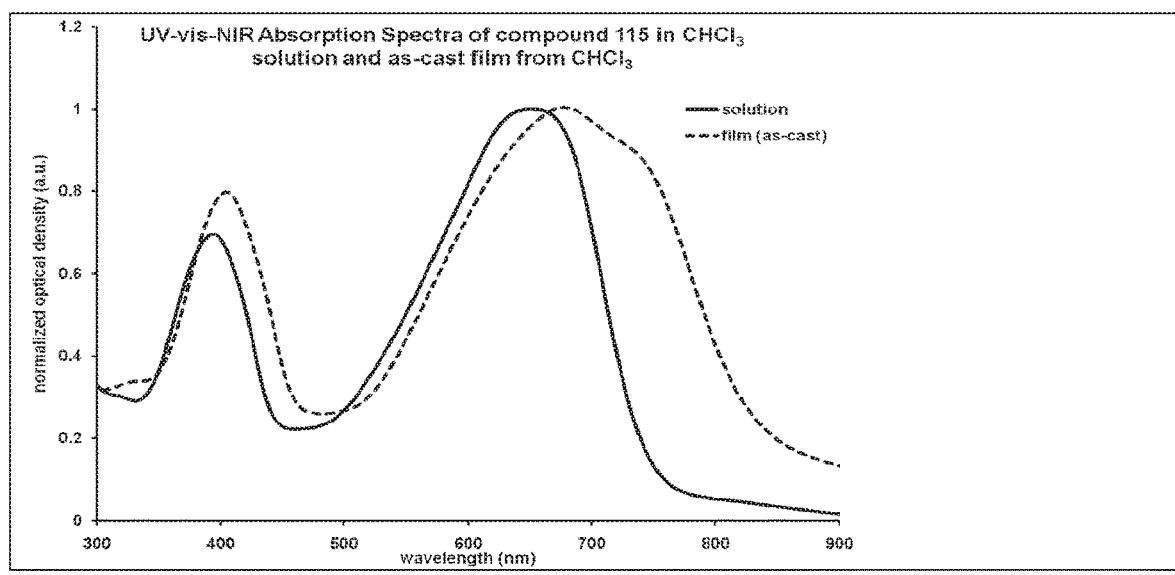
FIG. 15 shows a UV-VIS-NIR absorption spectrum of compound 115 in CHCl₃ solution and of a film of compound 115 as-cast from CHCl₃ solution.

The UV-VIS-NIR absorption spectrum of 115 in CHCl$_3$ solution and of a film of 115 as-cast from CHCl$_3$ solution is shown in FIG. 15.

Example 16

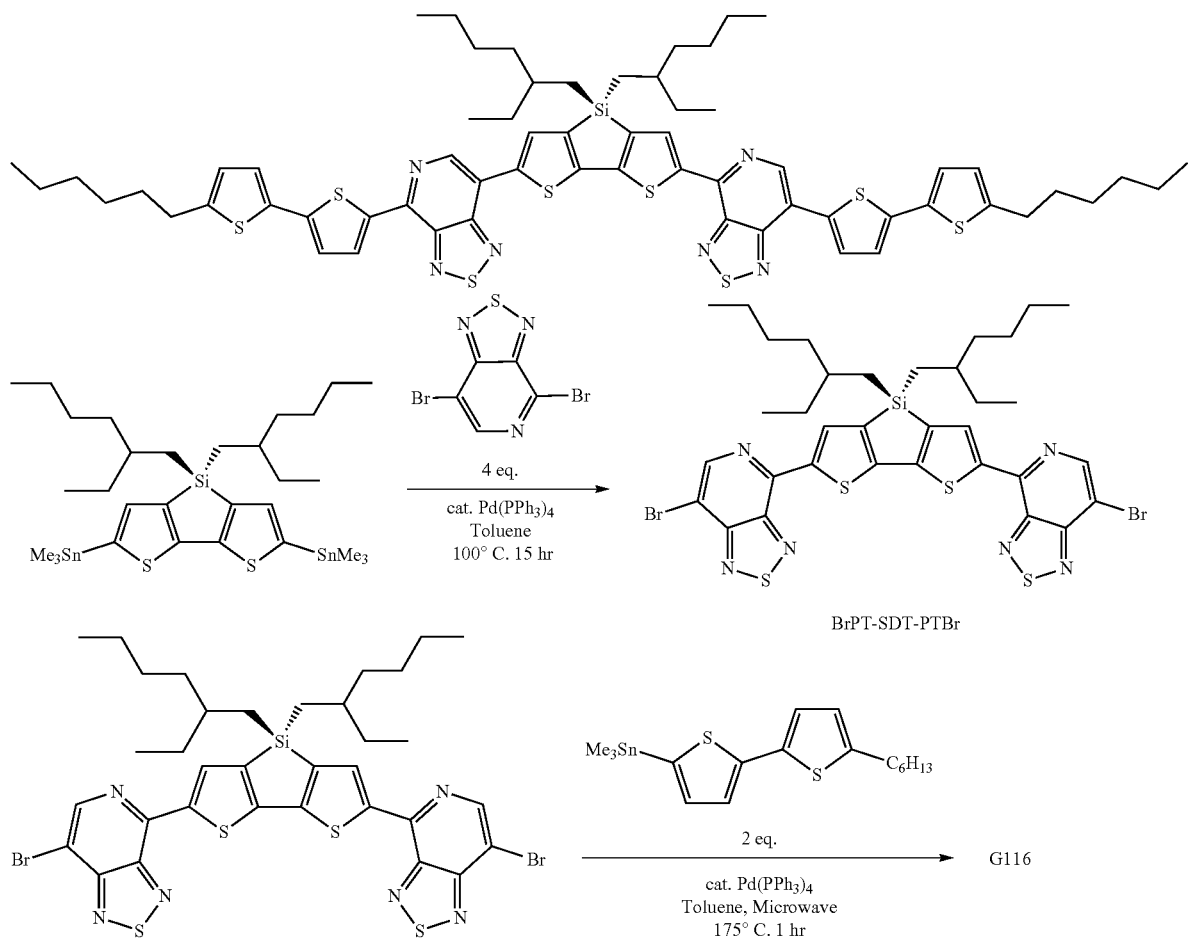

Synthesis of BrPT-SDT-PTBr: In a $N_2$ filled glove box a 20 mL glass tube was charged with 4,7-dibromo-pyridal[2,1,3]thiadiazole (PTBr$_2$, 1.27 g, 4.31 mmol), 5,5'-Bis(trimethylstannyl)-3,3'-di-2-ethylhexylsilylene-2,2'-bithiophene (Me$_3$Sn-SDT$_{EH}$-SnMe$_3$, 800 mg, 1.07 mmol), Pd(PPh$_3$)$_4$ (0.025 g, 0.02 mmol), toluene (15 mL), and sealed with a Teflon cap. The reaction mixture was heated to 100° C. for 15 hours, during which a color change from yellow to purple was observed. Upon cooling, the residue was passed through a short silica plug eluting with CHCl$_3$ (5% Et$_3$N) (500 mL). All volatiles were removed in vacuo to give the crude product as a dark sticky solid. The material was then loaded onto silica and purified by flash chromatography using a hexanes/CHCl$_3$ (5% Et$_3$N) gradient. The product eluted as a purple solution at 80% CHCl$_3$ (5% Et$_3$N). After fraction collection and solvent removal, the solid product was slurried in MeOH (300 mL), sonicated for 10 minutes, and filtered. The solid was washed with copious amounts of MeOH and then dried under vacuum for 24 hours. The product was collected as green metallic coloured powder. Recovered yield: 550 mg (60%). $^1$H NMR (CDCl$_3$): δ 8.76 (s, 2H, PT-CH), 8.66 (s, 2H, SDT-CH), 1.52 (m, 2H, CH), 1.39 (m, 4H, CH$_2$), 1.31 (m, 4H, CH$_2$), 1.16 (m, 8H, CH$_2$), 1.06 (m, 4H, CH$_2$), 0.85 (m, 12H, CH$_3$). $^{13}$C{$^1$H} NMR (CDCl$_3$): 156.38, 153.85, 147.98, 147.66, 147.49 (s, quaternary), 146.03 (s, CH), 143.94 (s, quaternary), 135.99 (s, CH), 107.64 (s, quaternary), 36.02 (s, CH), 35.76 (s, CH$_2$), 22.97 (s, CH$_2$), 22.93 (s, CH$_2$), 20.92 (s, CH$_2$), 17.64 (s, CH$_2$), 14.15 (s, CH$_3$), 10.80 (s, CH$_3$).

Synthesis of 116: In a $N_2$ filled glove box a 5 mL microwave tube was charged with BrPT-SDT-PTBr (420 mg, 0.50 mmol), 5'-hexyl-2,2'-bithiophene 5 trimethylstannane (450 mg, 1.09 mmol), Pd(PPh$_3$)$_4$ (0.025 g, 0.02 mmol), toluene (4 mL), and sealed with a Teflon cap. The reaction mixture was heated to 120° C. for 3 minutes, 140° C. for 3 minutes, and 175° C. for 120 minutes, using a Biotage microwave reactor. Upon cooling, the residue was passed through a short silica plug eluting with CHCl$_3$ (5% Et$_3$N) (500 mL). All volatiles were removed in vacuo to give the crude product as a purple solid. The material was then loaded onto silica and purified by flash chromatography using a hexanes/CHCl$_3$ (5% Et$_3$N) gradient. After fraction collection and solvent removal a purple solid was obtained. Purification by silica column chromatography was carried out twice. The solid was slurried in MeOH (300 mL), sonicated for 10 minutes, and filtered. The solid was washed with copious amounts of MeOH and then dried under vacuum for 24 hours. The product was collected as purple solid. Recovered yield: 475 mg (81%). $^1$H NMR (CDCl$_3$): δ 8.72 (t, 2H, SUE-CH), 8.70 (s, 2H, PT-CH), 7.95 (d, $^3J_{H\text{-}H}$=5 Hz, 2H, Th-CH), 7.16 (d, $^3J_{H\text{-}H}$=5 Hz, 2H, Th-CH), 7.11 (d, $^3J_{H\text{-}H}$=5 Hz, 2H, Th-CH), 6.73 (d, $^3J_{H\text{-}H}$=5 Hz, 2H, Th-CH), 2.83 (t, $^3J_{H\text{-}H}$=8 Hz, 4H Th-CH$_2$), 1.72 (h, $^3J_{H\text{-}H}$=6 Hz, 4H, CH$_2$), 1.62 (m, 2H, CH), 1.41 (m, 8H, CH$_2$), 1.35 (m, 12H, CH$_2$), 1.28 (m, 8H, CH$_2$), 1.18 (m, 4H, SiCH$_2$), 0.92-0.83 (m, 18H, CH$_3$). $^{13}$C{$^1$H} NMR (CDCl$_3$): 154.56, 153.65, 147.98, 147.43, 146.27, 145.76, 144.77, 140.43 (s, quaternary), 139.63 (s, PT-CH), 135.19, 134.85 (s, quaternary), 134.44 (s, SDT-CH), 128.42 (s, Th-CH), 125.01 (s, Th-CH), 123.99 (s, Th-CH), 123.85 (s, Th-CH), 119.59 (s, quaternary), 36.10 (s, CH), 35.86 (s, CH$_2$), 31.57 (s, Si—CH$_2$), 30.26 (s, Th-CH$_2$), 29.08 (s, CH$_2$), 29.01 (s, CH$_2$), 28.80 (s, CH$_2$), 23.08 (s, CH$_2$), 22.59 (s, CH$_2$), 17.73 (s, CH$_2$), 14.26 (s, CH$_3$), 14.09 (s, CH$_3$), 10.88 (s, CH$_3$). Absorbance: (CHCl$_3$) $\lambda_{max}$=655 nm, $\lambda_{onset}$=715 nm, ε=37400 cm$^{-1}$ M$^{-1}$. (As Cast Film) $\lambda_{max}$=655, 725 nm, $\lambda_{onset}$=815 nm.

Figure 16:
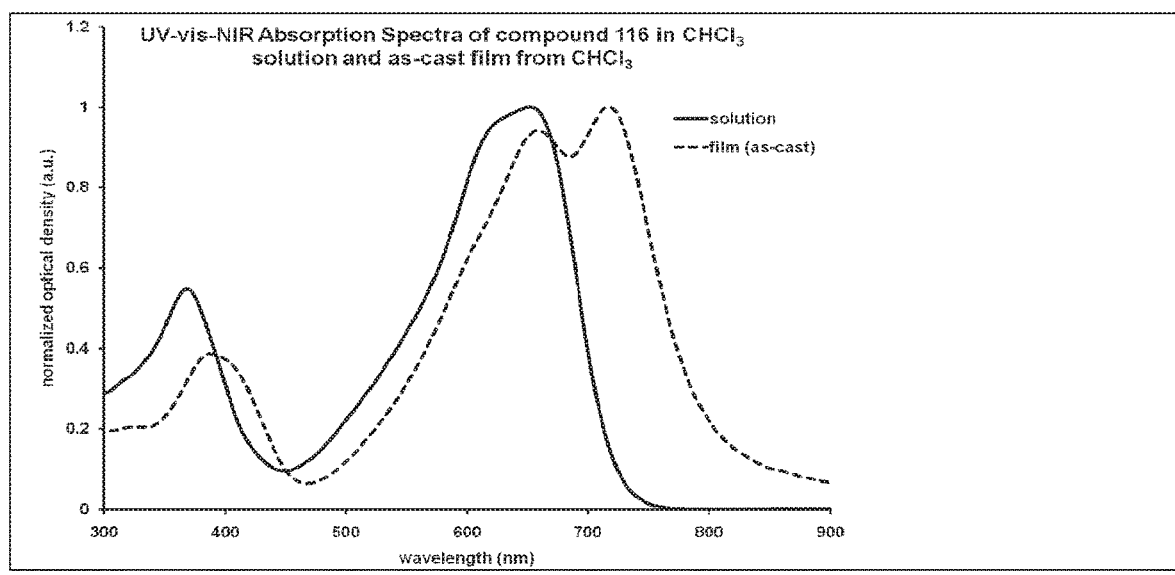
FIG. 16 shows a UV-VIS-NIR absorption spectrum of compound 116 in CHCl₃ solution and of a film of compound 116 as-cast from CHCl₃ solution.

The UV-VIS-NIR absorption spectrum of 116 in CHCl$_3$ solution and of a film of 116 as-cast from CHCl$_3$ solution is shown in FIG. 16.

Example 17

Determination of HOMO-LUMO Values

Electrochemistry: All electrochemical measurements were performed using CHI instrument model 730B in a standard three-electrode, one compartment configuration equipped with Ag/AgCl electrode, Pt wire and Glassy carbon electrode (dia. 3 mm), as the pseudo reference, counter electrode and working electrode respectively. Glassy carbon electrodes were polished with alumina. The cyclic voltammetry (CV) experiments were performed in anhydrous dichloromethane (DCM) solution with 0.1 M tetrabutylammonium hexafluorophosphate (TBAPF$_6$) as the supporting electrolyte at scan rate 100 mV/s unless otherwise stated. All electrochemical solutions were purged with dry Ar for 15 minutes at least to deoxygenate the system. Under these conditions, a Fc/Fc$^+$ standard was calibrated to be 0.40 V. In solution, monomer concentration was about ~10$^{-3}$ M.

Calculations: All calculations were performed using the Gaussian 03 program. Optimized gas-phase structures were obtained using the density functional theory (DFT) method B3LYP in conjunction with 6-31G(d,p) basis set, i.e., B3LYP/6-31G(d,p). California NanoSystems Institute at UCSB is acknowledged for computational resources.

Figure 17:
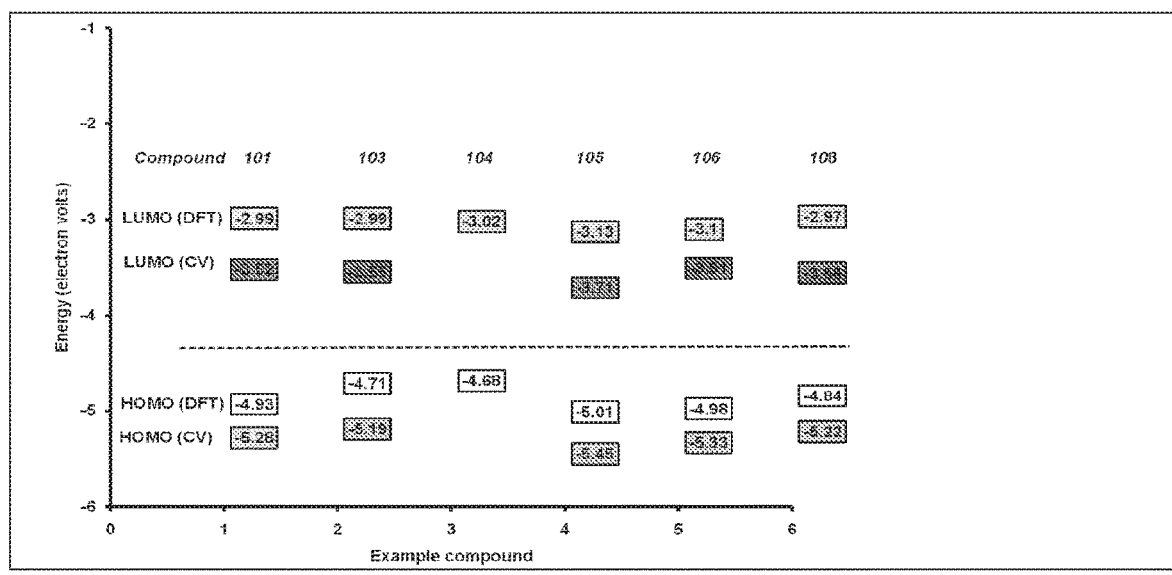
FIG. 17 shows a plot of HOMO-LUMO energy revels.

FIG. 17 shows highest occupied molecular orbital (HOMO) and lowest unoccupied molecular orbital (LUMO) values measured electrochemically and calculated using the method above for example compounds 101, 103, 104, 105, 106, 108.

Example 18

General Procedures for Fabrication of Devices

Device Fabrication: Indium tin oxide (ITO) substrates were prepared by wet cleaning and then UV/ozone treatment. A 50 nm hole injection layer (Plextronics Plexcore OC AQ-1300) was spin coated on top of an ITO substrate. A solution of filtered (1 μm Whatman PTFE filter) 103:PC$_{71}$BM with varied ratios in chloroform was spin coating onto the ITO/PEDOT:PSS substrate at varied spin speeds for different thicknesses. The PC$_{71}$BM was 99% pure and used as received from Solenne, and chloroform was used as received from Sigma-Aldrich Inc. The 103:PC$_{71}$BM films thicknesses were determined by profilometry. Devices had a 13 mm$^2$ area Al cathode evaporated on top of the 103:PC$_{71}$BM film in a vacuum (~10$^6$ torr) at rate of 1 Å sec$^{-1}$ for 10 nm and then 2.5 Å sec$^1$ with a total thickness of approximately 100 nm. All fabrication and testing were carried out inside a nitrogen atmosphere drybox.

Device testing. Device J-V curves were measured with a Keithley 2602 source-measure unit while illuminated with a simulated 100 mWcm$^{-2}$ AM 1.5 G light source using a 300W Xe arc lamp with an AM1.5 global filter. Solar-simulator illumination intensity was measured using a standard silicon photovoltaic with a protective KG1 filter calibrated by the National Renewable Energy Laboratory. IPCE spectra measurements were made with a 75W Xe source, monochromator, optical chopper, lock-in amplifier, and a National Institute of Standards and Technology traceable silicon photodiode for monochromatic power-density calibration. Mismatch factors of the integrated IPCE for the devices were calculated to be less than 3.1%

Example 19

Organic Solar Cell Device using Compound 103

Figure 18:
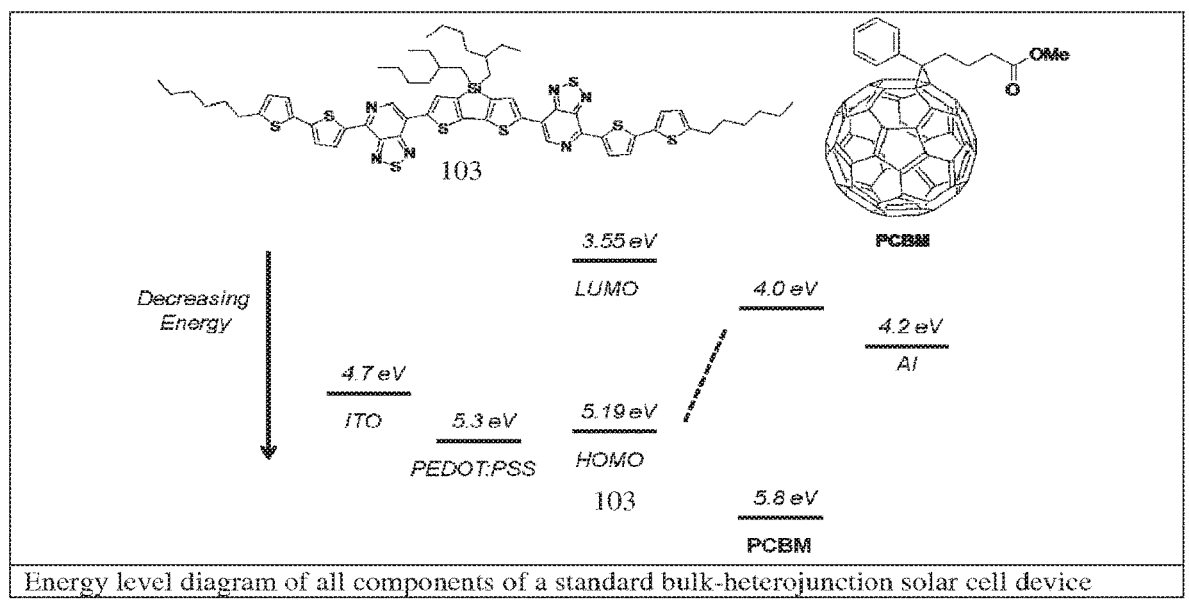
FIG. 18 shows energy levels of an organic solar cell device using compound 103.

FIG. 18 shows the energy level diagram of a standard bulk-heterojunction solar cell device fabricated using compound 103.

Example 20

Figure 19:
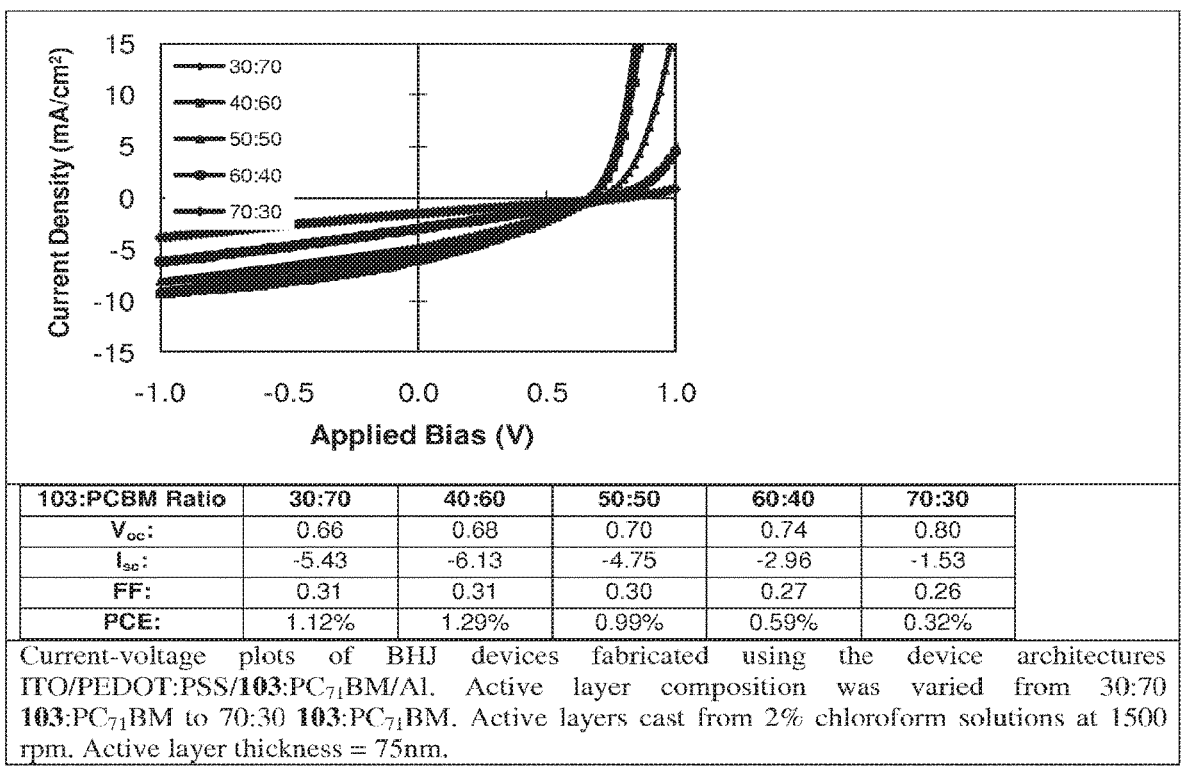
FIG. 19 shows data for solar cells fabricated using compound 103, Active layer thickness=75 nm. As-cast devices.

FIG. 19 and Table 1 show current-voltage plots of bulk heterojunction devices fabricated using the device architectures ITO/PEDOT:PSS/103:PC$_{71}$BM/Al. The active layer composition was varied from 30:70 103:PC$_{71}$BM to 70:30 103:PC$_{71}$BM. The active layers were cast from 2% chloroform solutions at 1500 rpm, Active layer thickness=75 nm.

Example 21

FIG. 20 and Table 2 show the current-voltage plots of BHJ devices fabricated using the device architectures ITO/PEDOT:PSS/103:PC$_{71}$BM/Al. Active layer composition was varied from 30:70 103:PC$_{71}$BM to 70:30 103:PC$_{71}$BM. Active layers cast from 2% chloroform solutions at 1500 rpm. Active layer thickness=75 nm. Devices annealeds at 110° C. for 2 minutes under N$_2$.

Example 22

Figure 21:
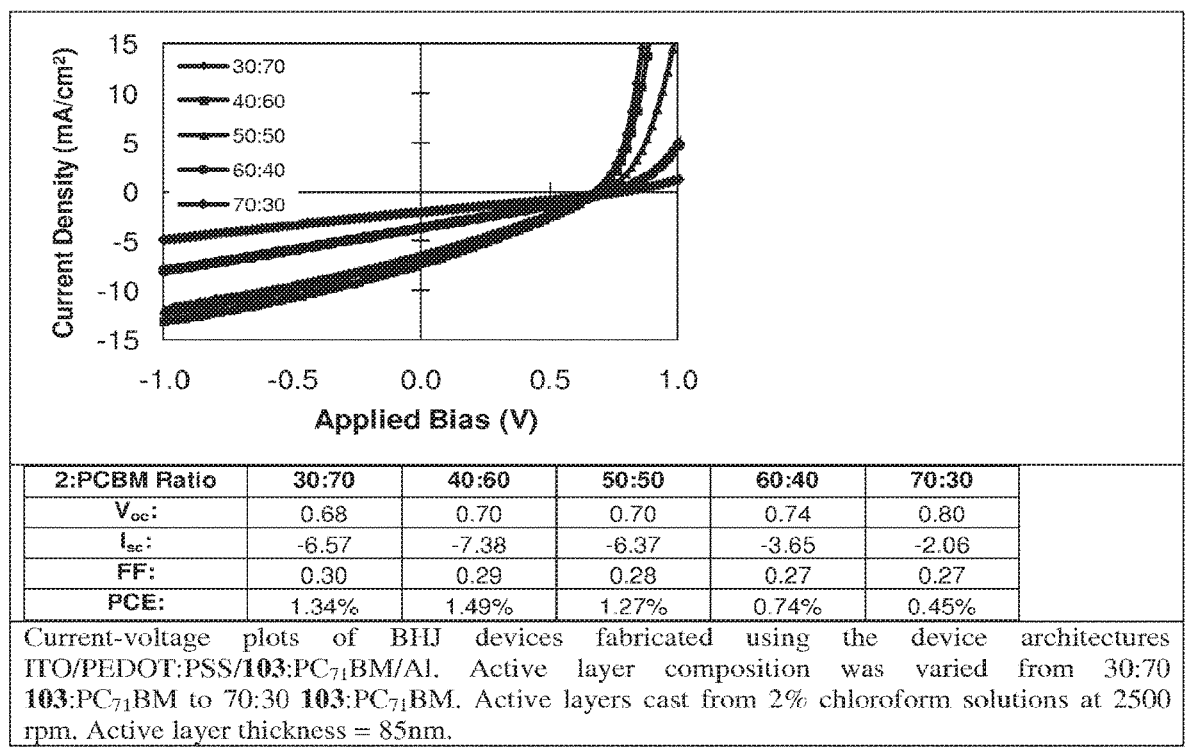
FIG. 21 shows data for solar cells fabricated using compound 103. Active layer thickness=85 nm. As-cast devices.

FIG. 21 and Table 3 show current-voltage plots of bulk heterojunction devices fabricated using the device architectures ITO/PEDOT:PSS/103:PC$_{71}$BM/Al. The active layer composition was varied from 30:70 103:PC$_{71}$BM to 70:30 103:PC$_{71}$BM. The active layers were cast from 2% chloroform solutions at 2500 rpm. Active layer thickness=85 nm.

Example 23

FIG. 22 and Table 4 show the current-voltage plots of BHJ devices fabricated using the device architectures ITO/PEDOT:PSS/103:PC$_{71}$BM/Al. Active layer composition was varied from 30:70 103:PC$_{71}$BM to 70:30 103:PC$_{71}$BM. Active layers cast from 2% chloroform solutions at 2500 rpm. Active layer thickness=85 nm. Devices annealed at 110° C. for 2 minutes under N$_2$.

Example 24

Figure 23:
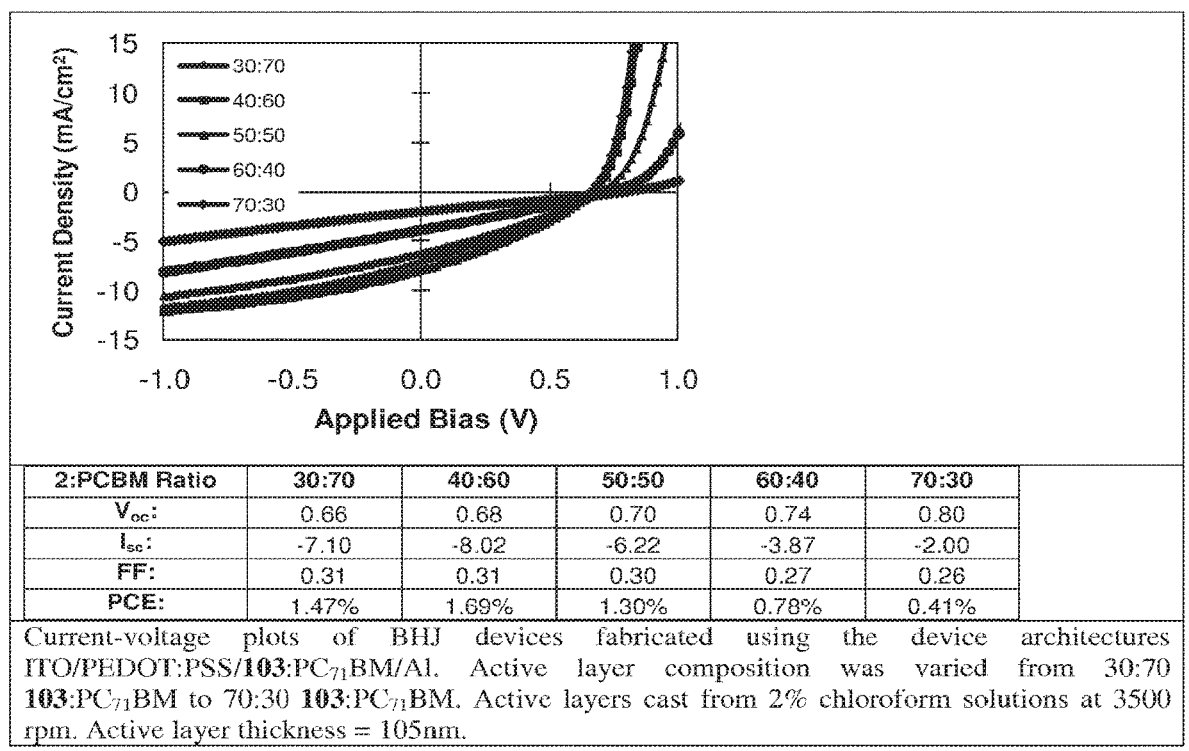
FIG. 23 shows data for solar cells fabricated using compound 103 e layer thickness=105 nm. As-cast devices.

FIG. 23 and Table 5 show current-voltage plots of bulk heterojunction devices fabricated using the device architectures ITO/PEDOT:PSS/103:PC$_{71}$BM/Al. The active layer composition was varied from 30:70 103:PC$_{71}$BM to 70:30 103:PC$_{71}$BM. The active layers were cast from 2% chloroform solutions at 3500 rpm. Active layer thickness=105 nm.

Example 25

FIG. 24 and Table 6 show the current-voltage plots of BHJ devices fabricated using the device architectures ITO/PEDOT:PSS/103:PC$_{71}$BM/Al. Active layer composition was varied from 30:70 103:PC$_{71}$BM to 70:30 103:PC$_{71}$BM. Active layers cast from 2% chloroform solutions at 3500 rpm. Active layer thickness=105 nm. Devices annealed at 110° C. for 2 minutes under N$_2$.

Example 26

Figure 25:
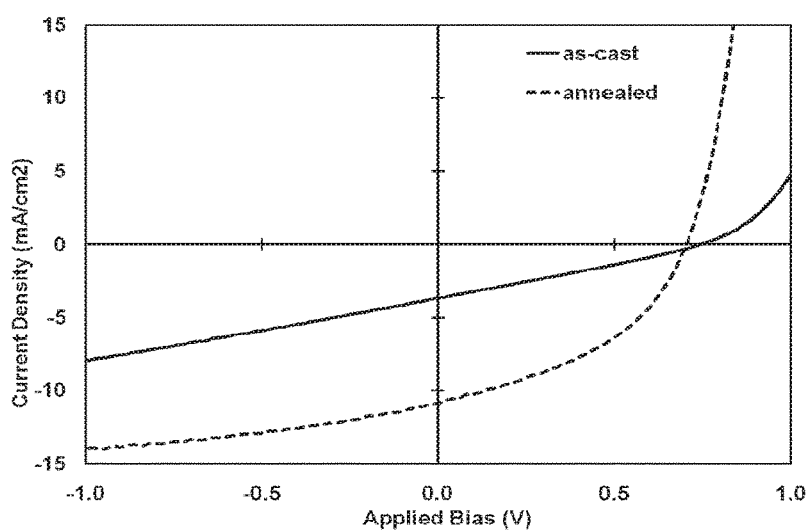
FIG. 25 shows data (current-voltage curves) for additional solar cells fabricated using compound 103.

FIG. 25 shows the best current-voltage plots of BHJ devices fabricated using the device architectures ITO/PEDOT:PSS/103:PC$_{71}$BM/Al. Active layer composition was 60:40 103:PC$_{71}$BM. Active layers cast from 2% chloroform solutions at 2500 rpm. Active layer thickness=85 nm. Device annealed at 110° C. for 2 minutes under N$_2$.

Example 27

Figure 26:
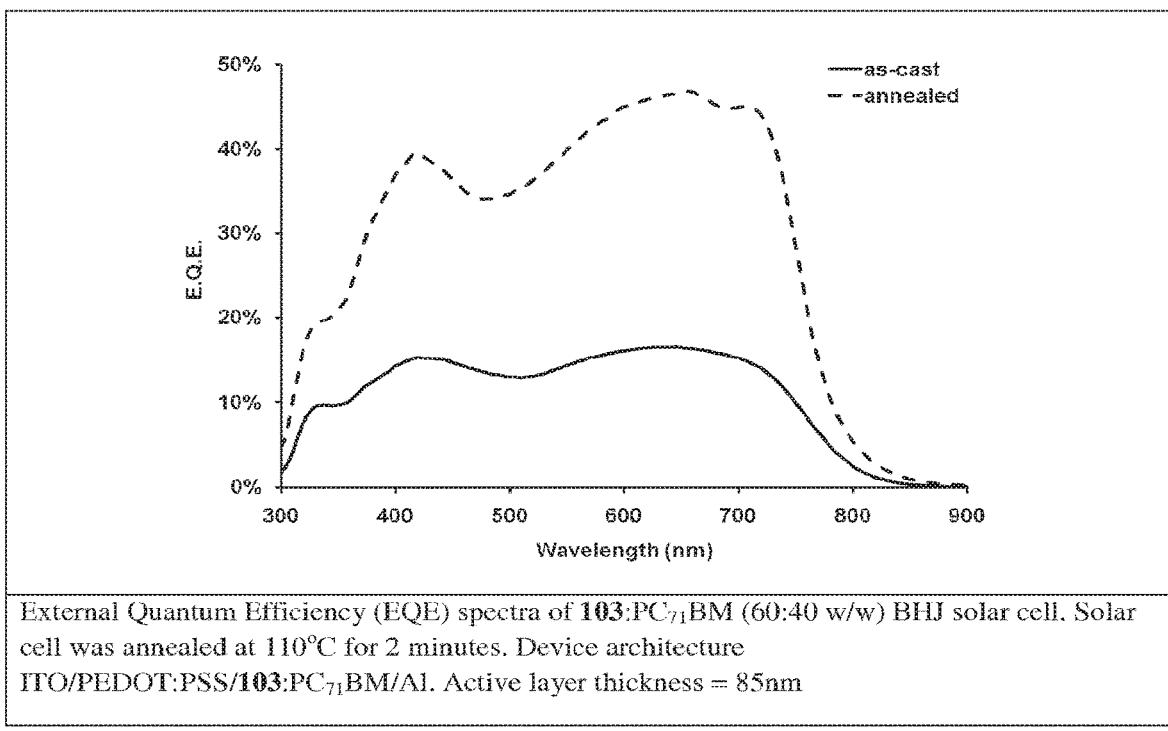
FIG. 26 shows data (EQE spectra) for additional solar cells fabricated using compound 103.

FIG. 26 shows the EQE spectra of best BHJ devices fabricated using the device architectures ITO/PEDOT:PSS/103:PC$_{71}$BM/Al. Active layer composition was 60:40 103:PC$_{71}$BM. Active layers cast from 2% chloroform solutions at 2500 rpm. Active layer thickness=85 nm. Device annealed at 110° C. for 2 minutes under N$_2$.

Example 28

Figure 27:
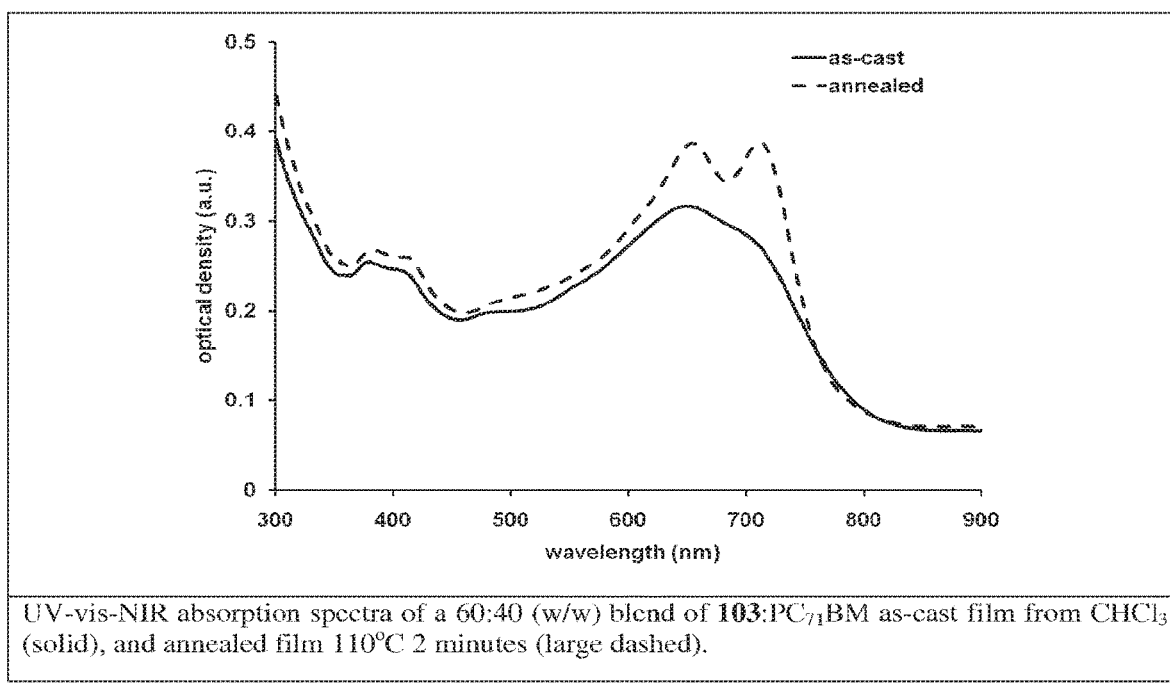
FIG. 27 shows data for 103:PC₇₁BM film blends.

FIG. 27 shows the UV-vis-NIR absorption spectra of a 60:40 (w/w) blend of 103:PC$_{71}$BM as-cast film from CHCl$_3$ (solid), and annealed film 110° C. 2 minutes (large dashed).

Example 29

Field Effect Transistor

FIG. 28 shows an example of an organic field effect transistor using material 103. Films were spun cast from 0.5% w/V in chloroform onto cleaned SiO$_2$ substrate at 2000 rpm for 40 s. An Au electrode was thermally deposited at 4×10$^{-7}$ Torr for 85 nm using a shadow mask with dimensions of L=40 µm and W=1 mm. For annealed samples, samples were annealed on a hotplate at 120° C. for 15 minutes prior to electrode deposition.

FIG. 28 shows the FET device output (top) and transfer (bottom) current-voltage curves The average FET mobility of example compound 103 for as-cast film=7.61×10$^{-03}$ cm$^2$/Vs, while the average FET mobility of example compound 103 for annealed film=1.11×10$^{-03}$ cm$^2$/Vs.

Example 30

Proposed Synthesis of Pyridaloxadiazole (PO) Organic Intermediate

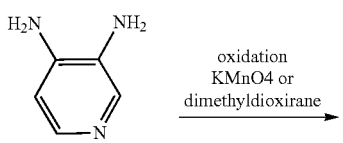

Comerically availbe Alfa Aesar

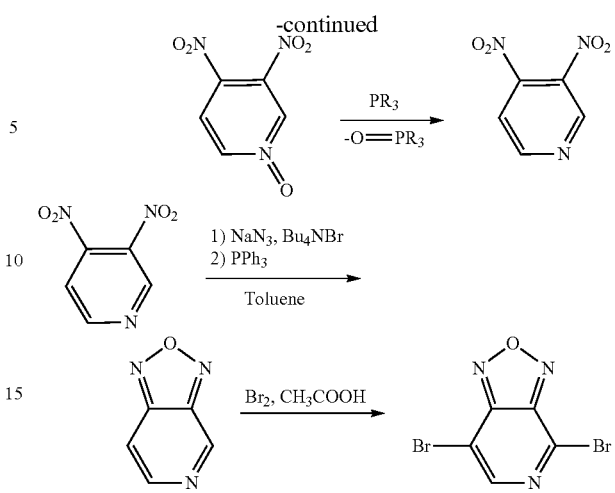

The pyridaloxadiazole (PO) core structure is synthesized as outlined above. For relevant literature see: M. Leclerc et al. Journal of the American Chemical Society, 2008, 130, 732.; R A. J. Janssen et al. Chemistry of Materials, 2009, 21, 4669.; T. M. Swager et al. Macromolecules, 2008, 41, 5559.; March's Advanced Organic Chemistry, 5$^{th}$ Ed., Wiley, 2001.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A compound of Formula IV-V:

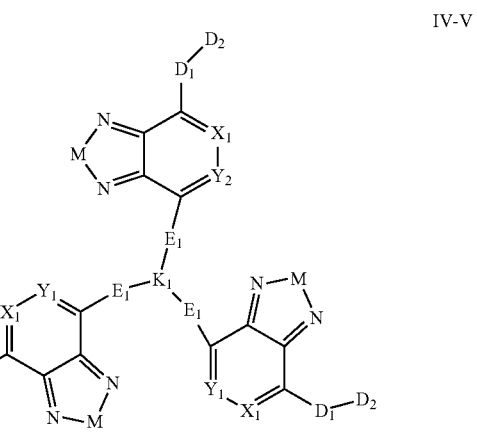

IV-V where X$_1$ and Y$_1$ are selected from N and CH, where when X$_1$ is N, Y$_1$ is CH, and when X$_1$ is CH, Y$_1$ is N M is selected from sulfur (S), oxygen (O), or N-R$_1$, where R$_1$ is H, C$_1$-C$_{30}$ alkyl or C$_6$-C$_{30}$ aryl;

K$_1$ is independently selected from substituted or unsubstituted aryl or heteroaryl;

each E$_1$ is independently either absent, or selected from substituted or unsubstituted aryl or heteroaryl groups;

each $D_1$ is independently selected from substituted or unsubstituted aryl or heteroaryl groups; and each $D_2$ is independently selected from a nonentity, H, F, a $C_1$-$C_{16}$ alkyl group, or a substituted or unsubstituted aryl or heteroaryl group.

2. A compound of claim 1 of Formula IVa or Formula IVb:

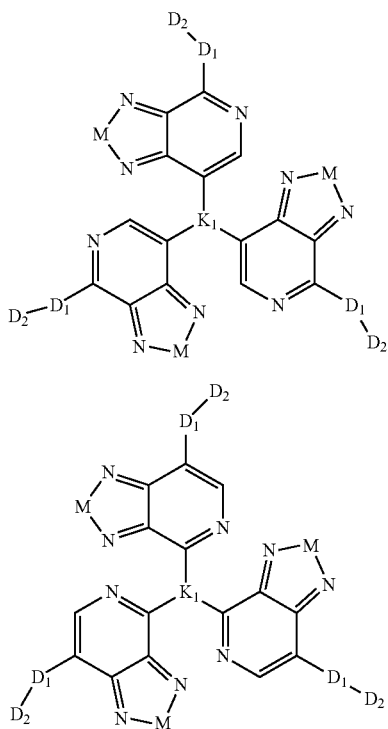

where M is selected from sulfur (S), oxygen (O), or N-$R_1$, where $R_1$ is H, $C_1$-$C_{30}$ alkyl or $C_6$-$C_{30}$ aryl;

where $K_1$ is independently selected from substituted or unsubstituted aryl or heteroaryl groups;

each $D_1$ is independently selected from substituted or unsubstituted aryl or heteroaryl groups; and each $D_2$ is independently selected from a nonentity, H, F, a $C_1$-$C_{16}$ alkyl group, or a substituted or unsubstituted aryl or heteroaryl group.

3. A compound of claim 1 of Formula Va or Formula Vb:

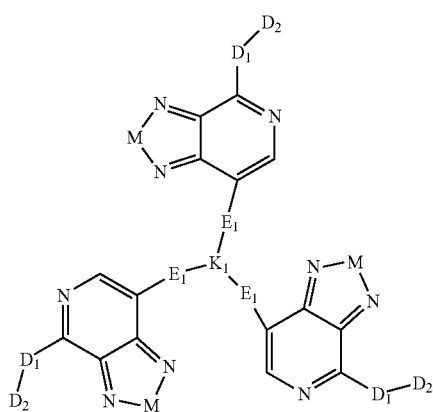

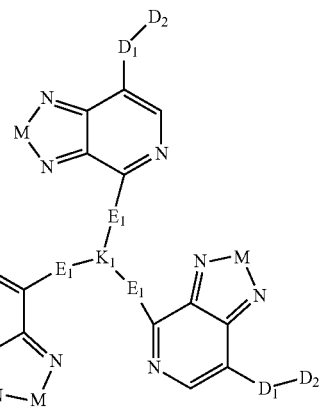

where M is selected from sulfur (S), oxygen (O), or N-$R_1$, where $R_1$ is H, $C_1$-$C_{30}$ alkyl or $C_6$-$C_{30}$ aryl;

where $K_1$ is independently selected from substituted or unsubstituted aryl or heteroaryl groups;

each $D_1$ and $E_1$ is independently selected from substituted or unsubstituted aryl or heteroaryl groups; and each $D_2$ is independently selected from a nonentity, H, F, a $C_1$-$C_{16}$ alkyl group, or a substituted or unsubstituted aryl or heteroaryl group.

4. An electronic or optoelectronic device comprising a non-polymeric compound of claim 1, where said non-polymeric compound is an electron acceptor or is an electron donor in an active layer of the electronic or optoelectronic device.

5. An electronic or optoelectronic device comprising a non-polymeric compound of claim 3, where said non-polymeric compound is an electron acceptor or is an electron donor in an active layer of the electronic or optoelectronic device.

6. A device comprising:
1) a first hole-collecting electrode optionally coated onto a transparent substrate;
2) an optional layer or layers adjacent to the first electrode selected from an electron-blocking layer, exciton-blocking layer, or hole-transporting layer;
3) a layer comprising a mixture of an electron acceptor material and an organic non-polymeric electron donor, said electron donor comprising a compound of claim 1;
4) an optional layer or layers selected from a hole-blocking layer, exciton-blocking layer, or electron-transporting layer; and
5) a second electron-collecting electrode.

7. A device comprising:
1) a first hole-collecting electrode optionally coated onto a transparent substrate;
2) an optional layer or layers adjacent to the first electrode selected from an electron-blocking layer, exciton-blocking layer, or hole-transporting layer;
3) a layer comprising a mixture of an electron acceptor material, and an organic non-polymeric electron donor, said electron donor comprising a compound of claim 3;
4) an optional layer or layers selected from a hole-blocking layer, exciton-blocking layer, or electron-transporting layer; and
5) a second electron-collecting electrode.

8. A device comprising:
1) a first hole-collecting electrode optionally coated onto a transparent substrate;

2) an optional layer or layers adjacent to the first electrode selected from an electron-blocking layer, exciton-blocking layer, or hole-transporting layer;
3) a layer comprising a mixture of an organic non-polymeric electron acceptor material and an electron donor, said electron acceptor comprising a compound of claim 1;
4) an optional layer or layers selected from a hole-blocking layer, exciton-blocking layer, or electron-transporting layer; and
5) a second electron-collecting electrode.

9. A device comprising:
1) a first hole-collecting electrode optionally coated onto a transparent substrate;
2) an optional layer or layers adjacent to the first electrode selected from an electron-blocking layer, exciton-blocking layer, or hole-transporting layer;
3) a layer comprising a mixture of an organic non-polymeric electron acceptor material and an electron donor, said electron acceptor comprising a compound of claim 3;
4) an optional layer or layers selected from a hole-blocking layer, exciton-blocking layer, or electron-transporting layer; and
5) a second electron-collecting electrode.

10. A device comprising:
1) a dielectric substrate;
2) an optional layer or layers adjacent the dielectric substrate, used to modify the surface energy of the dielectric and/or to facilitate deposition of the active layer;
3) an active layer comprising an organic non-polymeric hole transporting material comprising a compound of claim 1; and
4) a metal electrode to facilitate charge injection and collection.

11. A device comprising:
1) a dielectric substrate;
2) an optional layer or layers adjacent the dielectric substrate, used to modify the surface energy of the dielectric and/or to facilitate deposition of the active layer;
3) an active layer comprising an organic non-polymeric electron transporting material comprising a compound of claim 1; and
4) a metal electrode to facilitate charge injection and collection.

12. A device according to claim 10, wherein the dielectric substrate is $Si/SiO_2$.

13. A device according to claim 4, wherein the non-polymeric compound has a solubility of at least about 5 mg/mL in an organic solvent.

14. The device of claim 13, wherein the organic solvent is selected from chloroform, toluene, chlorobenzene, methylene dichloride, tetrahydrofuran, and carbon disulfide.

15. The compound of claim 1, wherein $K_1$ is independently selected from $C_6$-$C_{30}$ substituted or unsubstituted aryl or heteroaryl groups.

16. The compound of claim 1, wherein $K_1$ is independently selected from $C_6$-$C_{20}$ substituted or unsubstituted aryl or heteroaryl groups.

17. The compound of claim 1, wherein $K_1$ is independently selected from $C_6$-$C_{10}$ substituted or unsubstituted aryl or heteroaryl groups.

* * * * *